US009232917B2

(12) United States Patent
Addington et al.

(10) Patent No.: US 9,232,917 B2
(45) Date of Patent: *Jan. 12, 2016

(54) URINARY CATHETER SYSTEM FOR DIAGNOSING A PHYSIOLOGICAL ABNORMALITY SUCH AS STRESS URINARY INCONTINENCE

(71) Applicant: PNEUMOFLEX SYSTEMS, LLC, Melbourne, FL (US)

(72) Inventors: W. Robert Addington, Melbourne Beach, FL (US); Stuart P. Miller, Indialantic, FL (US)

(73) Assignee: Pneumoflex Systems, LLC, Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,653

(22) Filed: May 19, 2015

(65) Prior Publication Data
US 2015/0257695 A1 Sep. 17, 2015

Related U.S. Application Data

(63) Continuation-in-part of application No. 14/294,747, filed on Jun. 3, 2014, which is a continuation-in-part of application No. 13/838,196, filed on Mar. 15, 2013, now abandoned, which is a continuation-in-part of (Continued)

(51) Int. Cl.
*G06F 19/00* (2011.01)
*A61B 5/00* (2006.01)
(Continued)

(52) U.S. Cl.
CPC .............. *A61B 5/205* (2013.01); *A61B 5/0488* (2013.01); *A61B 5/0816* (2013.01); *A61B 5/113* (2013.01);
(Continued)

(58) Field of Classification Search
None
See application file for complete search history.

(56) References Cited

U.S. PATENT DOCUMENTS 4,168,703 A 9/1979 Kenigsberg
4,327,731 A 5/1982 Powell
(Continued)

FOREIGN PATENT DOCUMENTS

JP 2010201128 9/2010
WO 9011042 10/1990
(Continued)

OTHER PUBLICATIONS

Addington et al., "Inspiration closure reflex; the effect of respiration on intrinsic sphincters", Muscle & Nerve, vol. 47, No. 3, Mar. 2013, pp. 424-431.
(Continued)

*Primary Examiner* — William Thomson
*Assistant Examiner* — Davin Sands
(74) *Attorney, Agent, or Firm* — Allen, Dyer, Doppelt, Milbrath & Gilchrist, P.A.

(57) ABSTRACT

A system evaluates a patient for a physiological abnormality. A urinary catheter is insertable within a patient's bladder and has a first pressure sensor for measuring bladder pressure and a second pressure sensor for measuring mid-urethral pressure at the mid-urethral sphincter. A processing device is connected to the first and second pressure sensors and configured to receive the measured bladder pressure and measured mid-urethral pressure during at least one breath cycle and process the data representative of the bladder and mid-urethral pressures obtained during the at least one breath cycle to diagnose a physiological abnormality within the patient.

12 Claims, 35 Drawing Sheets

Related U.S. Application Data application No. 13/456,841, filed on Apr. 26, 2012, now Pat. No. 9,005,121.

(60) Provisional application No. 61/480,625, filed on Apr. 29, 2011, provisional application No. 61/533,389, filed on Sep. 12, 2011, provisional application No. 62/007,545, filed on Jun. 4, 2014.

(51) Int. Cl.

| | |
|---|---|
| *A61B 5/20* | (2006.01) |
| *A61B 5/0488* | (2006.01) |
| *A61B 5/08* | (2006.01) |
| *A61B 6/00* | (2006.01) |
| *A61B 5/113* | (2006.01) |
| *A61B 5/22* | (2006.01) |
| *A61N 1/36* | (2006.01) |
| *A61M 15/00* | (2006.01) |

(52) U.S. Cl.
CPC ............... *A61B 5/202* (2013.01); *A61B 5/227* (2013.01); *A61B 5/4211* (2013.01); *A61B 5/4884* (2013.01); *A61B 5/6852* (2013.01); *A61B 5/6853* (2013.01); *A61B 6/481* (2013.01); *A61N 1/36007* (2013.01); *G06F 19/34* (2013.01); *A61B 5/0823* (2013.01); *A61B 2562/0247* (2013.01); *A61M 15/009* (2013.01); *A61M 2209/06* (2013.01)

(56) References Cited

U.S. PATENT DOCUMENTS

| | | | |
|---|---|---|---|
| 6,354,991 B1 | 3/2002 | Gross et al. | |
| 6,743,165 B2 | 6/2004 | Mosel et al. | |
| 6,819,957 B1 | 11/2004 | Le | |
| 6,896,651 B2 | 5/2005 | Gross et al. | |
| 7,052,453 B2 | 5/2006 | Presthus et al. | |
| 7,179,219 B2 | 2/2007 | Matlock | |
| 7,317,949 B2 | 1/2008 | Morrison et al. | |
| 7,407,480 B2 | 8/2008 | Staskin et al. | |
| 7,483,755 B2 | 1/2009 | Ingle et al. | |
| 7,536,225 B2 | 5/2009 | Spraker et al. | |
| 7,686,760 B2 | 3/2010 | Anderson et al. | |
| 7,753,839 B2 | 7/2010 | Siegel et al. | |
| 8,195,296 B2 | 6/2012 | Longhini et al. | |
| 8,332,041 B2 | 12/2012 | Skelton et al. | |
| 8,597,183 B2 | 12/2013 | Addington et al. | |
| 8,597,184 B2 | 12/2013 | Addington et al. | |
| 8,602,987 B2 | 12/2013 | Addington et al. | |
| 8,652,066 B2 | 2/2014 | Addington et al. | |
| 8,690,790 B2 | 4/2014 | Addington et al. | |
| 8,840,550 B2 | 9/2014 | Addington et al. | |
| 8,845,533 B2 | 9/2014 | Addington et al. | |
| 8,845,534 B2 | 9/2014 | Addington et al. | |
| 9,005,121 B2 | 4/2015 | Addington et al. | |
| 9,005,122 B2 | 4/2015 | Addington et al. | |
| 9,005,123 B2 | 4/2015 | Addington et al. | |
| 9,005,124 B2 | 4/2015 | Addington et al. | |
| 9,011,328 B2 | 4/2015 | Addington et al. | |
| 9,028,406 B2 | 5/2015 | Addington et al. | |
| 2004/0181161 A1* | 9/2004 | Addington et al. ........... | 600/529 |
| 2005/0038328 A1* | 2/2005 | Stoehrer et al. ................ | 600/301 |
| 2005/0065450 A1* | 3/2005 | Stuebe et al. .................. | 600/547 |
| 2005/0265978 A1* | 12/2005 | Chancellor et al. .......... | 424/93.7 |
| 2005/0288603 A1* | 12/2005 | Goping .......................... | 600/561 |
| 2006/0190051 A1 | 8/2006 | Gerber et al. | |
| 2007/0135736 A1 | 6/2007 | Addington et al. | |
| 2007/0185371 A1* | 8/2007 | Bortolotti ........................ | 600/29 |
| 2007/0225576 A1* | 9/2007 | Brown et al. .................. | 600/301 |
| 2007/0225616 A1 | 9/2007 | Brown et al. | |
| 2007/0255090 A1 | 11/2007 | Addington et al. | |
| 2007/0276278 A1 | 11/2007 | Coyle et al. | |
| 2008/0077043 A1* | 3/2008 | Malbrain et al. .............. | 600/547 |
| 2009/0012350 A1* | 1/2009 | Tihon ............................. | 600/30 |
| 2009/0124937 A1* | 5/2009 | Parks ............................. | 600/593 |
| 2010/0076254 A1* | 3/2010 | Jimenez et al. ................ | 600/30 |
| 2010/0137736 A1 | 6/2010 | Addington et al. | |
| 2010/0137737 A1 | 6/2010 | Addington et al. | |
| 2011/0040157 A1 | 2/2011 | Addington et al. | |
| 2011/0040211 A1 | 2/2011 | Addington et al. | |
| 2011/0046653 A1 | 2/2011 | Addington et al. | |
| 2011/0054272 A1* | 3/2011 | Derchak ........................ | 600/301 |
| 2011/0060215 A1* | 3/2011 | Tupin et al. .................... | 600/425 |
| 2012/0190938 A1 | 7/2012 | Addington et al. | |
| 2012/0277547 A1 | 11/2012 | Addington et al. | |
| 2012/0277583 A1 | 11/2012 | Addington et al. | |
| 2013/0204313 A1 | 8/2013 | Addington et al. | |
| 2014/0288612 A1 | 9/2014 | Addington et al. | |

FOREIGN PATENT DOCUMENTS

| | | | |
|---|---|---|---|
| WO | 9918851 | 4/1999 | |
| WO | 2007079271 | 7/2007 | |
| WO | 2007081626 | 7/2007 | |
| WO | WO 2007079271 A2 * | 7/2007 | ............... A61B 5/03 |
| WO | WO 2007081626 A2 * | 7/2007 | ............... A61B 5/07 |
| WO | 2012000681 | 1/2012 | |
| WO | 2013082006 | 6/2013 | |

OTHER PUBLICATIONS

Thompson et al. "Detection of gastroesophageal reflux: value of barium studies compared with 24-hr pH monitoring" American Journal of Roentgenology, vol. 162, No. 3, pp. 621-626; Mar. 1, 1994. *See Priority U.S. Appl. No. 13/838,196, filed Mar. 15, 2013.

G. Lose "Urethral pressure and power generation during coughing and voluntary contraction of the pelvic floor in females with genuine stress incontinence" British Journal of Urology (1991) pp. 580-585. *See Priority U.S. Appl. No. 13/838,196, filed Mar. 15, 2013.

Koike et al. "Pathophysiology of urinary incontinence in murine models" International Journal of Urology (2013) pp. 64-71. *See Priority U.S. Appl. No. 13/838,196, filed Mar. 15, 2013.

Lose et al. "Initial Urethral pressure increase during stress episodes in genuine stress incontinent women" British Journal of Urology (1992) pp. 137-140. *See Priority U.S. Appl. No. 13/838,196, filed Mar. 15, 2013.

Thind et al. "The effect of bilateral pudendal blockade on the adjunctive urethral closure forces in healthy females" Scand J Urol Nephrol 28: (1994) pp. 249-255. *See Priority U.S. Appl. No. 13/838,196, filed Mar. 15, 2013.

Kamo et al. "Urethral closure mechanisms under sneeze0induced stress condition in rats: a new animal model for evaluation of stress urinary incontinence" Am J Physiol Regul Integr Comp Physiol, (2003) pp. 359-365. *See Priority U.S. Appl. No. 13/838,196, filed Mar. 15, 2013.

Kim et al. "Current trends in the management of post-prostatectomy incontinence" Korean Journal of Urology (2012) 53; pp. 511-518. *See Priority U.S. Appl. No. 13/838,196, filed Mar. 15, 2013.

Rattan et al. "Neural control of the lower esophageal sphincter" The Journal of Clinical Investigation, vol. 54; Oct. 1974; pp. 899-806. *See Priority U.S. Appl. No. 13/838,196, filed Mar. 15, 2013.

Mittal et al. "Electrical and mechanical activity in the human lower esophageal sphincter during diaphragmatic contraction" J. Clin. Invest. vol. 81, Apr. 1981; pp. 1182-1189. *See Priority U.S. Appl. No. 13/838,196, filed Mar. 15, 2013.

Huang et al. "Conventional weaning parameters do not predict extubation outcome in intubated patients requiring prolonged mechanical ventilation" Respitory Care Paper in Press: Jan. 8, 2013; pp. 1-32. *See Priority U.S. Appl. No. 13/838,196, filed Mar. 15, 2013.

Tomori et al. "Reversal of functional disorders by aspiration, expiration, and cough reflexes and their voluntary counterparts" Frontiers in Physiology vol. 3, Dec. 2012; pp. 1-14. *See Priority U.S. Appl. No. 13/838,196, filed Mar. 15, 2013.

(56) References Cited

OTHER PUBLICATIONS

Addington et al., U.S. Appl. No. 13/838,790, filed Mar. 15, 2013.
Addington et al., U.S. Appl. No. 13/767,900, filed Feb. 15, 2013.
Addington et al., U.S. Appl. No. 13/767,922, filed Feb. 15, 2013.
Chang, "An objective study of acid reflux and cough in children using an ambulatory pHmetry—cough logger" published online on Jun. 1, 2010 at Arch Dis Child. Abstract Only. *See Priority U.S. Appl. No. 13/838,196, filed Mar. 15, 2013.
Irwin "The Cough Reflex and Its Relation to Gastroesophageal Reflux," Am J Med, Mar. 2000, Abstract Only. *See Priority U.S. Appl. No. 13/838,196, filed Mar. 15, 2013.
Talasz et al. "Breathing with the pelvic floor? Correlation of pelvic floor muscle function and expiratory flows in healthy young nulliparous women" Int Urogynoeco J (2010) 21:475-481 *See Priority U.S. Appl. No. 13/838,196, filed Mar. 15, 2013.

* cited by examiner

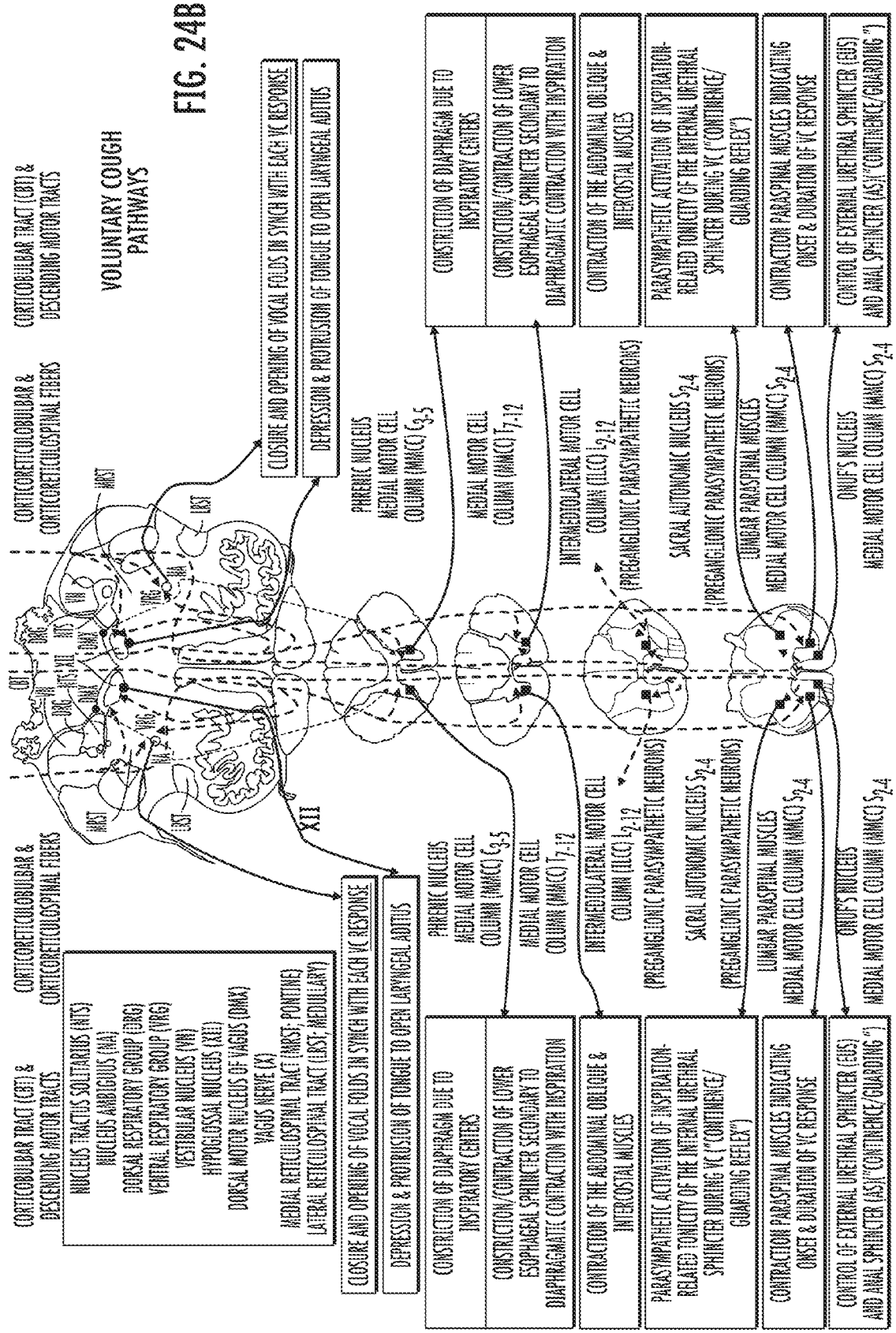

URINARY CATHETER SYSTEM FOR DIAGNOSING A PHYSIOLOGICAL ABNORMALITY SUCH AS STRESS URINARY INCONTINENCE

RELATED APPLICATION(S)

This is a continuation-in-part application of U.S. application Ser. No. 14/294,747 filed on Jun. 3, 2014, which is a continuation-in-part application of U.S. application Ser. No. 13/838,196 filed on Mar. 15, 2013, which is a continuation-in-part application of U.S. application Ser. No. 13/456,841 filed on Apr. 26, 2012 (now U.S. Pat. No. 9,005,121), which is based on provisional application Ser. No. 61/480,625 filed on Apr. 29, 2011, and provisional application Ser. No. 61/533,389 filed on Sep. 12, 2011. This application also claims priority to provisional application Ser. No. 62/007,545 filed Jun. 4, 2014.

FIELD OF THE INVENTION

This invention relates to systems that diagnose a physiological abnormality such as stress urinary incontinence, and more particularly, this invention relates to a urinary catheter system for diagnosing a physiological abnormality, including stress urinary incontinence.

BACKGROUND OF THE INVENTION

Commonly assigned U.S. Pat. Nos. 8,652,066; 8,597,183; 8,690,790; 8,602,987; and 8,597,184, the disclosures which are incorporated herein by reference in their entirety, disclose examples of systems and methodologies together with the devices and processing equipment that analyze involuntary reflex cough events and test physiological abnormalities such as stress urinary incontinence.

Commonly assigned U.S. patent application Ser. No. 14/294,747 filed on Jun. 3, 2014, the disclosure which is incorporated herein by reference in its entirety, discloses examples of analysis of the ICR and the effect of respiration on intrinsic sphincters.

Urodynamic tracings from SUI clinical trials showed that inspiration during VC stimulates pulmonary afferent fibers that activate closure of the internal urethral sphincter (IUS). The inventors have filed numerous patent applications and received patents involving the involuntary reflex cough test and analysis of stress urinary incontinence and the LER as related to the effect of inspiration and expiration on IUS and lower esophageal sphincter (LES) activity.

For example, a study has been performed using barium videofluoroscopy study (BSV) of the LES on adult males during VC, LER, breath-hold maneuvers, and normal respiration. Fiber-optic pressure catheters were placed in the LES and IUS and electromyographic (EMG) recording of the right T7-8 intercostals during respiration. The BSV showed closure and relaxation of the LES corresponding to the inspiration and expiration of VC. The LES was patented during the LER and there was closure of LES during the deep inspiration/breath-hold event. Pressure catheters in the LES and IUS showed increased pressure during inspiration and suggests that pulmonary inspiration afferents elicit a patterned reflex motor response in the LES and IUS, referred to as the inspiration closure reflex (ICR).

FIGS. 12A and 12B in the '747 application and in this application disclose clinical examples of the ICR function with a urodynamic (UD) tracing of a series of voluntary and involuntary coughs in a female subject with moderate/severe SUI. This subject had an almost two-fold increase in average IAP with the VC and each cough was preceded by deep inspiration (inhalation). During the VC, it was noted that the deep inspiration that preceded VC activated the ICR and closed the IUS, resulting in a false negative result for SUI in this "moderate to severe" subject. During the involuntary cough event, the IRCT UD tracing revealed multiple urinary leaks, despite the lower average IAP measurements compared with the VC. This suggests that if pulmonary inspiration afferent fibers are activated, these intrinsic sphincters close with every inspiration and release with every expiration. During voluntary maneuvers, such as VC, Valsalva maneuver or sneezing, these intrinsic sphincters release tonicity with expiration. The degree of intrinsic sphincter closure appears to vary with the rate, depth or volutional modification of inspiration. During inspiration, it was noted that it is possible that pulmonary inspiratory afferent fibers to the nucleus tractus solitarius (NTS) may co-activate with the phrenic nucleus, dorsal motor nucleus (DMN) and sacral autonomic nucleus. The LES closure and pressure elevation via the activation of the DMN may coincide with simultaneous activation of the diaphragm.

SUMMARY OF THE INVENTION

A system evaluates a patient for a physiological abnormality. It includes a urinary catheter insertable within a patient's bladder. The urinary catheter has a first pressure sensor on the surface of the catheter and is configured to be positioned within the patient's bladder when the catheter is inserted within the bladder for measuring bladder pressure. A second pressure sensor is on the surface of the catheter and configured to be positioned at the mid-urethral sphincter for measuring mid-urethral pressure at the mid-urethral sphincter. A processing device is connected to the first and second pressure sensors and configured to receive the measured bladder pressure and measured mid-urethral pressure during at least one breath cycle and process the data representative of the bladder and mid-urethral pressures obtained during the at least one breath cycle to diagnose a physiological abnormality within the patient.

In another example, the urinary catheter further includes a third pressure sensor on the surface of the urinary catheter and configured to be positioned at the external urethral sphincter to measure pressure at the external urethral sphincter during the at least one breath cycle. The processing device is connected to the third pressure sensor and configured to receive the data representative of the pressure at the external urethral sphincter to process that data with the data representative of the bladder and mid-urethral pressures to determine the physiological abnormality. A rectal catheter is configured to be inserted within the rectum of the patient. The rectal catheter has a pressure sensor on the surface of the rectal catheter and configured to measure pressure within the rectum during the at least one breath cycle. The processing device is connected to the pressure sensor on the surface of the rectal catheter to receive data representative of the pressure within the rectum and process with pressure data from the bladder and the mid-urethral sphincter to diagnose the physiological abnormality.

In yet another example, the urinary catheter includes a balloon configured to fix the urinary catheter within the bladder. The processing device in an example is configured to receive pressure data when a patient voluntarily coughs during the at least one breath cycle.

In yet another example, a nebulizer contains an agent that induces an involuntary reflex cough event within the patient.

The processing device is configured to receive pressure data during the involuntary reflex event. At least one electromyogram pad (EMG) is configured to be attached to the lumbar region of the patient's back and obtain EMG signals from the involuntary cough activated paraspinal muscles during the involuntary reflex cough event. The processing device is connected to the EMG pad to receive the EMG data and process the pressure data obtained from the bladder and mid-urethral sphincter with the EMG data received from the involuntary cough activated paraspinal muscles to diagnose the physiological abnormality within the patient. The processor is configured to process the pressure data to diagnose stress urinary incontinence within the patient.

A urinary catheter includes a tube configured to be inserted within the bladder of a patient. A first pressure sensor on the surface of the tube is configured to be positioned within the patient's bladder when the tube is inserted within the bladder for measuring bladder pressure. A second pressure sensor is on the surface of the tube and configured to be positioned at the mid-urethral sphincter for measuring mid-urethral pressure at the mid-urethral sphincter.

A third pressure sensor is on the surface of the tube and configured to be positioned at the external urethral sphincter to measure pressure at the external urethral sphincter. The third pressure sensor is positioned on the tube a fixed distance between the second pressure sensor and the location of the skeletal muscle of the patient in an example.

In yet another example, a method for evaluating a patient for a physiological abnormality includes inserting a urinary catheter within a patient's bladder. The urinary catheter has a first pressure sensor on the surface of the catheter and positioned within the patient's bladder for measuring bladder pressure and a second pressure sensor on the surface of the catheter and positioned at the mid-urethral sphincter for measuring mid-urethral pressure at the mid-urethral sphincter. The method includes measuring the bladder pressure and mid-urethral pressure during at least one breath cycle. The method further includes processing data representative of the bladder and mid-urethral pressures obtained during the at least one breath cycle within a processing device to diagnose a physiological abnormality within the patient.

BRIEF DESCRIPTION OF THE DRAWINGS

Other objects, features and advantages of the present invention will become apparent from the detailed description of the invention which follows, when considered in light of the accompanying drawings in which:

FIGS. 20E-20L are general views showing another embodiment of the oral-esophageal gastric device (Ng/Og device) similar to that shown in FIGS. 20A-20E but having a nebulizer function, pH sensing function and pressure sensing function, wherein the nebulizer can be used with the system and method in accordance with a non-limiting example.

FIGS. 24A and 24B are graphs detailing what occurs during LER with intrinsic sphincter activity (FIG. 24A) and voluntary cough pathways (FIG. 24B).

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 16A:
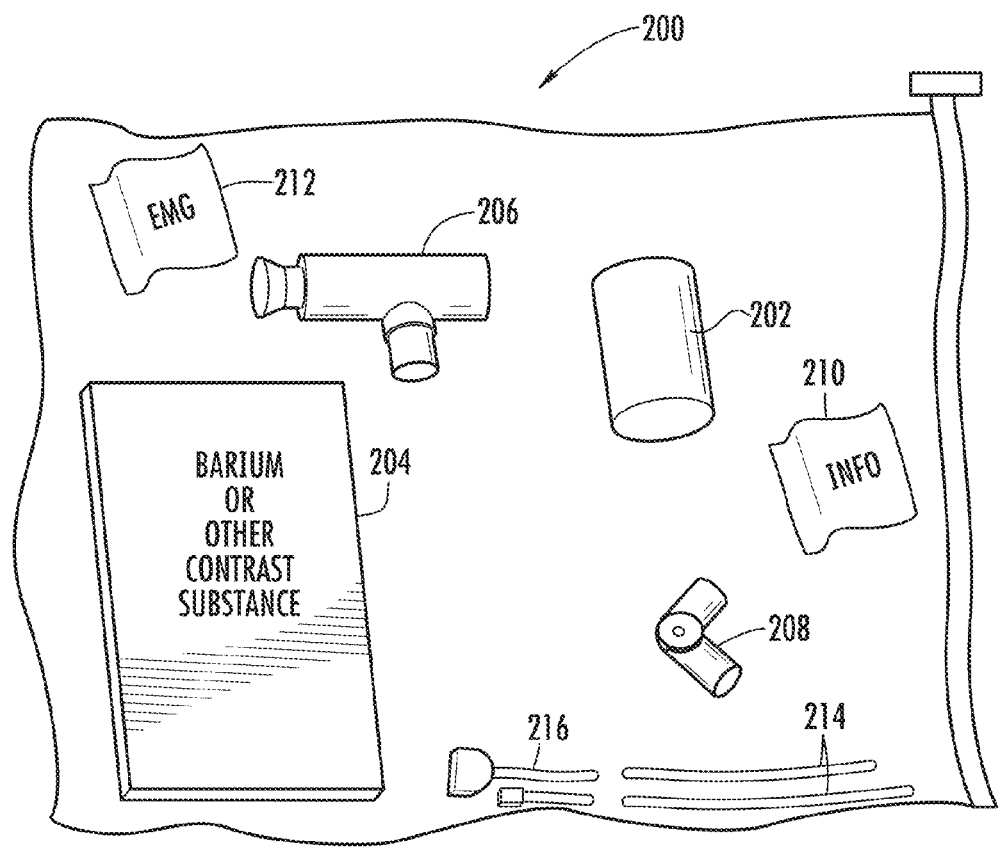
FIG. 16A is a fragmentary view of an example of a kit having components for use with the methodology described relative to FIGS. 14 and 15 in accordance with a non-limiting example.
Figure 16A:
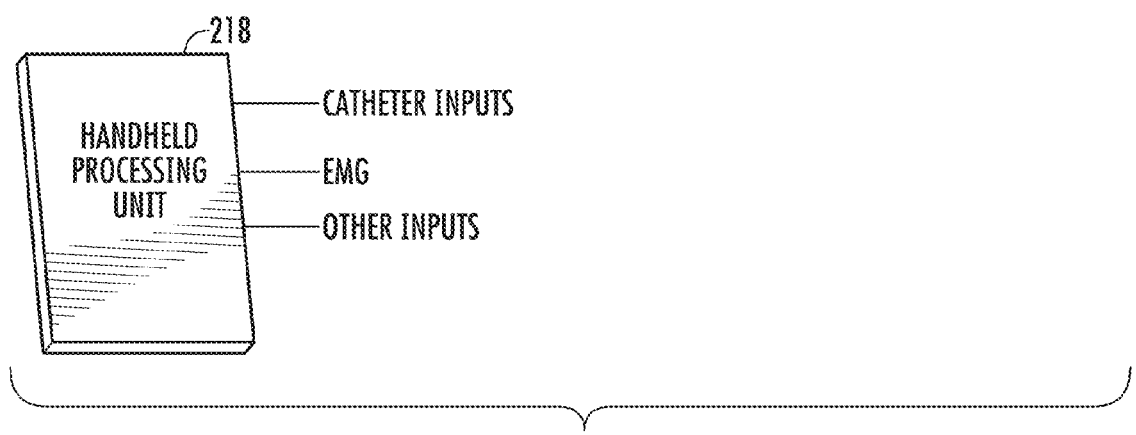

The '747 patent application and this application disclose a kit in FIG. 16A that includes a nebulizer, a tartaric acid solution, a barium sulfate solution, a swivel adapter for a nebulizer, a protocol information sheet, EMG pads, an Ng/Og tube or catheter, and a urinary catheter. It is also possible to include a kit that has a urinary catheter and a rectal catheter for further testing of urinary bladder pressure for IAP and measuring pressure at the mid-urethral sphincter and optionally at the external urethral sphincter. Thus, the urinary bladder catheter includes a transducer or sensor for the bladder pressure as intra-abdominal pressure (IAP) and a transducer or sensor at the mid-urethral area. A third transducer is located at the external urethral sphincter. These measurements will be fixed and the catheter is static such as held by a balloon or other means. A rectal catheter measures in one example the internal rectal pressure.

Figure 21:
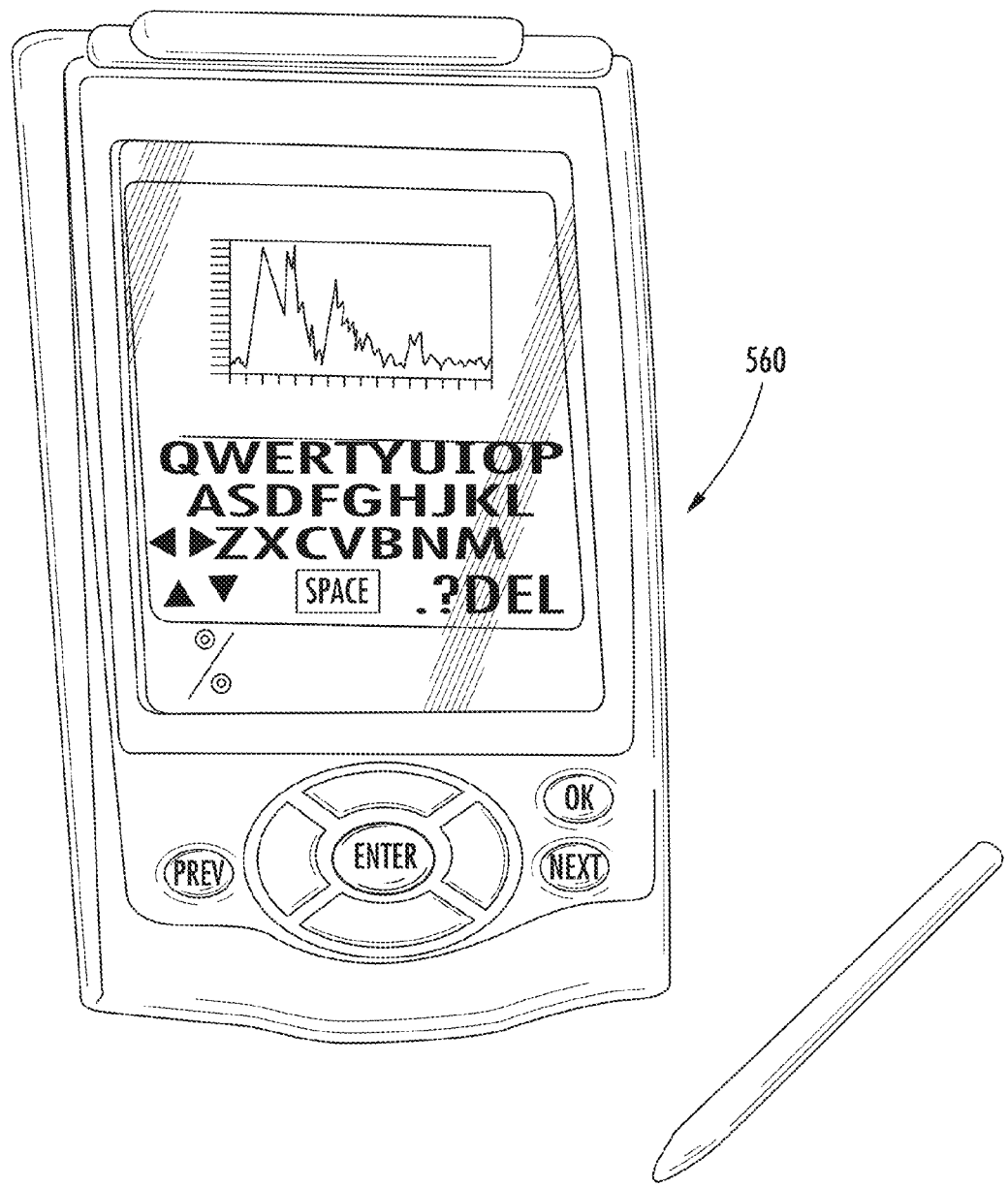
FIG. 21 is a fragmentary plan view of a handheld processing device that can be used in conjunction with various catheters and Ng/Og devices or other catheters and/or nebulizers.
Figure 22:
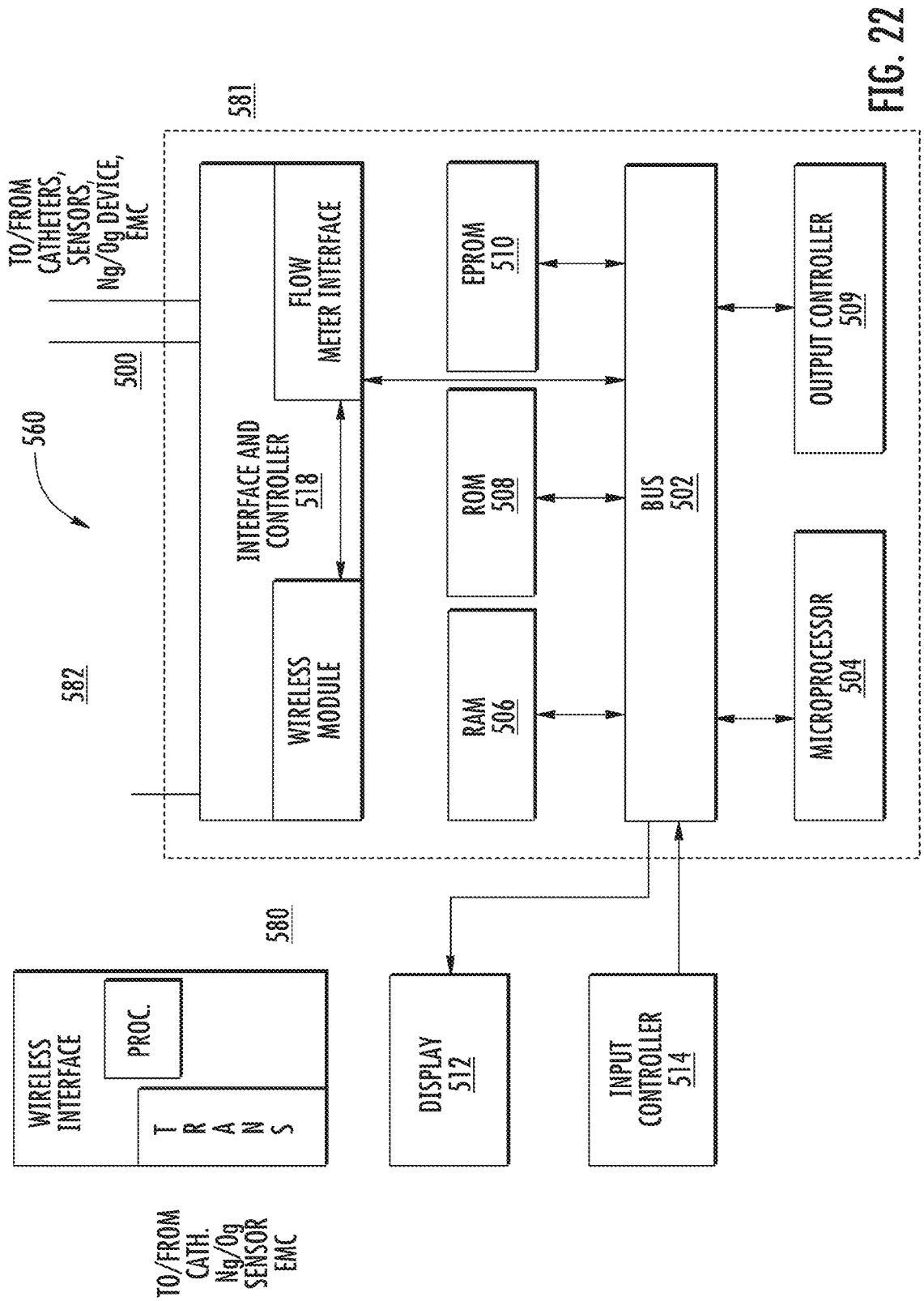
FIG. 22 is a block diagram showing example components of a handheld processing device such as shown in FIG. 21.

In an example, inputs from the catheters are to the handheld device for processing as an example shown in FIGS. 21 and 22. It is possible to measure the LER from the bladder and measure the static mid-urethral ICR pressure from the deepest breath the subject can take. It is not necessary to cough. A deep breath in many cases is sufficient. It is also possible to measure voluntary cough, involuntary cough, and the ICR. It is possible to measure the external urethral sphincter pressure with the third transducer. With use of the two catheters as the rectal catheter and urinary catheter, it is possible to perform bedside urodynamics and diagnose high pressure bladders. It is possible to determine where the primary deficit is located for SUI. It is possible to measure the external urethral sphincter by its closure pressure when voluntarily accomplished. The subject inspires and holds it to determine the external closure pressure. The subject voluntarily closes the sphincter and measures the pressure. That may inform whether there is a normal closure pressure or a weak external closure pressure.

It is possible to perform surgery in these instances, such as pre-pubic remedy instead of retro-pubic. It is possible to use a pre-pubic trans-vaginal tape, which is not used very often since most types of remedies use a retro-public solution and mid-urethral sling. If the problem is primarily an external sphincter, then there may be urinary retention and it may not cure the problem. The two electrode or three electrode catheters as described above may be wireless or plug-in. The transducer or sensor in the bladder will measure cough pressure from the voluntary or involuntary cough. The second or mid-urethral sensor or transducer will measure the mid-urethral isolated inspiration and closure pressures. It is static as compared to other types of catheters that may be pulled out and pressure measured. The pressure transducer or sensor that is mid-urethra measures the maximal inspiration closure pressure, for example, the deepest breath that can be taken. The last optional transducer or sensor at the external urethral skeletal muscle will be a fixed distance between the mid-urethral and the skeletal muscle and it does not move. The distances will not vary that much. The mid-urethral and the external urethral sphincter will be at the same place in every catheter. The mid-urethral and external urethral sphincter distances are similar in many women and sensors would not have to be moved that often except for perhaps minor adjustments such as less than a centimeter in many cases to obtain the best closure pressures for the mid-urethral and external sphincters.

Thus, the involuntary reflex cough test may be measured from the bladder and maximal mid-urethral inspiratory closure pressure measured from a static catheter that is not moving. Optionally, the external skeletal muscle closure pressure may be measured using, in one example, an air charged or similar types of catheters. Each of the internal abdominal pressure in the urinary bladder, mid-urethral pressure and optionally the external skeletal muscle closure pressure can be measured separately from the same catheter. These are different physiological maneuvers. This system will help determine where the major deficit is coming from the SUI.

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 1A:
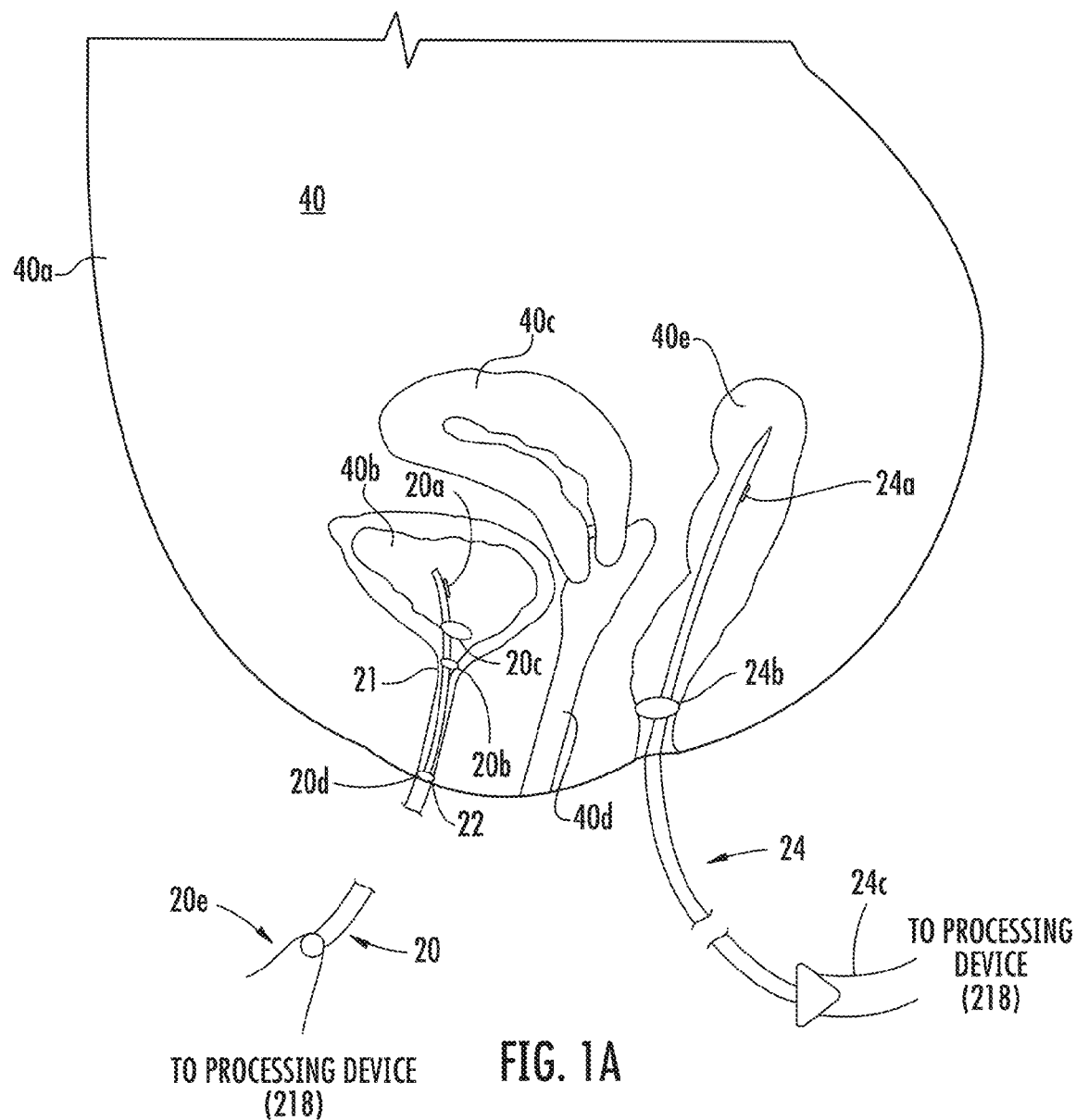
FIG. 1A is a diagrammatic view of a female anatomy showing the rectum, uterus and vagina and bladder and showing a rectal catheter and urinary catheter with various sensors for measurement.
Figure 3:
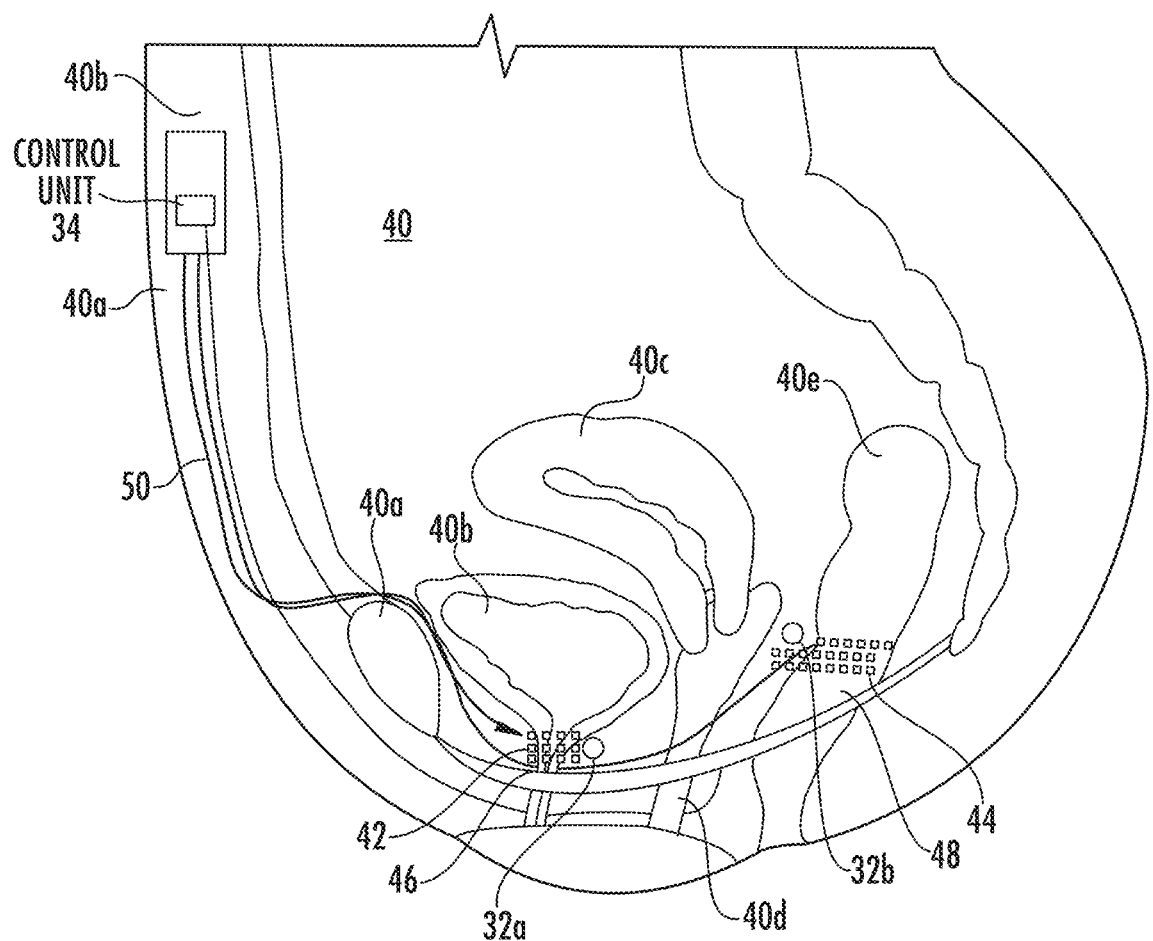
FIG. 3 is a medial view of a female pelvis showing sensors as transducers, electrodes and a processor as part of a receiver in accordance with the non-limiting example.
Figure 4:
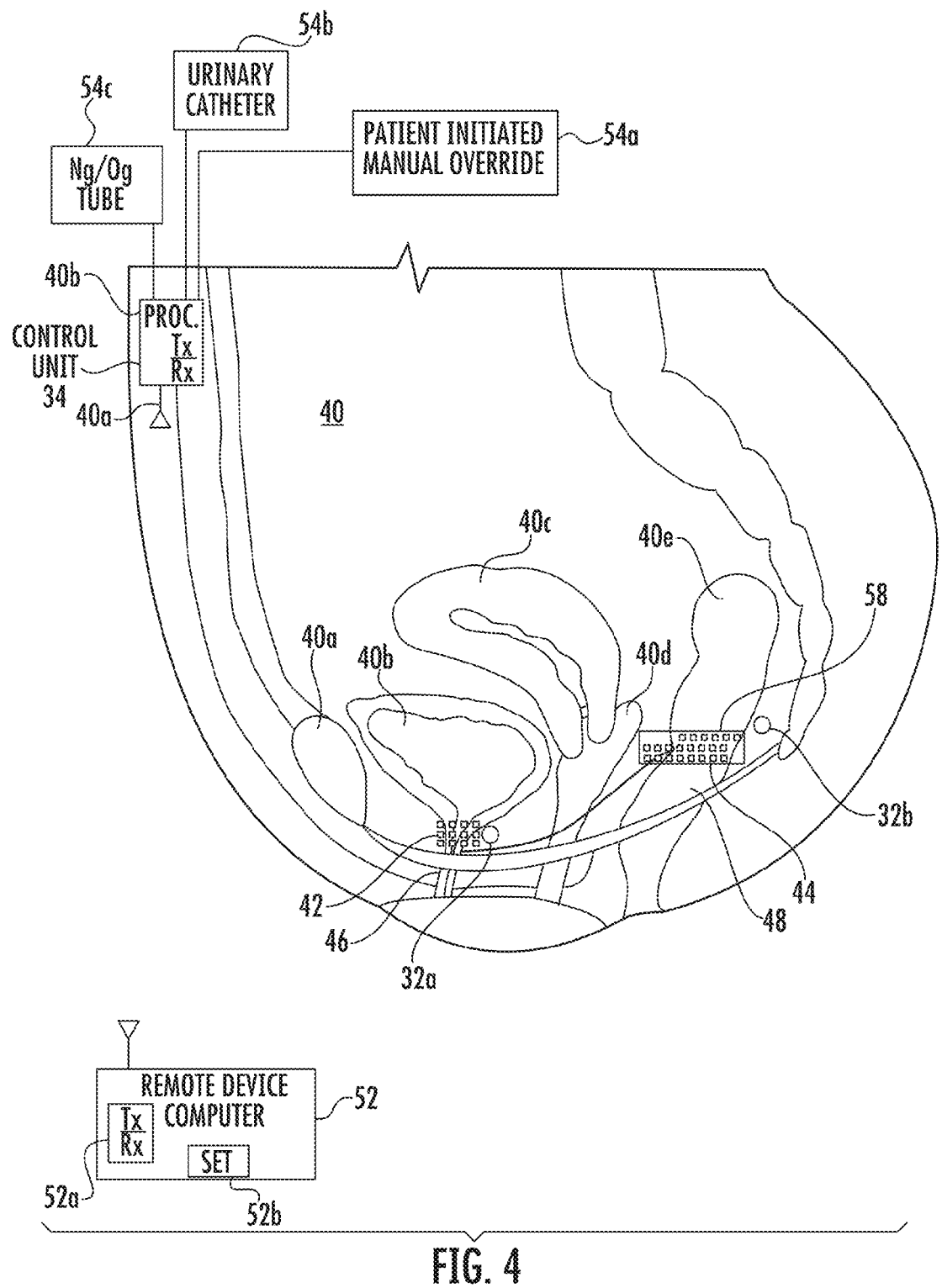
FIG. 4 is a medial view of a female pelvis showing sensors and transducers to detect inspiration and simulate the electrodes and operating wirelessly in accordance with a non-limiting example, and having additional inputs for a manual override and signals from Ng/Og and bladder catheters.

FIG. 1A shows a urinary catheter 20 inserted within a patient's bladder 40b such as a female patient. Reference is also made to FIGS. 3 and 4 for the other drawing views of the pelvic area. This urinary catheter has a first pressure sensor 20a on the surface of the catheter. The catheter is inserted within the patient with the first sensor 20a positioned in the bladder for measuring bladder pressure. A second pressure sensor 20b is on the surface of the catheter and configured to be positioned at the mid-urethral sphincter 21 as illustrated for measuring mid-urethral pressure at the mid-urethral sphincter. A balloon 20c holds or affixes the urinary catheter within the bladder similar to a Foley catheter. In this example, the first and second pressure sensors 20a, 20b may be electrodes positioned on the outer surface of the urinary catheter that is usually formed from a flexible tube. The electrodes may connect by wires to a processing device 218 (as explained below) or be wirelessly connected to a processing device, which is connected to the first and second pressure sensors and configured to receive the measured bladder pressure and measured mid-urethral pressure during at least one breath cycle and process the data representative of the bladder and mid-urethral pressures obtained during the at least one breath cycle to diagnose a physiological abnormality within the patient.

A third pressure sensor 20d may be positioned on the surface of the urinary catheter and configured to be positioned at the external urethral sphincter 22 to measure pressure at the external urethral sphincter during the at least one breath cycle. The processing device 218 is also connected to the third pressure sensor 20d and configured to receive the data representative of the pressure at the external urethral sphincter to process that data with the data representative of the bladder and mid-urethral pressures to determine the physiological abnormality. This third pressure sensor 20d may be positioned on the catheter or tube forming the catheter a fixed distance between the second pressure sensor and the location of the skeletal muscle of the patient. A communication circuit 20e connects electrodes to the processing device 218. The tube may be made of different flexible materials.

It is also possible to use a rectal catheter 24 that is inserted within the rectum 40e of the patient. This rectal catheter 40e has a pressure sensor 24a on the surface of rectal catheter and is configured to measure pressure within the rectum during the at least one breath cycle. The processing device 218 is connected to the pressure sensor on the surface of rectal catheter to receive data representative of the pressure within the rectum and processed with pressure data from the bladder and mid-urethral sphincter to diagnose the physiological abnormality. In a preferred example, the physiological abnormality of stress urinary incontinence as explained in greater detail below with various testing procedures. The rectal catheter 24 also may include a balloon 24b to fix the rectal catheter within the rectum. The rectal catheter is also formed from a tube of flexible material. It may include the communications circuit 24c similar to 20e.

In one example, the processing device 218 is configured to receive pressure data when a patient voluntarily coughs during the at least one breath cycle. A nebulizer as explained below contains an agent that induces an involuntary reflex cough event within the patient. The processing device 218 is configured to receive pressure data during the involuntary reflex cough event. In an example, at least one electromyogram pad (EMG) as explained below is configured to be attached to the lumbar region of the patient's back and obtain EMG signals from the involuntary cough activated paraspinal muscles during the involuntary reflex cough event. The processing device is connected to the EMG pad to receive the EMG data and process the pressure data obtained from the bladder and mid-urethral sphincter with the EMG data received from the involuntary cough activated paraspinal muscles to diagnose the physiological abnormality within a patient.

Urinary catheters can vary in size from a small of 5 French to as high as 26 French. The catheter may be a straight-single use catheter having a single lumen or a two-way Foley catheter as a retention catheter and include an inflatable balloon or a curved or coude cathether. It could also include a three-way Foley catheter.

It is possible to obtain the EMG from the L5/S1 paraspinal muscles and determine intra-abdominal pressure (IAP) during the involuntary reflex cough event and compare the IAP obtained from the involuntary reflex cough event to an IAP of a normal neurological range to determine if the patient is outside the normal range indicative that the patient has a neuropathological deficiency. It is possible to determine if any urine leakage time occurs and diagnose intrinsic sphincter deficiency based on urine leakage time and also determine if a disorder in the lower esophageal sphincter (LES) exists. The processing device may be configured as a portable handheld device as explained in greater detail below.

U.S. Pat. No. 9,005,121 discloses system and methods for testing the gastric valve and urethral sphincter and with analysis of the lower esophageal sphincter. Further developments, however, have now been made at observing the effect of respiration on intrinsic sphincters such as the lower esophageal sphincter (LES) and internal urethral sphincter (IUS).

The functions of the lower esophageal sphincter (LES) an internal urethral sphincter (IUS) have now been analyzed during voluntary and involuntary respiratory maneuvers. A prospective barium videoflouroscopy study (BSV) of the LES on four healthy adult men during voluntary cough (VC) was performed together with the laryngeal expiration reflex (LER), breath-hold maneuvers, and normal inspiration. One subject had fiber-optic pressure catheters placed in the LES and IUS, and electromyographic recording of the right T7-8 intercostals during respiration. The BSV showed closure and relaxation of the LES corresponding to the inspiration and expiration of VC. The LES was patent during the LER. There was closure of the LES during the deep inspiration/breath-hold event. Pressure catheters in the LES and IUS showed increased pressure during inspiration. These observations suggest that pulmonary inspiration afferents elicit a patterned reflex motor response in the LES and IUS, referred to as the inspiration closure reflex (ICR).

Test results have determined there is an Inspiration Closure Reflex (ICR) control of the IUS (Internal Urethral Sphincter). An IAP (Intra abdominal Pressure) transducer has been used for the study and data. A processor is programmed to correlate the IA (Intra abdominal) pressure changes and the associated duration of each event (as detected by the pressure transducer) with corresponding stimulation of the smooth muscle of the IUS, and/or the striated muscle of the EUS (external urethral sphincter) and/or AS (anal sphincter). Muscle stimulators may be implanted using trans-urethral or trans-vaginal approaches and connected to a processor as part of a receiver either directly such as with microwires or indirectly such as using wireless communication, for example, Bluetooth or other wireless communication.

A trans-vaginal approach is favored when a microwire is inserted via subcutaneous trochar as from the mid-line, suprapubic and inferior border of the pubic ramus. Vaginal palpation occurs at the distal end of the microwire for a muscle stimulator to the IUS, EUS, and/or AS. The confirmation of placement may be accomplished by the use of a urethral pressure catheter. It is possible to palpate the wire passing posterior to the vagina and palpate its placement adjacent to the AS surrounding the anus as distal about one inch of the rectum. The AS stimulation is confirmed by a rectal pressure catheter. The transducer and microprocessor may be connected to the stimulator via a wireless connector. A power source and electronic stimulator may be proximate to the targeted sphincter muscles in this system and apparatus.

Figure 1B:
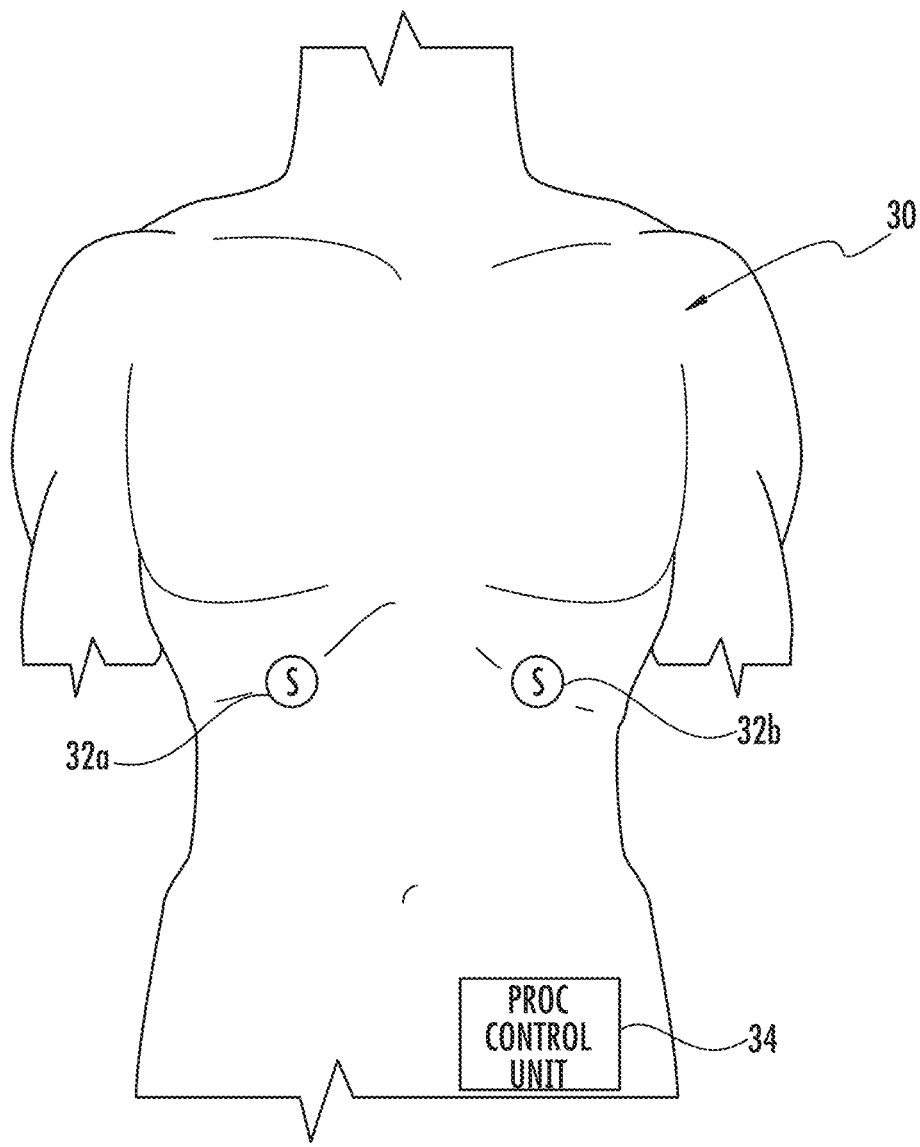
FIG. 1B is an anterior view of the human torso showing sensors such as transducers positioned to detect movement of the ribs during inspiration and expiration in accordance with a non-limiting example.

FIG. 1B shows an anterior view of the human torso at 30. The sensors 32a, 32b as transducers in this example are positioned to detect movements of the ribs during inspiration and expiration and are placed at the anterior surface of the medial border of the costal margin of ribs 8, 9 or 10. The sensors 32a, 32b in this example are formed as transducers to measure movement. These sensors 32a, 32b (either one or two) are directly or indirectly connected to a control unit 34 operative as a controller having a signal receiver/transceiver, which in this example is embedded in the subcutaneous fat of the lower quadrant of the abdominal wall. The control unit 34 controls the electrodes 42, 44 (FIG. 3) that simulate contraction of the internal urethral sphincter (IUS) and internal anal sphincter during the inspiratory phase of respiration.

Figure 2:
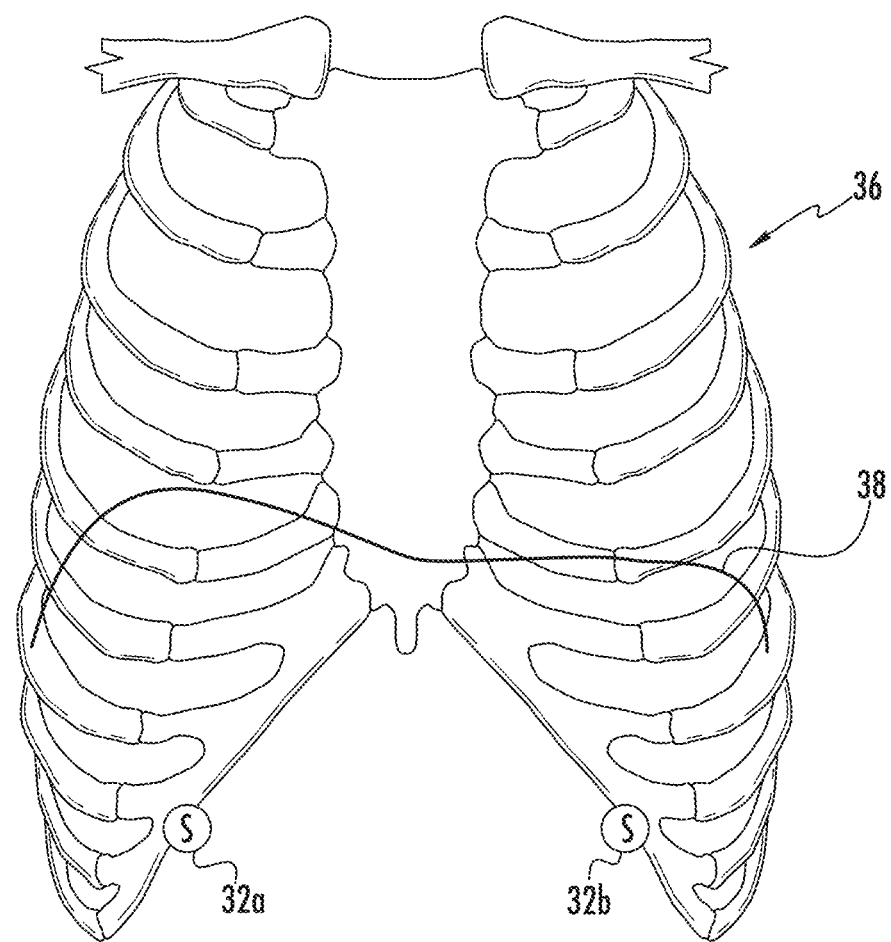
FIG. 2 is an anterior view of the human thoracic skeleton showing the sensors such as transducers to detect movement of the ribs during inspiration and expiration in accordance with a non-limiting example.

FIG. 2 shows an anterior view of the human thoracic skeleton 36. The osteocartilaginous thoracic cage 36 as illustrated includes the sternum, 12 pairs of ribs and associated costal cartilages and 12 thoracic vertebrae and intervertebral discs. The position of the superior domes of the diaphragm is indicated by the line 38. The sensors 32a, 32b are configured to detect movement of the ribs during inspiration and expiration and are placed on the anterior surface of the medial border of the costal margin of ribs 8, 9 or 10 in this example. The sensors 32a, 32b may be placed either unilaterally or bilaterally.

FIG. 3 is a medial view of the female pelvis 40. A microprocessor is part of a control unit 34 and implanted in the fatty layer (Camper's fascia 40a) or in the deep layer (Scarpa's fascia 40b) and against the fascia of the external abdominal oblique muscle in the patient's left or right lower abdominal wall. This control unit 34 receives wireless signals from the sensors 32a, 32b regarding movement of the lower rib cage during inspiration. The control unit 34 will detect the onset of inspiration and simulate microelectrodes 42, 44 that are implanted in the respective internal urethral sphincter (IUS) 46 and internal anal sphincter (IAS) 48 indicated by the multiple dotted lines on the appropriate sphincter. The control unit 34 is connected to the microelectrodes 42, 44 (single or as an array of microelectrodes either directly (via microwire) or indirectly (wireless, radio frequency, Blue-Ray, or similar technology). These pelvic devices as the microelectronics may close the IUS or IAS either electronically (muscle simulation) or activate mechanical mechanisms that close the IUS and IAS with or without an intervening processor. Microwires 50 if used are placed using a trochar to tunnel through Camper's fascia 40a (subcutaneous fat of the abdominal wall) to the superior border of the pubic bone. There is also illustrated the pubis 40a, urinary bladder 40b, uterus 40c, vagina 40d, and rectum 40e.

FIG. 4 is a medial view of the female pelvis 40. In this case the transducer as sensors 32a, 32b operate wirelessly and transmit wireless signals at the onset of inspiration, and simulate the electrodes 42, 44 and/or mechanical or electronic IUS or IAS devices (indicated by the multiple dotted lines 42, 44 on the appropriate sphincter). The attached lines represent that the electrodes could be used or other electronic or mechanical devices to close these sphincters. The electrodes 42, 44 close these sphincters during inspiration. The electrodes 42, 44 are implanted in or around the internal urethral sphincter (IUS) 46 and internal anal sphincter (IAS) 48. The sensor(s) 32a, 32b in this example are connected to the sphincter closure devices and/or either directly (via microwire) or indirectly (wireless, radio frequency, Blue-Ray, or similar technology). These pelvic devices as electrodes 42, 44 or other device may close the IUS or IAS either electronically (muscle simulation) or mechanically such as by pressing inward on the sphincter with or without an intervening processor or control unit.

Displacement of the diaphragm may be detected by one or two sensors 32a, 32b or other type of transducers, which are implanted at or on the medial costal border of the eighth rib using a trochar device to implant the small, cylindrical transducers. These motion sensors 32a, 32b as transducers detect the movement of the lower rib cage during deep inspiration. This movement of the rib cage during inspiration occurs as a result of contraction of the diaphragm and the corresponding expansion of the thoracic cavity and abdominal cavity. During inspiration, the costal margins of ribs 8-10 move supero-laterally and the two motion sensors 32a, 32b as illustrated in FIG. 4 may detect an increase in distance between the two devices and thereby rib cage expansion corresponding to inspiration.

It is possible to calibrate the system using a remote control device or computer 52 that is linked to the control unit 34 and operative as a transmitter/receiver and may be used to set the inspiration/expiration endpoints of the rib cage movement via transmission of signals wireless in this example using a transmitter/receiver circuit 52a in the remote device 52. This calibration is performed in the clinical setting by a clinician. The clinician will ask the patient to completely exhale and will then press a (set) button 52b on the remote device 52 at the end of complete exhalation. The motion sensors 32a, 32b may be directly or indirectly connected to the devices 42, 44 as electrodes in this example that close the IUS and/or IAS through muscle contraction, which will control intrinsic sphincter closure based on deep inspiration and the associated inspiration closure reflex as a normal neurological event linked to significant inspiration.

The clinician will ask the patient to deeply inhale (inspiration) and then press the [set] button 52b at the end of deep inspiration. The remote device computer 52 is linked by radio frequency, Blue-Ray or other similar communications link such as to the control unit 34 or directly to the sensors 32a, 32b and will record the inspiration/expiration endpoints and the associated range of rib cage movement. The mode of transmission of signals from the motion transducers 32a, 32b is transmitted by, but not limited to, direct or indirect communication connections to the implanted control unit 34, which can also act as a communications receiver for signals from the sensors 32a, 32b, and through a transmitter function, initiate one or more devices that cause: (1) electronic simulation of the IUS and/or LAS smooth muscle, which will contract these smooth muscle sphincters and prevent voiding and/or evacuation through electronic means; or (2) mechanical closure of the IUS and/or IAS, which contract these smooth muscle sphincters and prevent voiding and/or evacuation; through mechanical means. There can be direct or indirect connection to a mechanical and/or electronic devices, which will close these sphincters through electronic or mechanical means. The closure of these sphincters by these devices may be synchronized with the inspiration closure reflex (ICR), a normal neurological event, which occurs with deep inspiration and thereby increases intrinsic sphincter tonicity prior to a potential increase in intra-abdominal pressure (IAP).

The control unit 34, which is usually implanted, will detect the start of inspiration through the sensors 32a, 32b and initiate corresponding simulation of the microelectrodes or other devices 42, 44 at the internal urethral sphincter (IUS) 46 and/or internal anal sphincter (IAS) 48 and thereby increase sphincter tonicity. It is possible in some embodiments to receive signals from modified transducers. The device operates through its communications circuitry 35. During urinary voiding or evacuation of the bowel, the control unit 34 may be temporarily turned off and permit volitional voiding and/or evacuation of the urinary bladder or bowel, respectively. Pressing an 'on' button again, resets the device to the previous setting for respiration and control of sphincter tone and allows synchronizing of the devices or electrodes 42, 44 with the patient's inspiration.

As illustrated, the processor 40b as part of the control unit 34 may receive input from a patient initiated manual override 54a that allows a patient to override the controller to permit voiding of the bladder and rectum such that electrodes will not be delivering current to the muscles of the urethral sphincter or anal sphincter. It is also possible to receive inputs from a urinary catheter 54*b* and Ng/Og tube 54*c* that are used in conjunction with an involuntary reflex cough event.

The patient initiated manual override may include a button worn by a patient and easily accessible. For example, if a patient presses a button on the patient initiated manual override, a signal is sent to the processor and control unit 34 such that the controller bypasses the system and allows urinary voiding and bowel movement through the rectum because the sphincter muscles are not contracted and electrical signals are not sent to the electrodes on the respective sphincters. The patient initiated manual override 54*a* may also be accomplished during an involuntary reflex cough event to assess the severity and extent of stress urinary incontinence. It is possible to use the Ng/Og tube or other catheter in combination with the source of chemo-irritant that induces an involuntary reflex cough event within a patient. A catheter is inserted within the stomach and has pressure and pH sensors configured to measure intra-abdominal pressure and elevational reflux along the catheter during the involuntary reflex cough event. A processor receives the data from the pressure and pH sensors during the involuntary reflex cough event and processes the received data and determines the functional status of the gastric valve of the patient. An example of such catheter is shown in FIG. 20M. The Ng/Og tube such as shown in FIGS. 20A-20L may also be used. The controller may be configured to generate and transmit electrical control signals to the electrodes connected to the urethral sphincter during the involuntary reflex cough event and prevent urinary voiding during the involuntary reflex cough event. The manual override may be activated to allow urinary voiding and assess stress urinary incontinence.

The source of chemo-irritant such as the nebulizer shown in FIG. 16A may be used to induce the involuntary reflex cough event for testing in conjunction with an Ng/Og tube or other catheter inserted within the stomach and having pressure and pH sensors to measure the intra-abdominal pressure and measure elevational reflux and determine the functional status of the gastric valve of the patient or determine another physiological abnormality. The data obtained from this system may be used in conjunction with treatments such as a sling or retropublic suspension. It is possible to use a tension-free vaginal tape, mid-urethral sling procedure that uses mesh tape that lifts and supports the urethra, making leakage more difficult to occur. Other systems and slings may be used in conjunction with the system for better control over stress urinary incontinence issues.

The description relative to FIGS. 1-4 assist in understanding the TCR and use of the sensors as transducers 32*a*, 32*b* for diagnosing physiological conditions. The system will not usually detect phrenic nerve activity and will not usually use devices to stimulate the inferior hypogastric plexus, which innervates, in part, the internal urethral and internal anal sphincters. That type of device would involve a more invasive surgical procedure and it may be more difficult to control the IUS and IAS as the plexus innervates other pelvic structures.

Figure 4A:
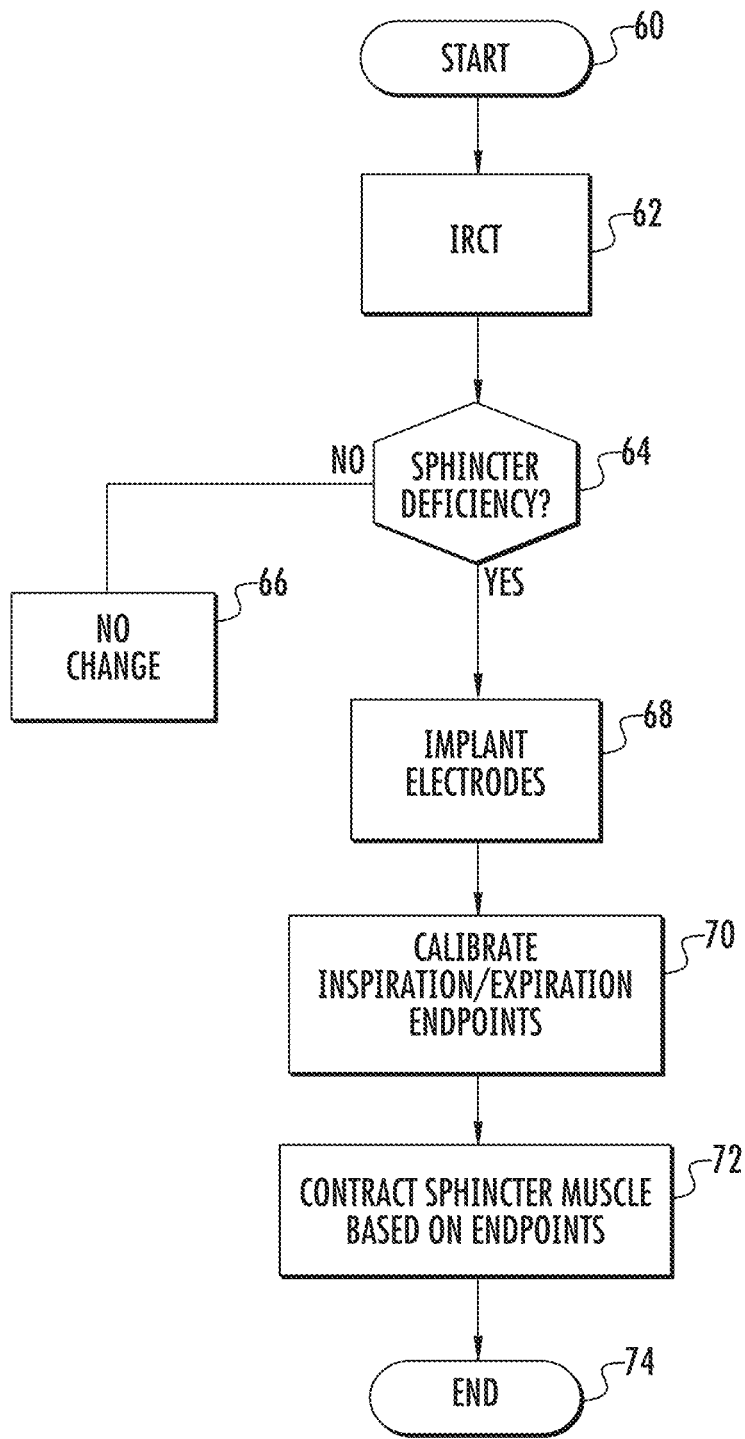
FIG. 4A is a flowchart showing a basic sequence of operation.

The process shown relative to FIGS. 1-4 starts at FIG. 4A (block 60). The involuntary reflex cough test is administered (block 62). A determination is made if there is sphincter dysfunction (block 64). If not, then there are no changes made (block 66). If yes, then electrodes are implanted (block 68). The inspiration/expiration endpoints are then calibrated (block 70). Sphincters are contracted based on the endpoints during inspiration and expiration (block 72). This process continues until a determination is made that sphincters no longer need to be contracted and the process ends (block 74).

It would be rare to have the process end since usually a patient will require the treatment over a long period of time.

Detection of diaphragmatic contraction is anatomically complicated by its close proximity to adjacent structures. Any implants or electrodes in the diaphragm may damage or injure these structures, e.g., heart, lungs, gastrointestinal tract, abdominal organs, etc., or cause a pneumothorax, hemothorax or similar breech of the pleural cavity. Thus, such a device may not be desirable. The system usually will not use a device to detect electrical activity of the phrenic nerve.

This type of system is more reliable than a phrenic nerve stimulator. If neuropathy is the cause of the ICR breakdown, it is possible to assume all nerves have some degree of ongoing neuropathy, which may get worse. If the phrenic nerve fails to activate the diaphragm, thus causing shorter movements, it may be assumed that the same process occurs with the Inferior Hypogastric Plexus to the ICR. It is possible to override these deficits to the ICR and reset the closure variables, adjustable over time, using a more reliable method than nerve assessment or activation.

The phrenic and diaphragm may be adequate but the lumbosacral stenosis injures the nerves that close the IUS. Any closure settings by this detection would be different compared to the phrenic nerve and diaphragm function. IUS activation is based in this instance on the present ability to activate the diaphragm, reflected by rib movements. If a subject is restricted in inspiration, COPD, arthritis, kyphosis or restrictive patterns of breathing, the system resets the IUS closure sensitivity to less activation from the ribs. These settings may be individually customized by the Urologist and may occur in many different patterns. Based on the ICR deficit, they are adjustable by the urologist in the clinic or with an urodynamics examination. The adjustment may be compared to other adjustment technologies, e.g., insulin, pain medicine or intrathecal Baclofen pumps. There is an override to void if the subject cannot relax and possibly deactivate a sensitive ICR setting, similar to a restrictive, kyphotic type patient. Many other options are possible.

Tunneling for the microwires 50 to the electrodes 42, 44 is straightforward to the level of the pubis. Connecting a microwire 50 to an electrode 42, 44 (or electrode array arranged on a tape), however, may require another step. It is possible to use a curved trochar or instrument similar to that used for a supra-pubic urinary bladder suspension. The wire is connected to the tape when electrodes are contained on the tape and pulled into place by palpating the placement per vagina. FIG. 4 shows a tape 58 in block format that supports the illustrated electrode array 44. It should be understood that the electrodes could be single electrodes, an array of electrodes such as on a tape or other support or other configuration.

The electrodes 42, 44 adjacent to the IUS and IAS may require a power supply and there may not be room for the power supply in the area of the pelvis, but there are improvements in power supply, especially since MEMS technology may be used for sensors and power supplies. The electrodes 42, 44 as stimulators are small and do not migrate. Another consideration for design and placement is the vascular layout of vessels and pathway of nerves, which in this area may be problematic.

It may be possible to use sensors 32*a*, 32*b* that are programmed to work with each other and the transponder devices such as the electrodes 42, 44 by movement changes. It is possible to activate the electrodes 42, 44 without wire placements. Electrodes may also be activated by sensors directly attached to them so that there are no wires and the sensors/electrodes are formed as integrated units. Possible communication linkages include Bluetooth or similar wireless technology to activate the electrodes from the control unit 34.

IRCT (involuntary reflex cough test) testing will provide more reliable data sampling of extubation failure risk than VC (voluntary cough) and especially tracheostomies, which are the majority of prolonged intubated patients. There are many variables to the possible scenarios and they require clinical judgment. It is possible to add a micro tube with a transducer that can plug into a processing device, such as the handheld processing device shown in FIGS. 21 and 22 and also Ng/Og or urology tubes as disclosed in commonly assigned U.S. Pat. Nos. 8,597,184; 9,011,328; and 9,028,306, the disclosures which are hereby incorporated by reference in their entirety. These devices can be inserted via a percutaneous endoscopic gastrostomy tube (PEG) or Jejunostomy (J-tube) and used to calculate the iRCT cough epoch values for IAP responses to help determine extubation risk.

Many prolonged intubated patients are converted from Ng/Og tubes to PEGS or J tubes for feeding, and many intubated patients are changed to tracheostomy tubes if it is a prolonged illness. Doctors continually attempt to determine what variables are required to extubate from the larynx or decannulate safely from the larynx with the least risk of reintubation. Some patents require this for post operative pneumonia prevention. Patients that receive tracheostomies are usually sicker, weaker and have a higher risk of decannulating. If it fails, the patient is not in a good place with airway management, and stomas close quickly. Many tracheostomies are usually accompanied by tube feeding from Ng, PEG or J-tubes. The doctor or the clinician may have these tubes with pressure sensors for measurement already in place with the ability to plug into a processing device to measure, or have the ability to insert a transducer to measure through these tubes, which can be removed.

It should be understood that function of the lower esophageal (LES) and internal urethral (IUS) sphincters has not been reported during voluntary and involuntary respiratory maneuvers. As noted before, prospective, barium videofluoroscopy study (BSV) of the LES was performed on four healthy adult males during voluntary cough (VC), laryngeal expiration reflex (LER), breath hold maneuvers and normal inspiration. One subject had fiberoptic pressure catheters placed in the LES and IUS, and EMG recording of the right T7-8 intercostals during respiration.

The BSV showed closure and relaxation of the LES corresponding to the inspiration and expiration of VC. The LES was patent during the LER. There was closure of the LES during the deep inspiration/breath hold event. Pressure catheters in the LES and IUS showed increased pressure during inspiration. These observations suggest that pulmonary inspiration afferents elicit a patterned reflex motor response in the LES and IUS, referred to as the Inspiration Closure Reflex (TCR).

The respiratory cycle is modified in many ways and by many influences that also activate the expiratory muscles for respiration. When the lung was distended by inspiration, pulmonary afferent impulses were conveyed to the brainstem via the Vagus nerve, and these afferent impulses reflexively initiated expiration. When the lung was deflated, other pulmonary afferent receptors were stimulated, and their impulses, also conveyed to the brainstem by the Vagus nerve, reflexively initiated the next inspiration.

Voluntary cough (VC) and the laryngeal expiration reflex (LER) as an involuntary cough have been used for assessment of stress urinary incontinence (SUI) in women and neurological airway protection in humans. The urodynamic tracings from SUI clinical trials suggest that the inspiration during VC stimulates pulmonary afferent fibers that may directly activate closure of the internal urethral sphincter (IUS).

Commonly assigned U.S. application Ser. No. 13/354,100 filed Jan. 19, 2012 by the same inventors, the disclosure which is hereby incorporated by reference in its entirety, discloses a system and method of diagnosing acid reflux using an involuntary reflex cough test. In one example as disclosed, a nasogastric/orogastric (Ng/Og) device is inserted into the stomach and the involuntary reflex cough epoch induced. The intra-abdominal pressure and elevational reflux along the Ng/Og device is measured. In an example, the functional status of the gastric valve is determined based on the measured intra-abdominal pressure and elevational reflux along the catheter.

Use of the involuntary reflex cough test with or without a voluntary cough test is also disclosed in commonly assigned U.S. Pat. Nos. 8,690,790; 8,652,066; 8,597,183; 8,602,987; 8,597,184; 9,011,328; and 9,028,406; the disclosures which are all hereby incorporated by reference in their entirety. The '184, '328 and '406 patents disclose oral-esophageal-gastric devices, some with esophageal cuffs and/or reflux measurement systems that can be used to assess GERD or determine stress urinary incontinence in some examples using the involuntary reflex cough tests alone or in combination with the voluntary cough test.

There now follows a discussion of materials and testing method. The test included a prospective, barium swallow videofluoroscopy (BSV) study. Four normal, healthy male subjects participated in the BSV study. One of the subjects also underwent evaluation of the IUS and LES using fiberoptic pressure catheters. After review of the study protocol, informed consent was obtained from all subjects. BSV studies of the LES were performed using only thin barium solution in each subject. The subjects were standing for all BSV test maneuvers using a standing anterior-posterior view. Videofluoroscopic photomontages were captured at three second intervals and analyzed for each maneuver.

For the VC, each subject swallowed a small cup of thin barium solution followed immediately by a deep inspiration and a VC. The BSV captured, at the level of the LES, a photomontage of the barium flow during the VC.

The breath hold maneuver required the subject to perform a deep inspiration and breath hold followed immediately by swallowing a small cup of thin barium solution. The BSV captured, at the level of the LES, a photomontage of the barium flow during the breath hold voluntary maneuver. All of the photomontages were visually analyzed to determine the relationship of the barium to the position of the LES and diaphragm.

The induced reflex cough test is a cough provocation test that stimulates the laryngeal expiratory reflex (LER). The LER is a series of expiratory coughs (cough epoch) without a significant preceding inspiration. This LER cough epoch caused 5 coughs (C5) with an average duration of 14.8 seconds. The following materials were used to perform the IRCT: a) vial containing a 20% solution of tartaric acid (Nephron Pharmaceutical, Inc; Orlando, Fla.); b) Pari LCD jet nebulizer (Bonn, Germany); c) oxygen flow meter; d) oxygen tank; and e) gloves and safety mask. The jet nebulizer was FDA approved for use in the U.S. and bore the CE Marking designating the manufacturer's compliance with Council Directive 93/68/EEC.

For the BSV study using the IRCT, the subject swallowed 50 ml. of thin barium solution immediately followed by administration of the IRCT. The BSV captured, at the level of the LES, a photomontage of the flow of barium, during the LER involuntary cough maneuver.

One subject also had both nasogastric and urethral fiberoptic, disposable catheters (#10 and #7 French catheters, respectively) with the pressure sensors placed at the level of the LES and IUS, respectively. Electromyography (DIG) electrodes were placed at the mid-axillary line of the T7-8 intercostal space and were used to confirm the inspiratory activity of the intercostal muscles. The Lumax TS Pro was used to record LES and IUS pressures and EMG activity. All urodynamic (UD) equipment and catheters used in this study were FDA approved for use in the U.S. and bore the CE Marking designating the manufacturer's compliance with Council Directive 93/68/EEC.

Figure 16B:
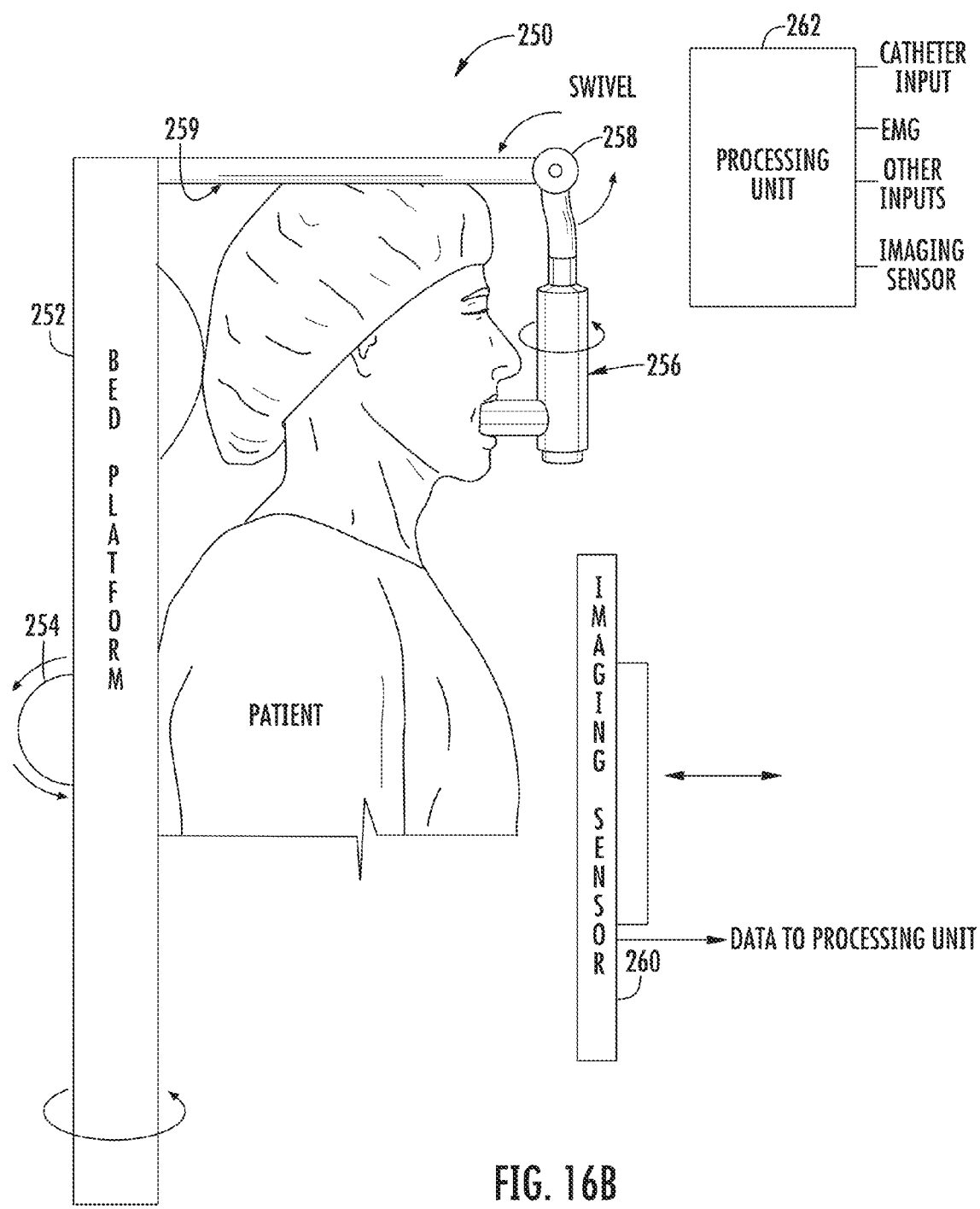
FIG. 16B is a view showing a system that includes a patient bed as a platform and imaging sensor for performing the methodology of FIGS. 14 and 15.

The one subject, who participated in the catheter portion of the study, was positioned in a semi-recumbent lithotomy position (approximately 60 degrees head up) such as using the structure shown in FIG. 16B as part of a quantitative analysis of the LES and IUS activity during inspiratory maneuvers. The subject performed deep and shallow breathing and breath hold maneuvers with simultaneous recording of LES and IUS pressures, and EMG intercostal inspiratory activity. The recordings were saved on the Lumax TS Pro for analysis of pressure waves and EMG activity.

Figure 5A:
FIG. 5A are images of the inspiration closure reflex (ICR) and showing the BFV sequences for barium swallow followed by deep inspiration that allows barium to enter the stomach.

BSV followed immediately by VC showed transient interruption of barium at the LES during inspiration, which released with expiration such as shown in the images in FIG. 5A. FIG. SB shows a nerve conduction pathway diagram for the inspiration closure reflex. The BSV sequence in FIG. 5A shows the barium swallow (left frame) followed immediately by deep inspiration (middle frame), which closes the LES and stops the flow of barium in the right frame. The expiration during voluntary cough releases the LES and allows barium to enter the stomach. The schematic diagram shows that the inspiration closure reflex (ICR) occurs with the activation of pulmonary inspiratory afferent fibers and their termination in the nucleus tractus solitarius (NTS). Centrally, the NTS influences the activity of the phrenic nucleus, dorsal motor nucleus of X and the sacral autonomic nucleus via descending pathways. This circuit regulates intrinsic sphincter tonicity during inspiration and expiration. This result was reproducible in all subjects.

Figure 6A:
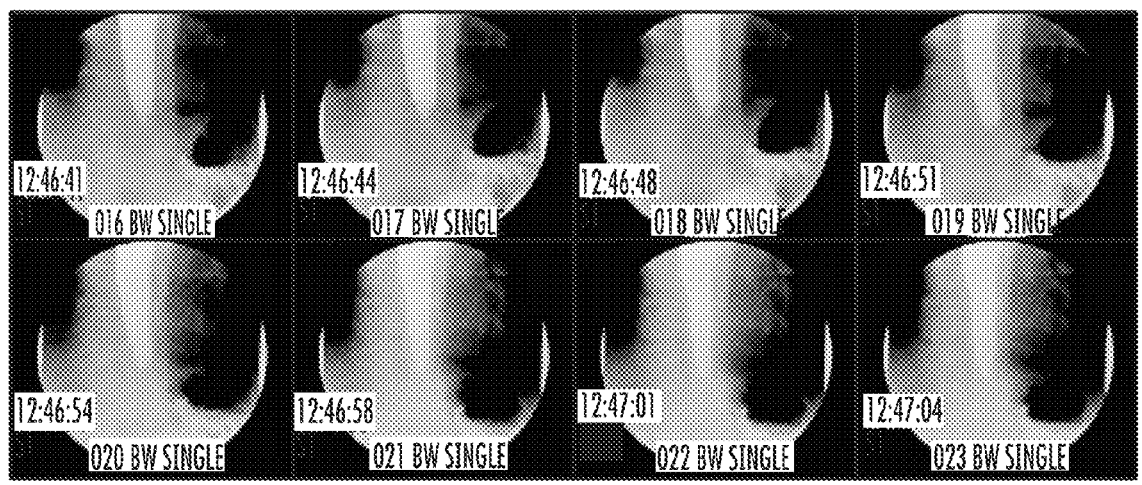
FIG. 6A are images showing a barium swallow during a breath-hold of a patient and depicting inspiration followed by barium swallow.
Figure 6B:
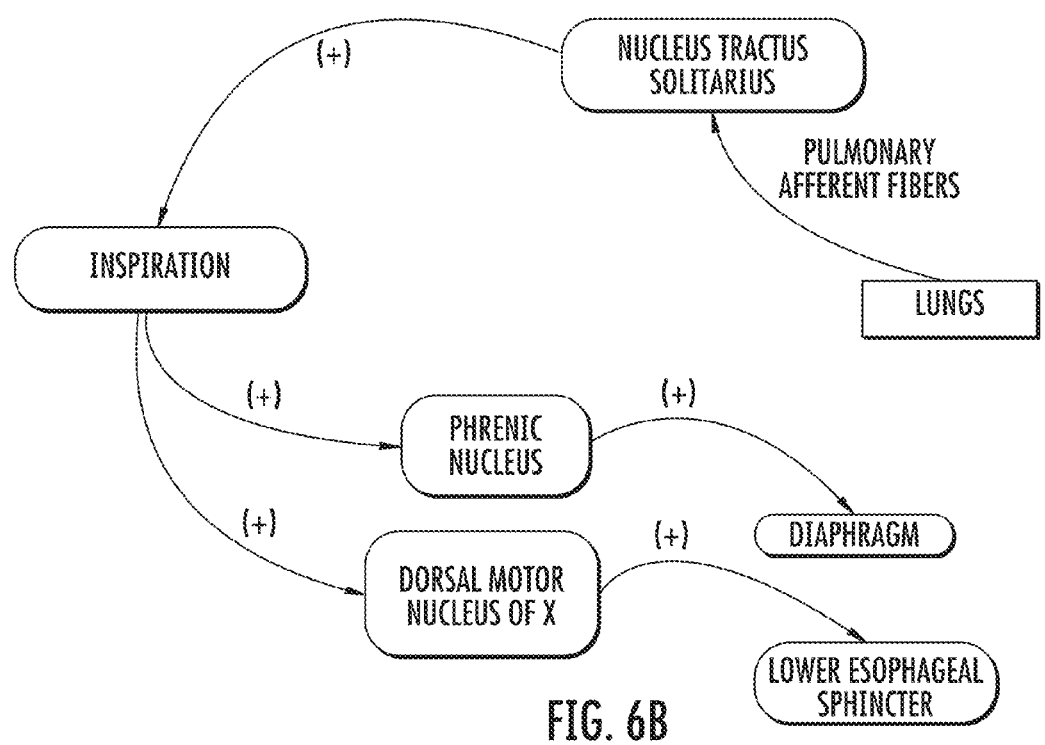
FIG. 6B is a nerve conduction pathway circuit diagram to show the physiology of the breath-hold as in FIG. 6A in accordance with a non-limiting example.

Deep inspiration and breath hold immediately followed by BSV showed complete interruption of barium at the LES during the entire breath hold event as shown in FIGS. 6A and 6B. The photomontage or images in FIG. 6A lasted 23 seconds, and the flow of the barium was completely interrupted at the level of the LES during this entire voluntary maneuver. This result was reproduced in all subjects.

FIG. 6B shows a nerve conduction circuit diagram for a barium swallow during the breath-hold. The ICR is demonstrated in the BSV photomontage images in FIG. 6A and the nerve conduction circuit diagram in FIG. 6B. The images depict the inspiration followed by swallowing barium. The LES closed with deep inspiration and remains closed during the entire duration of breath hold (greater than 20 seconds), which appeared to hold the barium above the LES. The barium stayed above the LES until expiration.

Figure 7:
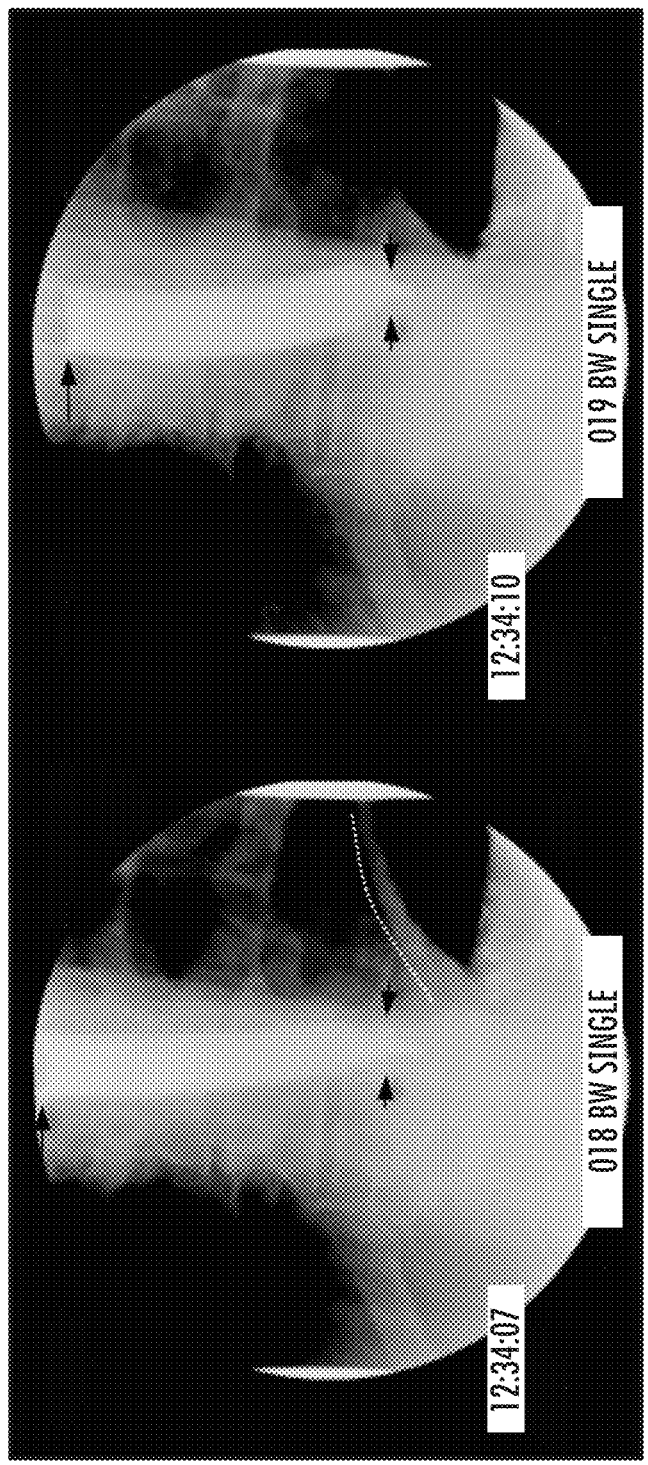
FIG. 7 are images showing the barium swallow during breath-hold in accordance with a non-limiting example.

In FIG. 7, at the region of the distal esophagus the diaphragm and proximal stomach were magnified using two consecutive images from a breath hold images as photomontages, which are separated by three seconds. The arrows at the proximal esophagus indicate the level of barium solution. The arrowheads indicate the level of the proximal portion of the LES and the barium solution. The barium in the distal esophagus showed a distinctive V-shaped tapering of the esophagus that suggests a cuff-like closure of the LES. The dotted line in FIG. 7 in the first image was placed above the diaphragm shadow, which was clearly inferior to the distal tip of the barium solution. This result was reproducible in all subjects.

Figure 8A:
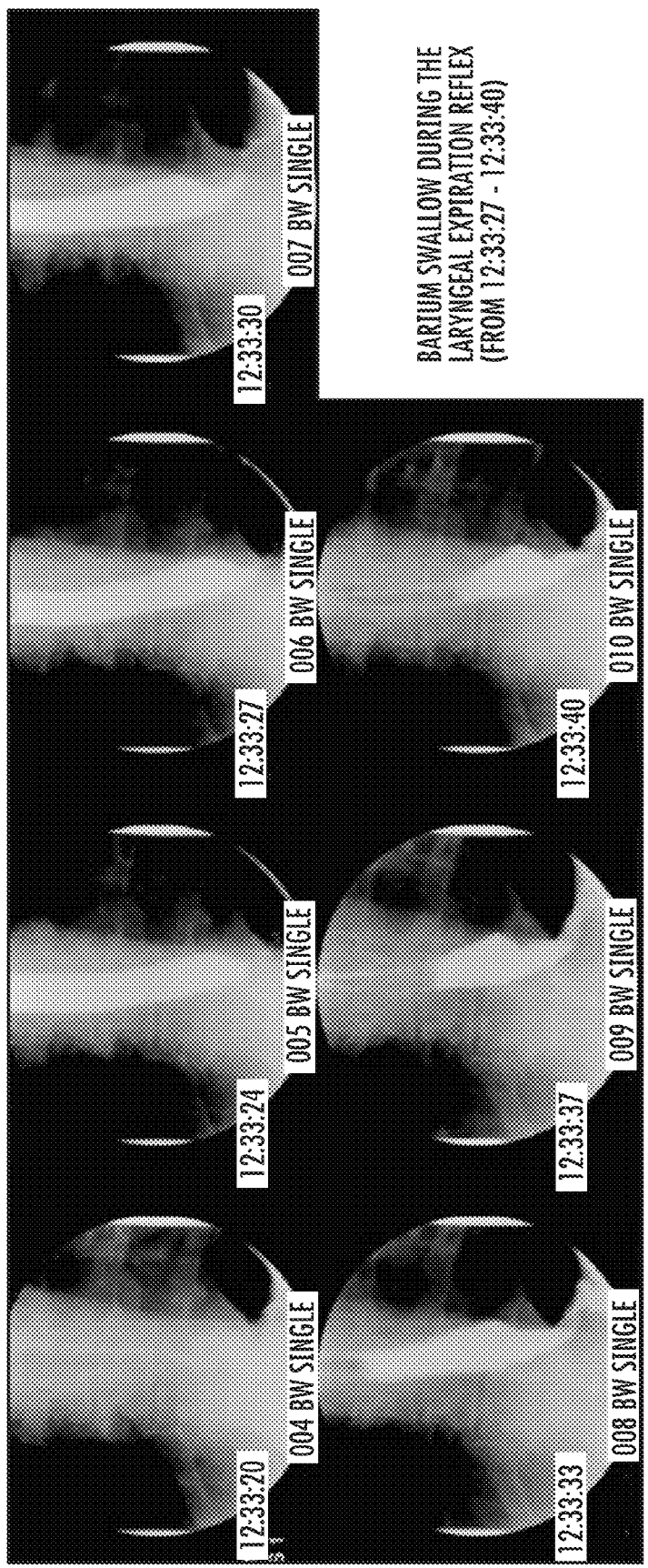
FIG. 8A are images showing the laryngeal expiratory reflex which the LES appear patent during the LER cough epoch in accordance with a non-limiting example.

BSV followed immediately by LER activation, using the IRCT, showed no interruption of barium at the LES during expiratory coughs as shown in FIG. 8A. The LER images as photomontages had a 13-second duration without an inspiration. The failure of the LES to close during the LER cough epoch with continuous barium flow was reproducible in all subjects.

Figure 8B:
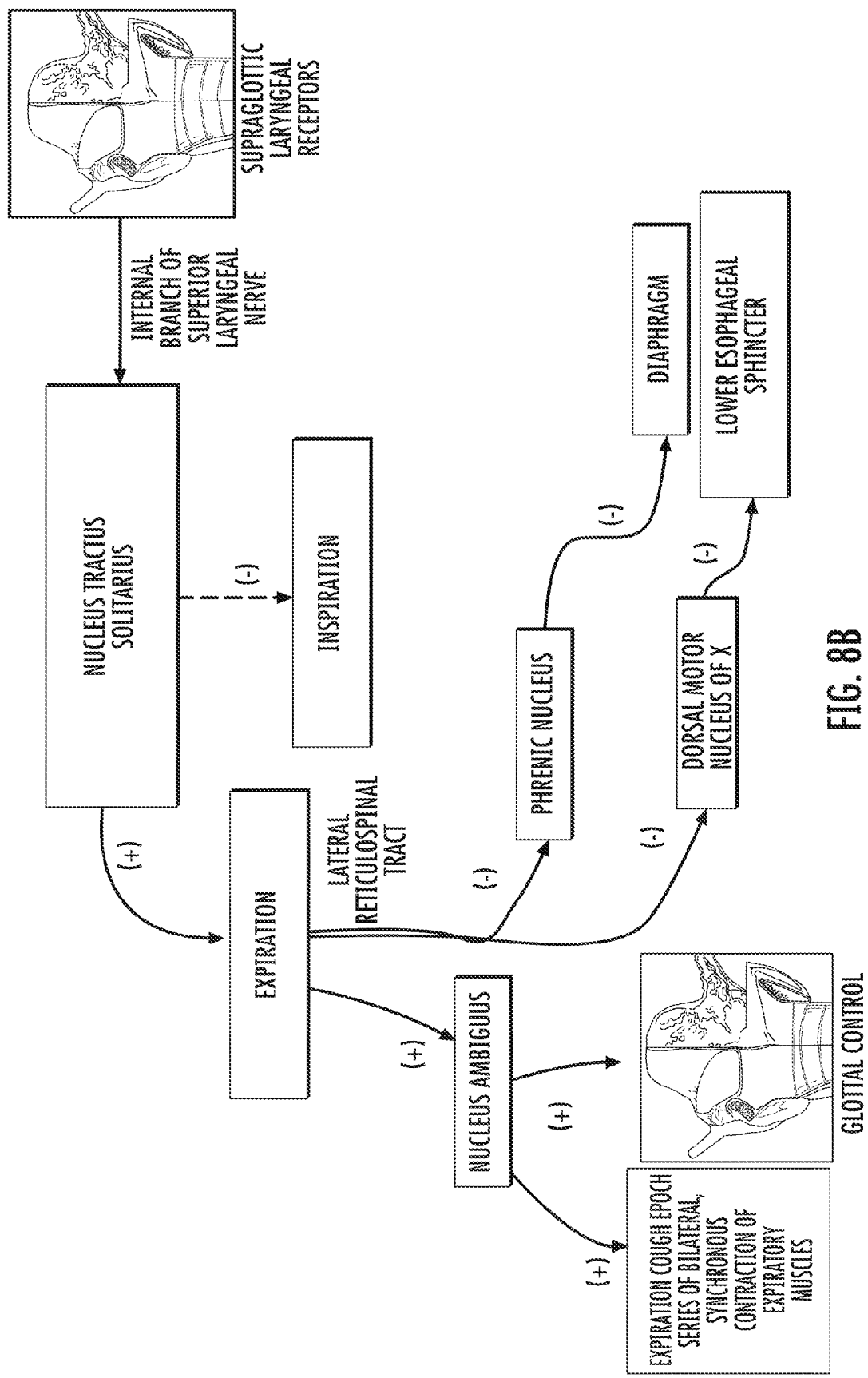
FIG. 8B shows a nerve conduction pathway circuit diagram of the stimulation of laryngeal receptors using the involuntary reflex cough test.

FIGS. 8A and 8B show the Laryngeal Expiratory Reflex (LER). The BSV photomontage in FIG. 8A was taken during an LER cough epoch and showed no closure of the LES. The LES appeared to be patent during the LER cough epoch, which allowed barium to flow into stomach. The primary function of the LER is to clear the upper airway when food or fluids have entered the laryngeal vestibule. The nerve conduction circuit diagram in FIG. 8B shows that stimulation of laryngeal receptors, using the IRCT, initiates a series of 5 expiratory "coughs" without inspiration, i.e., the LER cough epoch. The nucleus tractus solitarius influences the phrenic nucleus and dorsal motor nucleus of X, which innervate the diaphragm and LES, respectively. During an LER cough epoch, the LES is patent and inspiration does not normally occur.

Figure 9A:
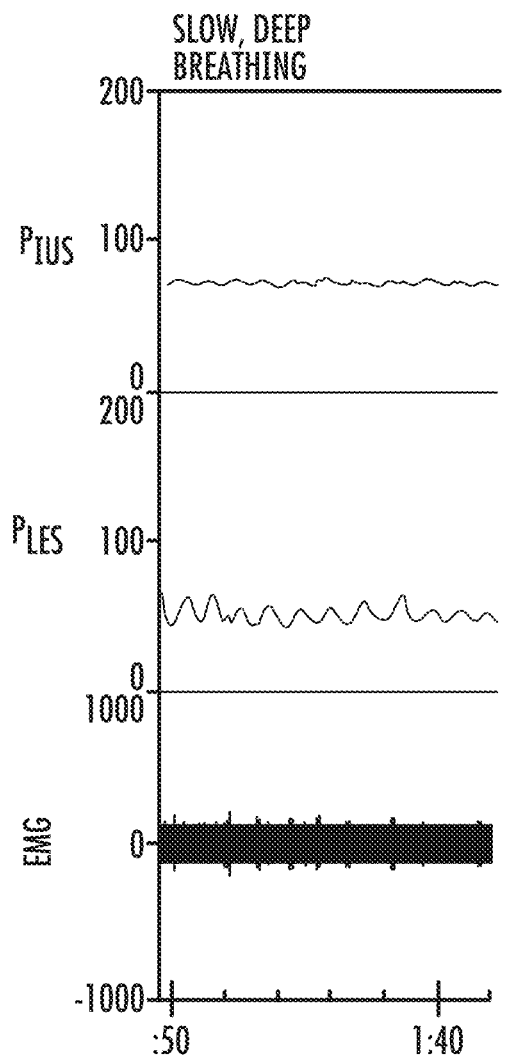
FIGS. 9A and 9B are graphs showing pressure recordings of the IUS and LES synchronizes with respiration in accordance with a non-limiting example.
Figure 9B:
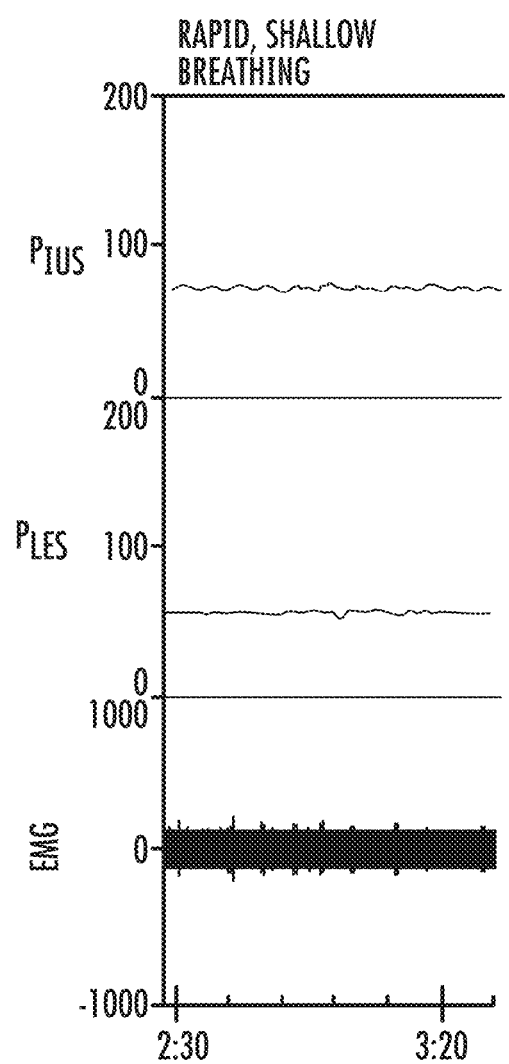

In the subject, who participated in the catheter portion of the study, the rapid closure and pressure elevation of the IUS after the initiation of each inspiration is shown in FIGS. 9B and 9B, which shows pressure recordings of the IUS and LES synchronized with respiration. Simultaneous pressure recordings of the IUS ($P_{IUS}$) and LES ($P_{LES}$) with respiratory EMG of the intercostal muscles at the T7-8 interspace demonstrated the activity of the ICR during breathing. During slow, deep breathing and rapid, shallow breathing, pressure waves indicated the respiratory rate and depth dependent variation.

Figure 10:
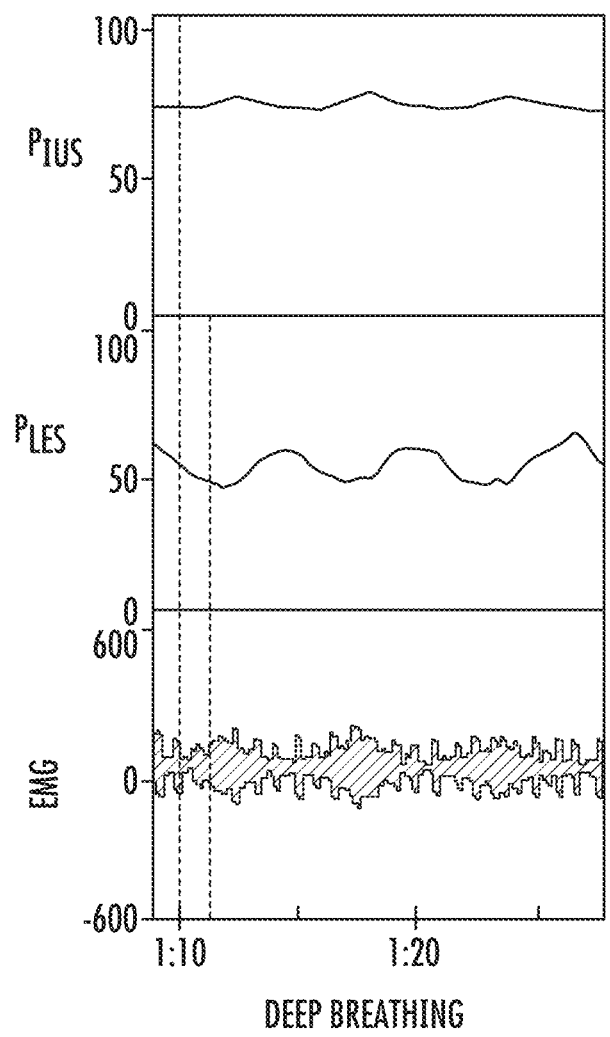
FIG. 10 is a graph showing relative latencies of the IUS and LES with deep inspiration and expiration in accordance with a non-limiting example.

FIG. 10 is a graph showing the latencies of the LES and IUS in relation to inspiration. The closure and pressure elevation of the IUS ($P_{IUS}$) and LES ($P_{LES}$) occurred after the initiation of inspiration. These closures (pressure waves) occur before the peak EMG activity, which is before the elevated IAP event in a voluntary respiratory maneuver.

Figure 11:
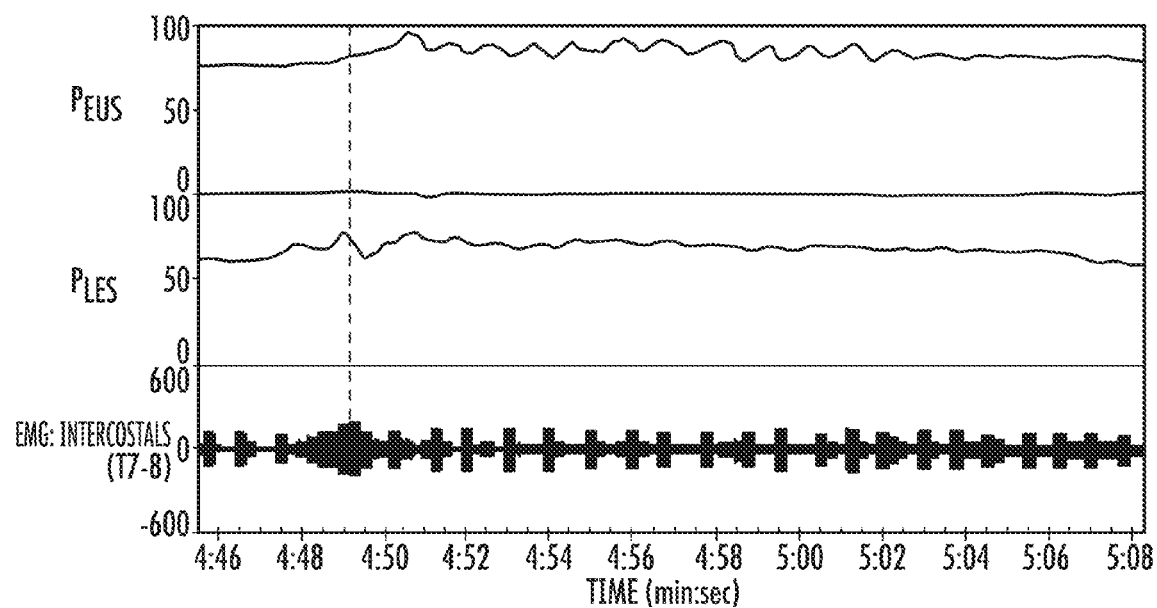
FIG. 11 is a graph showing the breath-hold with maintained pressure elevation in the LES and IUS in accordance with a non-limiting example.

Breath hold caused sustained pressure elevation in the LES ($P_{LES}$) and IUS ($P_{IUS}$) and corresponded to overlying voluntary contractions of the external urethral sphincter BUS ($P_{SUS}$) and pelvic floor musculature as shown in the graph of FIG. 11. During contractions of the EUS and pelvic floor muscles, the pressure of the LES ($P_{LES}$) remained relatively unchanged. There were no adverse events during this study. The graph in FIG. 11 shows breath hold with maintained pressure elevation in the LES and IUS. Breath hold caused sustained pressure elevation in the LES ($P_{LES}$) and IUS ($P_{IUS}$) and corresponded to overlying voluntary contractions of the external urethral sphincter EUS ($P_{KUS}$) and pelvic floor musculature. During contractions of the EUS and pelvic floor muscles, the $P_{LES}$ remained relatively unchanged.

Figure 5B:
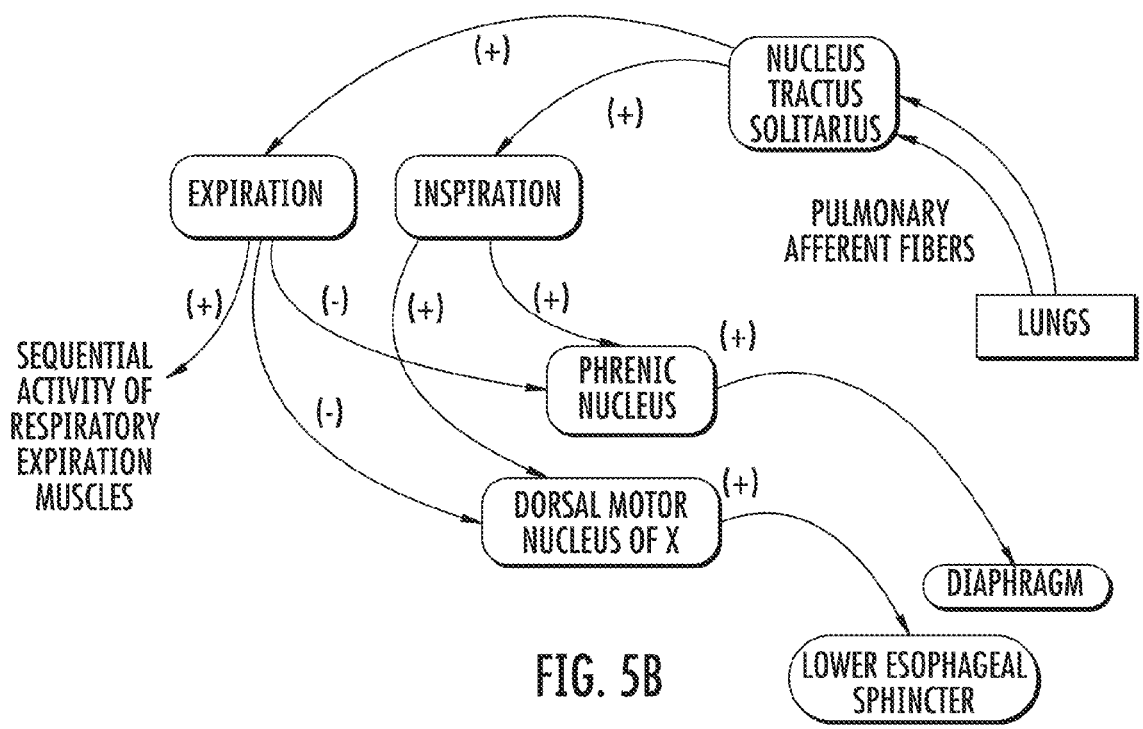
FIG. 5B is a nerve conduction pathway circuit diagram for the inspiration closure reflex (ICR) showing how intrinsic sphincter tenacity is regulated during inspiration and expiration in accordance with a non-limiting example.

Respiratory physiology. Bishop further identified expiratory muscle activation as an extension and component of the Breuer reflex. The studies described above suggest that the respiratory maneuvers for control of the closure and pressure of the IUS and LES during inspiration and release with expiration appear to be coordinated and synchronized with the rate and depth of inspiration. This is referred to as the Inspiration Closure Reflex as shown in FIGS. 5A and 5B.

In FIG. 8A, the BSV images as photomontages were taken during an LER cough epoch. The LES appeared to be patent during the LER cough epoch, which allowed barium to flow into stomach. The primary function of the LER is to clear the upper airway when food or fluids have entered the laryngeal vestibule. The LER appears to be inhibitory for inspiration and breathing and the associated reflex motor activations, which prevent closure of the LES during the involuntary cough epoch. Prevention of closure of the LES, during involuntary elevated IAP, may cause reflux of stomach contents in the presence of an incompetent gastric valve.

During slow, deep breathing and rapid, shallow breathing, pressure waves indicated the respiratory rate and depth dependent variation (FIGS. 9A and 9B). Simultaneous pressure recordings of the IUS ($P_{IUS}$) and LES ($P_{LES}$) with respiratory EMG of the intercostal muscles at the T7-8 interspace showed the influence of the Inspiration Closure Reflex (ICR). The amplitude of the catheter pressure waves was limited by the sensitivity of the fiberoptic transducers.

FIG. 10 shows an unexpected rapid closure and pressure elevation of the IUS ($P_{IUS}$) within one second, after the initiation of each inspiration. This delay may be explained by the fast conduction (30-60 m/sec) of the descending pathway in the spinal cord from the nucleus tractus solitarius (NTS) via the lateral reticulospinal tract to the neurons in the sacral autonomic nucleus at S2-4 of the spinal cord. The 25 cm long, unmyelinated, peripheral nerve component conducts at 0.5 m/sec, and takes less than one second to close the IUS. The LES closure was slightly delayed by approximately 1.5 seconds after the initiation of inspiration. This may be due to the different pathway from the NTS to the dorsal motor nucleus of X and a long peripheral, unmyelinated vagal nerve (50 cm) to the LES. Both of these closures (pressure waves) occur before the peak EMG activity, which is before the elevated intra-abdominal pressure (IAP) event in a voluntary respiratory maneuver, e.g., voluntary cough or a Valsalva maneuver.

Control of the LES may be due to upper and lower esophageal reflexes and diaphragmatic reflexes, i.e., a crural reflex. Some studies refer to transient relaxation or inhibition of the LES in association with swallowing obstructive sleep apnea, mechanical ventilation and a negative pressure body ventilator. In previous animal and human studies, respiration pressure "artifacts" in the LES and IUS were not noted or were electronically filtered by manometry instruments. There may be respiratory influences on intrinsic sphincter function that have not been adequately evaluated.

In animal models that require cannulation for respiration and/or positive mechanical ventilation, or in anesthetized animals or humans, the ICR may not have been observed. There has been some description of a "straining crural reflex" during the Valsalva maneuver that caused LES closure by esophageal-diaphragmatic reflexes. In human studies with a negative pressure body ventilator ("iron lung"), pulmonary inspiration afferent fiber activity was abolished during negative pressure inspiration in healthy, non-anesthetized subjects. This type of negative inspiration pressure ventilation and the absence of the subject's initiation of pulmonary inspiration afferent fibers abolished or significantly diminished manometric pressure of the LES during inspiration.

Figure 12A:
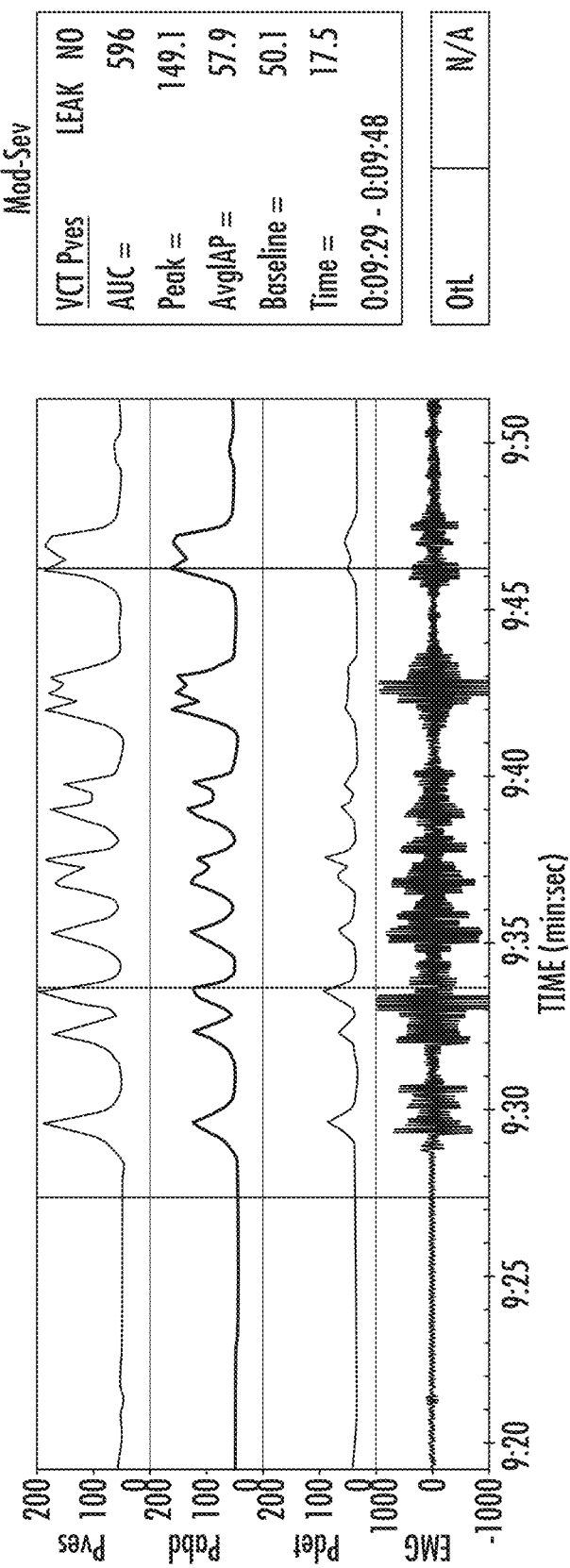
FIGS. 12A and 12B are graphs showing the urodynamic tracing of a series of forceful voluntary coughs in accordance with a non-limiting example.
Figure 12B:
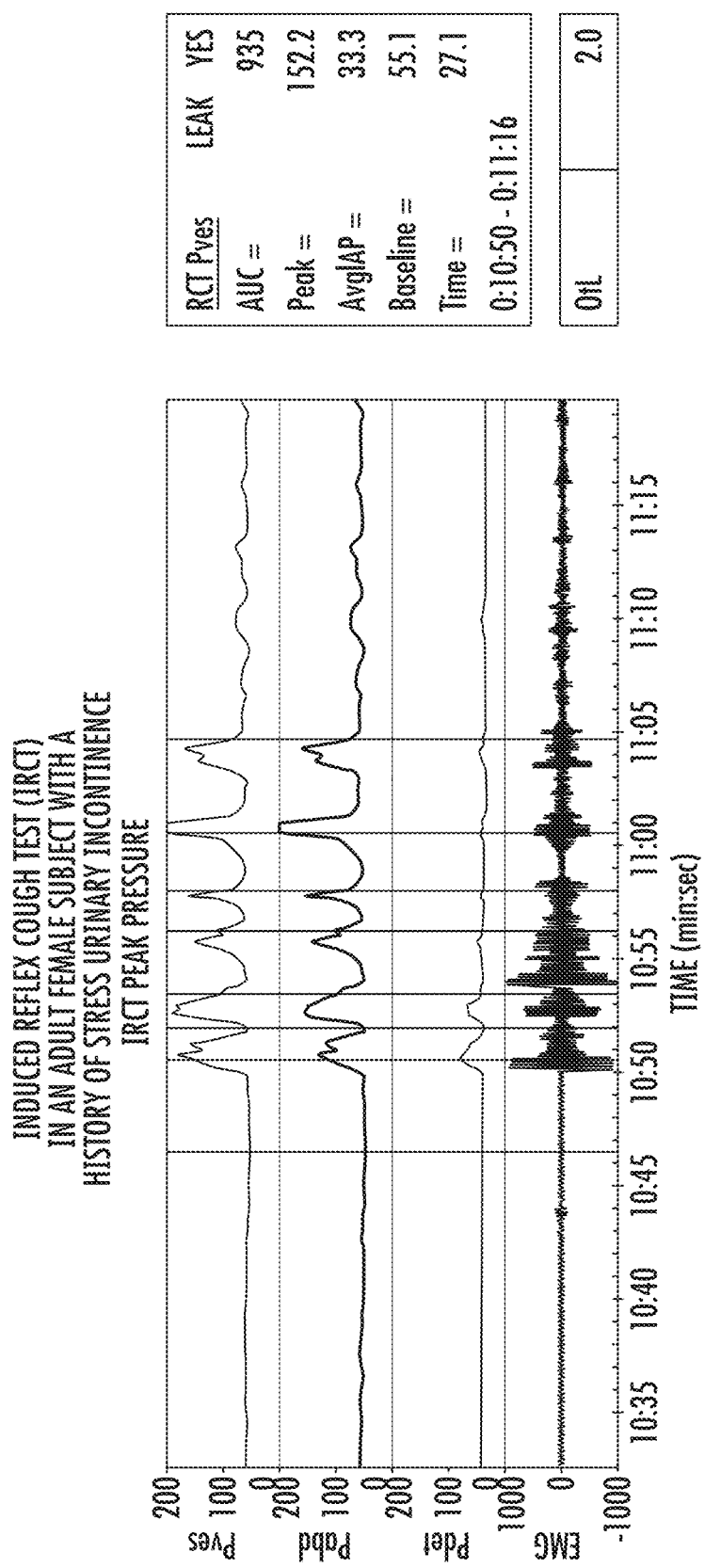

During breath hold, the elevated pressures of the IUS and LES were sustained during the entire breath hold event. The volitional contractions of the EUS and pelvic floor muscles were observed on top of the IUS pressure wave, which were not present on the elevated LES pressure tracing (FIG. 11). A clinical example of the ICR function is shown in the urodynamic (UD) tracing of a series of voluntary and involuntary coughs in a female subject, who has moderate/severe SUI as shown in FIGS. 12A and 12B. The subject had an almost two-fold increase in average IAP with the VC, and each cough was preceded by a deep inspiration (inhalation). During the VC as shown in FIG. 12A, it is believed that the deep inspiration that preceded VC activated the ICR and closed the IUS and resulted in a false negative result for SUI in this "moderate to severe" subject. During the involuntary cough epoch as shown in FIG. 12B, the IRCT UD tracing revealed multiple urinary leaks indicated by the marked vertical lines despite lower average IAP measurements compared to the VC.

These studies on IUS and LES activity, during respiratory events, suggest that if pulmonary inspiration afferent fibers are activated, these intrinsic sphincters close with every inspiration and release with every expiration. During voluntary maneuvers such as VC, Valsalva maneuver, or sneezing, these intrinsic sphincters release tonicity with expiration. The degree of intrinsic sphincter closure appears to vary with the rate, depth or volitional modification of inspiration. The LES and IUS pressure responses seen in this study appear similar to the "respiration artifacts" in other studies. It is possible that the IUS closure and pressure elevation related to inspiration could give a structural advantage at the neck of the urinary bladder to prevent incontinence as shown in FIGS. 12A and 12B. During inspiration, it is also possible that pulmonary inspiratory afferent fibers to the nucleus tractus solitarius (NTS) may co-activate the phrenic nucleus, dorsal motor nucleus of X (DMN) and the sacral autonomic nucleus as shown in FIG. 11. In FIG. 7, the LES closure and pressure elevation via the activation of the DMN may coincide with simultaneous activation of the diaphragm. This simultaneous activation may prevent hiatal herniation during elevated intra-abdominal pressure events such as Valsalva maneuver or pushing during labor and delivery.

There were a small number of subjects in the study, but the findings were method-dependent and reproduced in the four normal, healthy subjects for BSV and the one subject who had both the BSV and catheter studies.

Figure 13:
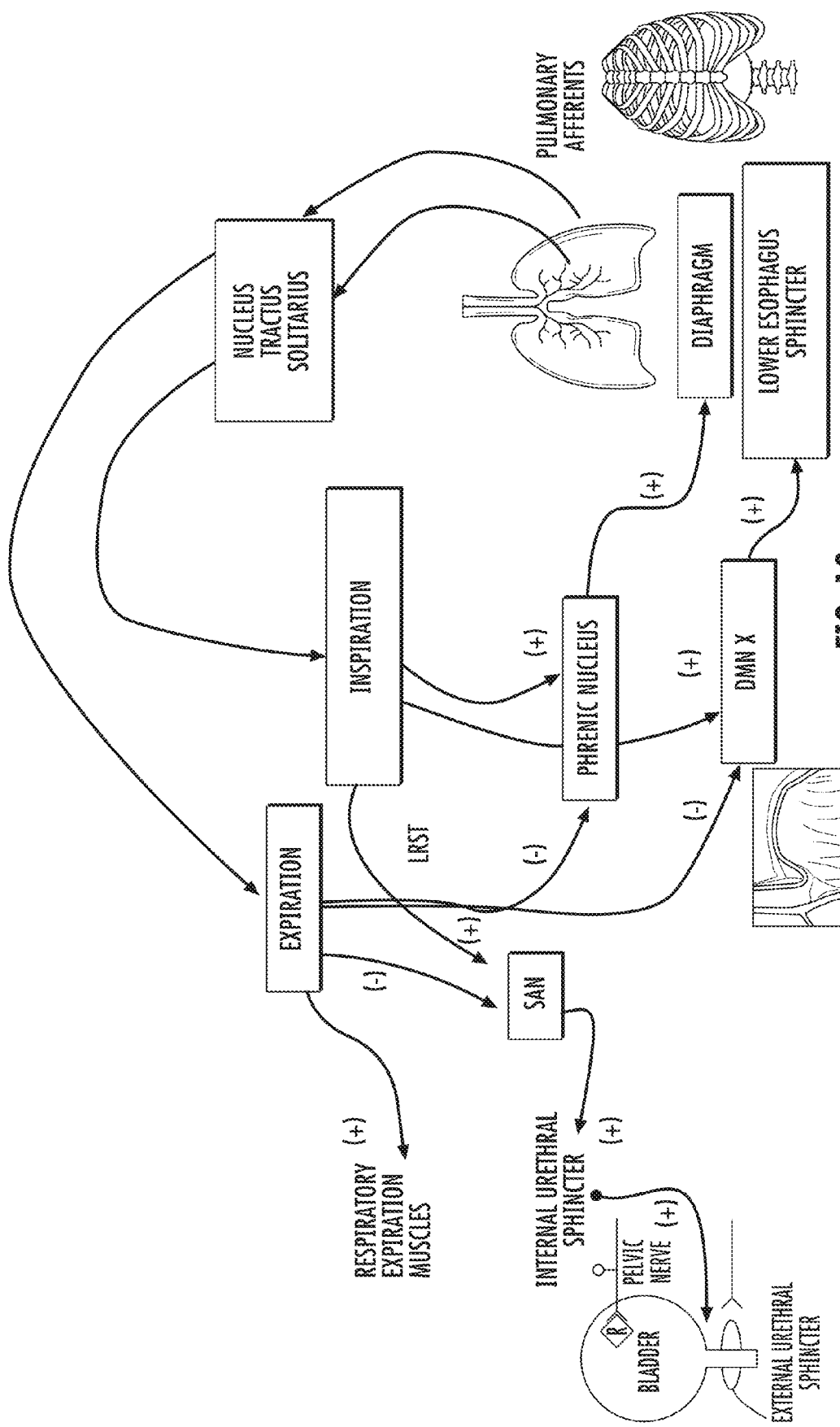
FIG. 13 is another nerve conduction pathway circuit diagram showing the inspiration closure reflex in accordance with a non-limiting example.

FIG. 13 is another nerve conduction circuit diagram showing the inspiration closure reflex. This diagram shows that the TCR occurs with the activation of pulmonary inspiratory afferent fibers and their termination in the Nucleus Tractus Solitarius (NTS). Centrally, the NTS influences the activity of the phrenic nucleus, dorsal motor nucleus of X and the sacral autonomic nucleus via descending pathways. This nerve conduction pathway circuit regulates intrinsic sphincter tonicity during inspiration and expiration.

As noted before, there is a control unit 34 as shown, for example, in FIGS. 1-4 that is operative to correlate changes in the intra-abdominal pressure and duration with the depth of inspiration and processes the data for direct microwire or indirect wireless transmission to stimulators of the smooth muscle of the internal urethral sphincter or striated muscle for the external urethral sphincter or anal sphincter. Thus, there is either trans-urethral or trans-vaginal implantation of muscle stimulators to the IUS, EUS and/or AS. It is possible to test the smooth muscle using intra-urethral electrodes or a pressure transducer catheter. One technique to test the maximal urethral closure pressure is to take the deepest breath possible. It is thus possible to treat stress incontinence with a stimulator and it is possible to address a deficit and identify and diagnose a deficit in the physiology by doing a maximal urethral closure pressure with inspiration and use an internal urethral sphincter transducer based on urodynamics.

There now follows detail of the disclosure from the incorporated by reference '121 patent.

Research on the LES and gastric valve indicates that problems arise with the gastric valve and there is a need for an available test to assess the competency of the gastric valve. In accordance with a non-limiting example, the involuntary maneuver, i.e., the involuntary cough test is employed.

Figure 14:
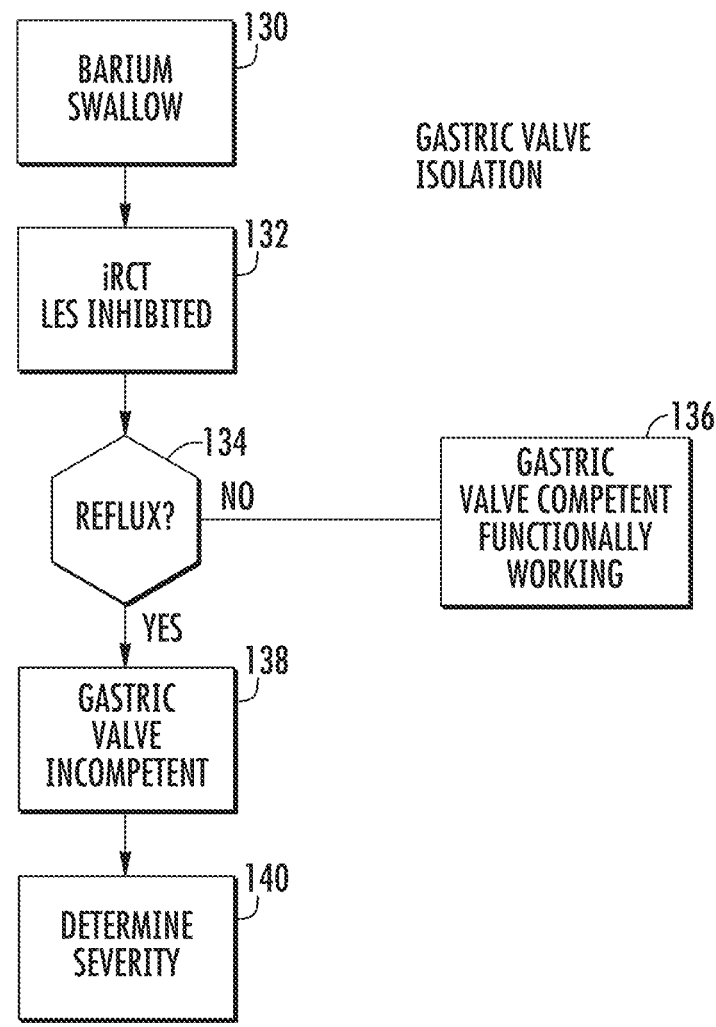
FIG. 14 is a flowchart illustrating a sequence of steps for isolating the gastric valve to assess its function in accordance with a non-limiting example.

FIG. 14 is a flowchart showing a general sequence of steps that can be used for isolating the gastric valve and determine if the gastric valve is competent and functioning adequately in one example. The kit shown in FIG. 16A can include the components for use with this methodology described relative to FIG. 14 and be used with the test system shown in FIG. 16B as explained below.

The sequence begins with a barium swallow (block 130) immediately followed by the involuntary reflex cough test, i.e., iRCT, such as by inhaling a chemo-irritant such as L-tartrate through a nebulizer in one non-limiting example (block 132). The involuntary reflex cough test isolates the gastric valve from the LES. A determination is made using video fluoroscopy, for example, if the reflux has occurred (block 134). If not, the gastric valve is competent and correctly functioning (block 136). If reflux occurs, then the gastric valve is incompetent and is malfunctioning since it is allowing the reflux (block 138). It is possible to determine the severity of the reflux (block 140), for example, by measuring the amount of reflux that occurs during the involuntary reflex cough epoch to estimate the severity of the malfunctioning gastric valve. This can be accomplished using enhanced fluoroscopy or using a Ng/Og catheter located at the LES or other location as later described to determine the extent of reflux.

Figure 15:
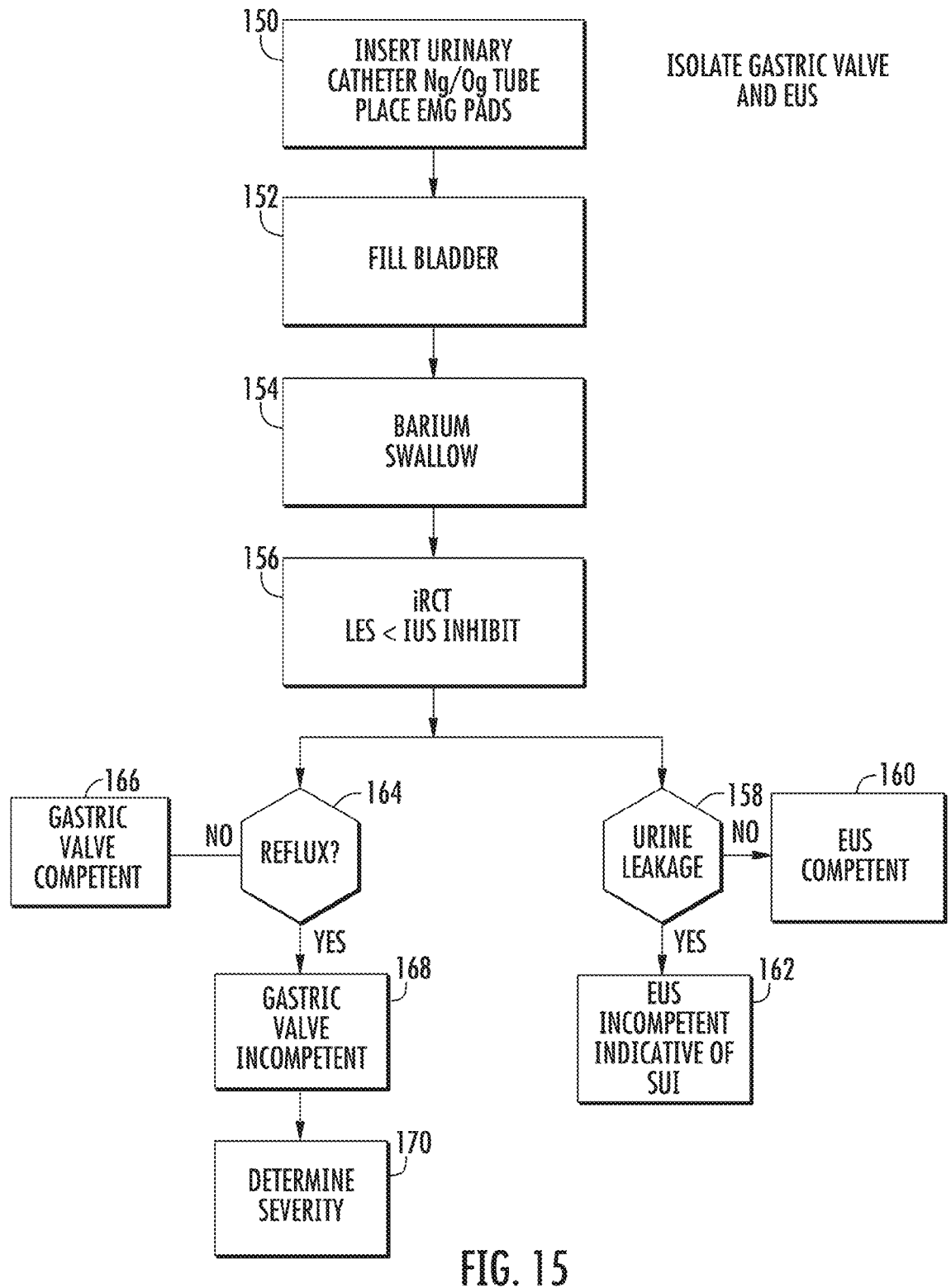
FIG. 15 is another flowchart illustrating a sequence of steps for isolating the gastric valve and external urethral sphincter to assess their function in accordance with a non-limiting example.

FIG. 15 is another flowchart showing a sequence of steps used for assessing the competency of the gastric valve and isolating the gastric valve from the LES and also isolating the external urethral sphincter from the internal urethral sphincter to determine stress urinary incontinence.

The process begins by inserting a urinary catheter in the patient with a pressure sensor in one example and a sensor located at the internal urethral sphincter in an example. The Ng/Og tube may include at least one sensor to be positioned at the LES and pH sensor at different positions. EMG pads can also be positioned at appropriate locations at the mid-axillary line of the T7-8 internal space (block 150). This could also include the paraspinals. The bladder is filled such as with saline solution (block 152). Barium or other contrast material is swallowed (block 154) and the involuntary reflex cough test induced (block 156). Two analysis paths are shown. A determination is made whether urine leakage occurred (block 158). If not, then the external urethral sphincter is competent and functioning adequately (block 160). If yes, then the external urethral sphincter leaked indicative of stress urinary incontinence (SUS) (block 162). Some determination of the severity of SUI or other problems can possibly be determined through analyzing the EMG results together with any intra-abdominal pressure that has been recorded during the involuntary reflex cough epoch. Reference is also made to the incorporated by reference applications for appropriate data and analysis regarding same. A determination is also made whether reflux occurred (block 164). If not, then the gastric valve is competent and functioning adequately (block 166). If yes, then the gastric valve is incompetent and is not functioning correctly (block 168). By using a Ng/Og tube or advanced imaging of the contrast agent, e.g., Barium Sulfate, it is possible to determine the severity of the reflux (block 170) such as measuring the amount of reflux at the LES and other locations within the esophagus.

A patient kit for assessing the gastric valve in conjunction with fluoroscopy and the EUG can be provided and an example is shown in FIG. 16A at 200. Items in this illustrated kit include:

1) Pneumoflex or USA Flex 20% tartaric acid in 3 ml unit dose vial 202;
2) 1000 ml Barium sulfate USP 204;
3) Ion Nebulizer or Crossfire Nebulizer 206;
4) Swivel adapter for nebulizer 208;
5) Protocol information sheet 210;
6) EMG pads 212;
7) Ng/Og tube or catheter 214; and
8) Urinary catheter 216.

The purpose of this kit 200 is to simplify the assessment of the gastric valve functioning (and/or external urethral sphincter) using the involuntary maneuver, i.e., involuntary reflex cough test (iRCT) to increase the intra-abdominal pressure to isolate the gastric valve while inhibiting the LES and, in some examples, isolating the external urethral sphincter. Evidence of gastric reflux can be observed directly using video fluoroscopy and evidence of SUI determined by isolating the external urethral sphincter to determine when there is urine leakage.

As shown in FIG. 16A, a handheld processing unit, such as described later relative to FIGS. 21 and 22, can be associated with the kit 200 and includes catheter inputs, EMG and other inputs.

It is well known that the gastric valve allows food to enter the stomach but prohibits reflux of gastric acid into the esophagus. As to the patient kit 200, one aspect is the use of the swivel adapter 208 for the nebulizer such that when the patient is turned over, the nebulizer through use of the swivel adapter can be more readily used by a doctor.

There have been a number of previous tests to distinguish different urinary incontinence problems including: 1) increasing the intra-abdominal pressure using a Valsalva maneuver; 2) having the patient jump up and down; or 3) generating one or more strong voluntary coughs. Through much clinical work, such as described herein and in the copending and incorporated by reference patent applications identified above, it has been determined that the involuntary reflex cough test (iRCT) activates the nucleus ambiguus, as compared to the voluntary reflex cough test.

FIG. 16B shows a patient examining system 250 for imaging any contract agent that can be used to implement the methodology as described. The patient examining system includes a bed 252 supported on a swivel/pivot 254 that is typically motor driven and allows the bed to be rotated and pivoted to place the patient in any predetermined position as inclined or turned over, if necessary. A nebulizer 256 is supported on a swivel adapter 258 and rotatable into various positions. The nebulizer 256 can be removable and could include a separate canister (shown by dotted lines at 215) or have nebulized medicine fed through a support arm 259 associated with the nebulizer and swivel adapter 258. Imaging sensor 260 can be positioned adjacent the patient for imaging barium or other contrast agent the patient has swallowed (or been forcibly administered depending on whether the patient is conscious). The processing unit 262 includes various inputs as described relative to the processing unit 218. The processing unit 262 can be a handheld processing unit or a fixed computer connected to the imaging sensor and various catheters inserted in the patient. The imaging sensor 260 in one example is a fluoroscopic instrument configured to image the contrasting agent. The imaging sensor is typically connected to the bed and moveable into a position adjacent the patient to image the contrast agent as it flows through the esophagus into the stomach during the involuntary reflex cough epoch. Data is transferred to the data processing unit where the data is processed and the amount of reflux that occurs during the involuntary reflex cough epoch measured to estimate the severity of the malfunctioning gastric valve in one example or the extent of the gastric valve adequate functioning. This could be accomplished, for example, by comparing a plurality of photomontages taken by the image sensor during the involuntary reflex cough test.

Figure 17:
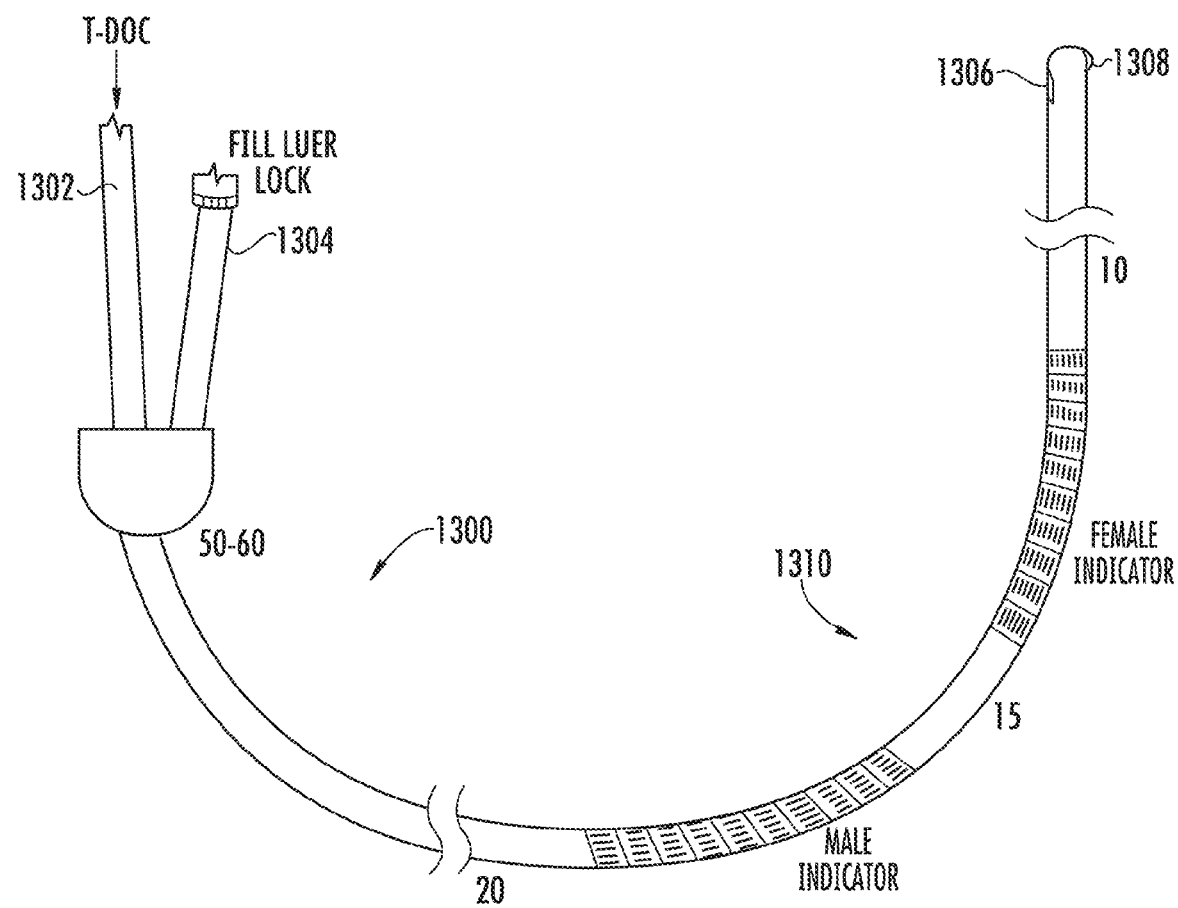
FIG. 17 is a simplified plan view of a catheter that can be used for urodynamic and medical diagnostic testing in accordance with a non-limiting example.

FIG. 17 is an example catheter 1300 that can be used in accordance with a non-limiting example. It is a urodynamic dual lumen catheter formed from a catheter body as an elongated tube with proximal and distal ends and preferably has a smallest external diameter that can contain two lumens within it. It is typically approximately 50 to about 60 centimeters in length. A first lumen 1302 can be used for monitoring bladder activity. In one non-limiting example, it contains a stylet/wire sensor that can be left within the lumen or used alone. A second lumen 1304 permits the filling port to instill fluid into the urinary bladder. The second lumen output is shown at 1306 and a sensor 1308 is positioned at the distal end. This catheter includes a luer lock end for rapid connection to infusion tubing or a syringe, and can accommodate rates of infusion up to 1,200 ml/hr via gravity flow or 15 ml/sec via manual installation.

The external surface of the catheter has a surface area that contains areas of indicators along its length shown generally at 1310 that operate as a urine leak detect device. These indicators 1310 change color when exposed to two components in combination in accordance with a non-limiting example. This color change can occur with a temperature about 30 degrees Celsius and the presence of urea in a non-limiting example.

The catheter 1300 can be used to evaluate bladder pressures at rest, empty, or with urine, filling with fluid during voiding. It is used to evaluate for urinary incontinence by detecting a minimal amount of urine loss during voluntary and involuntary maneuvers of the type as described before. The stylet sensor in one non-limiting example is used alone for pressure monitoring while presenting the least amount of disruption/distortion of the urethra and urinary sphincters. The stylet in another non-limiting example is packaged separately and inserted into an existing Foley catheter to measure pressure and function in one non-limiting example.

In one non-limiting example, the catheter is a dual lumen six French catheter of about 50 centimeters and includes the sensor 1308 and fill port at the second lumen 1304. It is inserted in a non-limiting example about 10 centimeters for a female bladder and 15 centimeters for a male bladder. The location of color change indicators 1310 for a female could be about 11-14 centimeters, and for a male, about 16-19 centimeters. In one non-limiting example, the urine pH range is about 4.6 to about 8.

It should be understood that the catheter is preferably a smaller diameter catheter and includes those catheters of 3 (three) and 4 (four) French. The smallest catheter possible is used as a urethral catheter and somewhat smaller than a standard ten (10) French catheter. It has been found that some patients have a tendency to leak with the larger catheter in place because of the size of the catheter or they become obstructed with that catheter in place. Smaller urinary bladder catheters are typically about 6 (six) French and used for neonatal infants. There are some PICC catheters (Peripherally Inserted Central Catheters) that are three (3) and four (4) French. These smaller catheters should be double lumen in this example. This system is not limited in size, but the smaller is advantageous.

The catheter, in accordance with a non-limiting example as described, can have a first lumen 1302 for a sensor probe 1308 and a second lumen 1304 for the filling with liquid. The sensor probe is a "T-doc" as used with an air-charged catheter for pressure sensing and air-charged pressure recording in one non-limiting example. It should be understood that this catheter can be used with or without filling the bladder, and advantageously used in urodynamic testing. The doctor, nurse or clinician does not have to personally bend down and view the urethra area to determine if there is leakage, which is an advantage in a clinical test. Different types of indicators 1310 as chemical indicators can be used.

Figure 18:
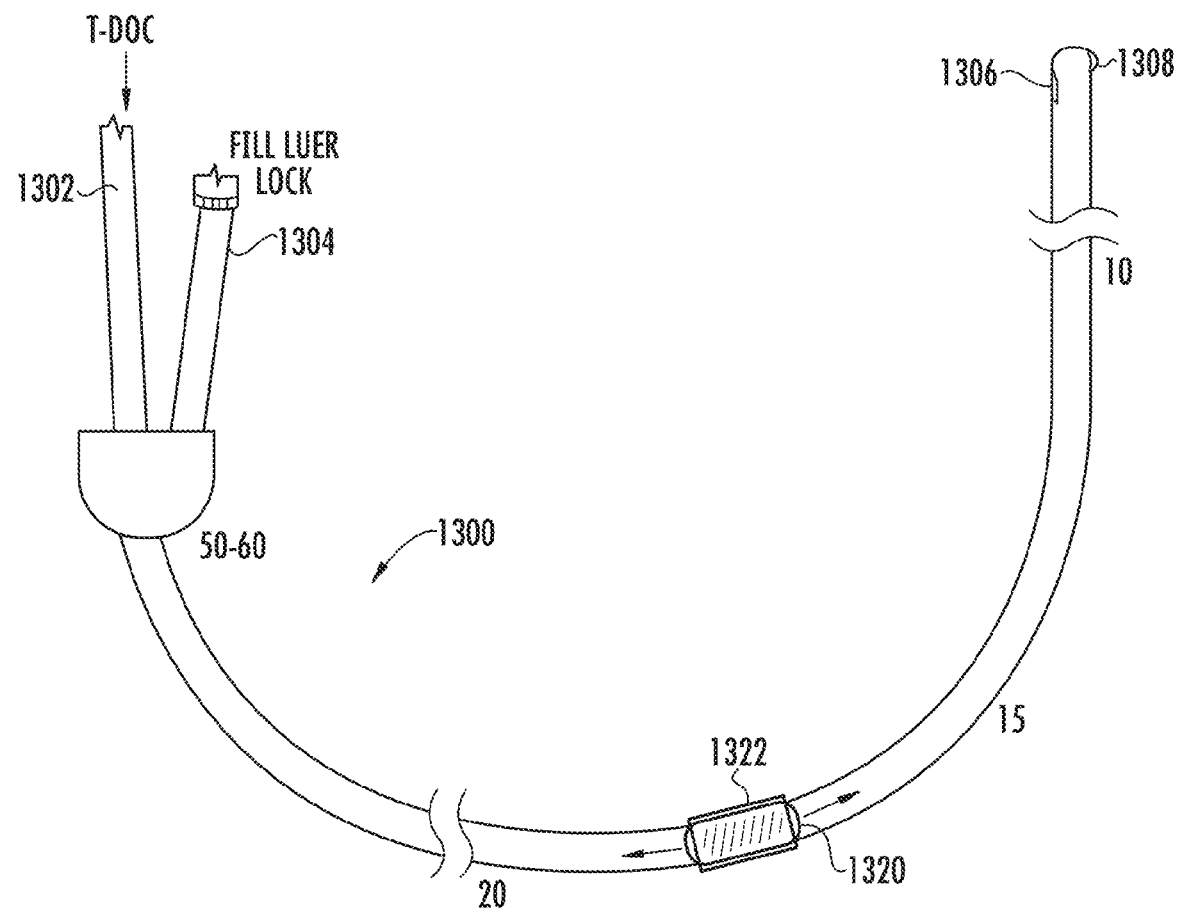
FIG. 18 is a simplified plan view of another example of a catheter similar to that shown in FIG. 17 that can be used for urodynamic and medical diagnostic testing in accordance with a non-limiting example.

In another non-limiting example such as shown in FIG. 18, the catheter includes a support ring 1320 such as a silastic ring that holds a urine-indicating pad or other enzymatic pad 1322 and is affixed to the catheter as a single unit wherein the catheter that measures the intravascular pressure. The silastic ring 1320 carries a color changing pad in this example instead of using color indicators 1310 positioned along the catheter surface as in the example of FIG. 17. This also provides for a urinary leakage indicator. The support ring 1320 slides on the catheter in one example. It is permanently affixed to the catheter, but adjustable in this example. A moisture indicating dye is used in an example on the pad 1322 positioned on the ring 1320. An example of a dye is disclosed in U.S. Pat. No. 4,327,731 as a moisture indicator, and in one aspect could be an enzyme catalyst.

Different types of pads or substrates could be used in combination with the support ring 1320 and moveable along the catheter. This combination catheter and the urine indicating sensor, in one example, are specific for use to determine an instance of stress urinary incontinence. It is possible, however, to add a balloon to this catheter similar to a Foley catheter such that the catheter remains in place. Two catheters are thus possible. For example, a specific catheter and urine indicator are used for stress urinary incontinence. It is also possible to add a balloon with the larger 14, 16, 18 or 20 French catheters as a larger size. A sensing system is included in this example. Added to this catheter is a channel for urine drainage, the sensor, and an indwelling balloon to keep it in place. The catheter, in one example, is used to determine whether the patient can protect their airway in conjunction with the involuntary reflex cough test (iRCT).

The cloth or pad 1322 is attached to the support ring 1320 and includes on the pad a regent that can be permanently attached. It can be a single use catheter for stress urinary incontinence (SUI) testing. It can be included within a test kit and includes the nebulizer (and the drug) for involuntary reflex cough testing as described before.

In one example, it is possible to have a catheter of about three (3), four (4), or five (5) or somewhat larger French that thread inside a regular Foley catheter with pressure measurement capability. The catheter that goes inside the urethra, such as a seven (7) French catheter, can go inside a Foley catheter. In one example, the balloon is part of the smaller catheter and measures or tests for airway protection in the technique as described before.

An enzymatic moisture detector can be used. Initially, any indicators or pad and ring could be covered before catheter use. When needed, the catheter is uncovered and moved into the proper position against the meatus. A first catheter is used with stress urinary incontinence and testing. Another catheter as a second or larger diameter catheter is balloon specific for reflex cough testing to measure intra-abdominal pressure in determination of airway protection.

In an example, temperature is used with the sensor and changes the sensor as an indicator. It is possible to use the presence of urea for sensing urine. One problem is in bladder testing. The bladder is often filled with saline water or other fluid that is not urine. If the indicator is specific to ammonia or urea, then it would not indicate adequately. Temperature is one advantageous solution and a material that is sensitive to temperature change of about 90 degrees is adequate. The fluid is inserted into the bladder and becomes warmer than room temperature. If there is leakage, it changes the color of the catheter even without the presence of urea.

The tip of the catheter can be placed into the urethra and the outside of the catheter includes the indicator. It changes color if there is leakage whether there is urine inside the bladder or just fill. It could change the color of liquid after it leaks. This could be an assurance against false positives such as would occur with perspiration from the doctor's or nurse's hands. If there is a second testing such as in surgery (and the patient hopefully fixed), a different color could be used. In an testing, the liquid is placed in the bladder in one example, but would come out a different color when it reacts with the sensor on the bladder near the meatus. This assures that one is viewing a leakage and not a false positive.

There is a possibility for measuring airway using the port in combination. The catheter can be small enough to go into a side port of a Foley catheter similar to a guide wire. Thus it is possible to take the catheter out if it is obstructing in some way and leave a guide wire. It is possible to remove the catheter and still have a guide wire or small catheter that has a sensor probe on the end. Instead of having a dual channel and having a tube inside a tube where one could do a fill around, it is possible to remove the outside tube that is blocking the urethra. It should be understood that the catheter (depending on size and pathophysiology of a patient) can either block the urethra or hold the urethra open, causing additional leakage. Specific catheter designs as described alleviate these problems. With the larger catheters, the larger catheter size is used to fill and is taken out. The inside tube (catheter) stays. A smaller four (4) French catheter has a dual channel, one for the pressure sensor and the other to fill 1200 millimeters an hour and is adequate to cover different possibilities.

Figure 19:
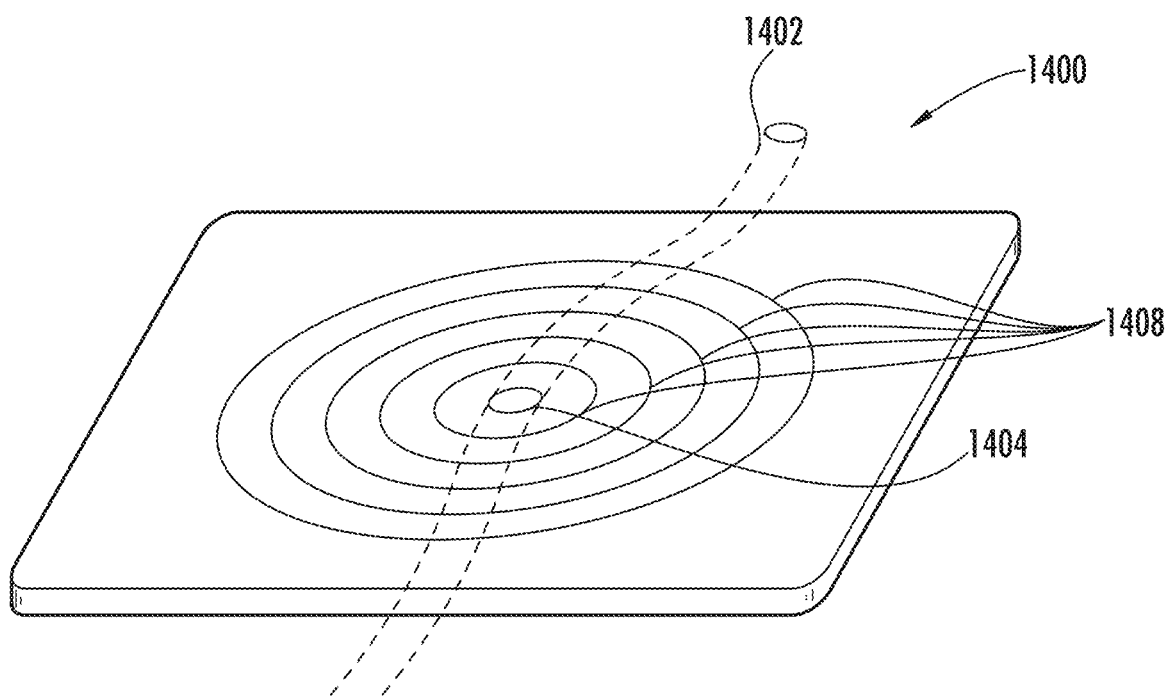
FIG. 19 shows a urinary continence pad that can be used with urodynamic catheters of FIGS. 17 and 18.

FIG. 19 shows an embodiment of a color changing urinary pad 1204 that can be used with a catheter such as described before. The color changing urinary incontinence pad 1400 is used in conjunction with a catheter 1402 and has a small relief cut-out (hole) 1404 in the middle of the pad where the catheter enters. The pad is placed against the underside near the urethra of a female typically and the catheter enters the urethra and extends through the hole in the center of the urinary incontinence pad for fluid flow and testing purposes. The pad could be taped to the underside in the crotch area. For example, when the involuntary reflex cough test is given and the catheter is inserted through the urethra, the patient is prone to leak urine in some examples. This pad includes concentric rings 1408 around the center catheter cut-out at preferred 10 millimeter intervals for a target area of 50 millimeters. In one non-limiting example, a nitrogen-ammonia (NH3) region is used to identify positively, the presence of urine on the pad. The target intervals of 10 millimeters each are used to determine how much leakage and incontinence occurs during, for example, a reflex or involuntary cough test as described before. The different concentric areas have different amounts of reagent in a non-limiting example or different reagents to allow different color changes at the spaced intervals depending on the amount of urine leakage.

The various Ng/Og devices as disclosed in the incorporated by reference U.S. Pat. Nos. 8,597,183; 8,602,987; and 8,597,184 disclose various Ng/Og devices that could be used or modified for use with the system and method in accordance with a non-limiting example. There now follows a description of the Ng/Og devices relative to FIGS. 20A-20E and 20E-20L and FIG. 20M without a balloon. It should be understood that different configurations of the Ng/Og device can be used with the system and method as described to analyze the LES relative to the GEV.

It is possible to package various components in kit as within a package or housing that includes a nebulizer for the drug as the tartaric acid in one example and a urinary incontinence pad and an EMG pad to be placed at a paraspinal. A kit could include the nebulizer and various catheters. The various components can be throw away components, except any processing device such as a handheld unit and could include any necessary connector leads that connect into the handheld device or wireless censored device.

Any catheter could include a wireless sensing device that is included in the kit in case wireless technology is used. Although a wireless sensing device could be separately connected to the catheter after the kit is opened, in one aspect, it is possible to include the wireless sensing device connected to any appropriate catheter such that when the kit is open, and the nebulizer removed, the catheter includes the wireless sensing device. The handheld device can be a separate device and the catheter used and wireless signals sent to the handheld device. After analysis and testing on a patient, the kit components such as the catheter and wireless sensing device, pads and nebulizer could be disposed of in the proper manner. It is possible that the EMG pads could connect into the wireless sensing device such that wireless signals are transmitted to the handheld device that includes the pressure readings and the EMG signals. Thus, the kit or system when removed would include the pressure sensing device with the attached leads and EMG pad and catheter that may be integrated together or separately removed and then connected to each other.

FIGS. 20A-20E show an example of the Ng/Og device that can be used or modified. This device could include a foam or air-filled esophageal cuff that is inflated using a separate lumen that is separate from the main lumen and any sump lumen. The device could include a pressure "bubble" at the end of the inflation lumen and could include a manometer connected for measuring pressure, for example, at the esophageal cuff and against the esophageal wall. Another lumen extending through the main body could be included with holes for suction just above the Lower Esophageal Sphincter (LES) to aid in suctioning reflux or emesis. This is advantageous for a surgery patient or acute neural or trauma patient. Details of such device are explained below.

It should be understood that stroke can cause Lower Esophageal Sphincter (LES) weakness. The urology studies discussed above address that determination. The LES is weakened by stroke and other factors, including the initiation of an involuntary cough such as through the iRCT test. The Ng/Og device, in accordance with a non-limiting example and described in detail below, acts as an esophageal reflux protection device to protect the patient from the weakness of the Lower Esophageal Sphincter (LES). It is known that cough causes reflux, which causes more cough. This is a vicious cycle. This device allows blocking of emesis and prevents reflux associated with pneumonia and anesthesia or other functions affecting neural patients. The NG/OG device shown in FIGS. 20A-20E can be used when there is microscopic reflux or massive emesis, which both can cause pneumonia. In some instances, it may be possible to use a Foley catheter and a smaller catheter tube and the Foley catheter left in place and a smaller catheter pulled after cough is measured.

It should be understood that the esophagus is about 25 centimeters long. It is a muscular tube with a diameter of about 2 centimeters average. It tracks the vertebral column curve and descends through the neck and posterior medistinum and passes through the esophageal hiatus in the right crus of the diaphragm to the left of the median plane at the level of the T10 vertebrae.

The esophagus enters the stomach at the cardial orifice to the left of the midline at the level of the 7th left costal cartilage and T11 vertebra. The abdominal part of the esophagus extends from the esophageal hiatusis in the right crus of the diaphragm to the cardial (cardiac) orifice of the stomach. This area is only about 1.25 cm long.

Food passes through the esophagus rapidly because of the peristaltic action and is typically not dependent on gravity. The esophagus is attached to the margins of the esophageal hiatus in the diaphragm by the phrenicoesophageal ligament, an extension of the inferior diaphragmatic fascia. This ligament permits independent movement of the diaphragm and esophagus during respiration and swallowing. The esophagogastric junction lies to the left of the T11 vertebra on the horizontal plane that passes through the tip of the xiphoid process. Immediately superior to the esophagogastric junction, the diaphragmatic musculature forming the esophageal hiatus functions as a physiological inferior (lower) esophageal sphincter (LES) that contracts and relaxes. The sphincter mechanism for the LES is typically efficient in preventing reflux of gastric contents into the esophagus based on radiological studies. The lumen of the esophagus is normally collapsed superior to this level to prevent food or stomach juices from regurgitating into the esophagus when an individual is not eating.

Barium fluoroscopic studies of the esophagus normally show three constrictions of the esophageal lumen due to impressions from adjacent structures. These are possible locations for placing a device reflux analysis and GERD treatment.

A first constriction is the cervical constriction (upper esophageal sphincter). The superior aspect of the esophagus is the pharyngoesophageal junction, and is approximately 15 cm from the incisor teeth. The cricopharyngeus muscle creates this cervical constriction, which is located at approximately the level of the sixth cervical vertebra.

A second constriction is the thoracic (broncho-aortic) constriction. The arch of the aorta and the left main bronchus cross the esophagus and create esophageal constrictions as seen on anteroposterior and lateral views, respectively. The constriction caused by the arch of the aorta is 22.5 cm from the incisor teeth and the constriction formed by the left main bronchus is 27.5 cm from the incisor teeth.

A third constriction is the diaphragmatic constriction. The esophageal hiatus of the diaphragm is approximately 40 cm from the incisor teeth and forms the diaphragmatic constriction. This is at the level of the lower esophageal sphincter.

The presence of these constrictions is important when placing the device as described with the esophageal cuff, which would help prevent the reflux of gastric contents into the upper esophagus and pharynx. The placement of the device in one example is suggested inferior to the broncho-aortic constriction (27.5 cm from the incisor teeth), but superior to the diaphragmatic constriction at 40 cm from the incisor teeth. The device typically should not be placed in regions of the esophagus with pathological involvement of the esophagus.

Figure 20A:
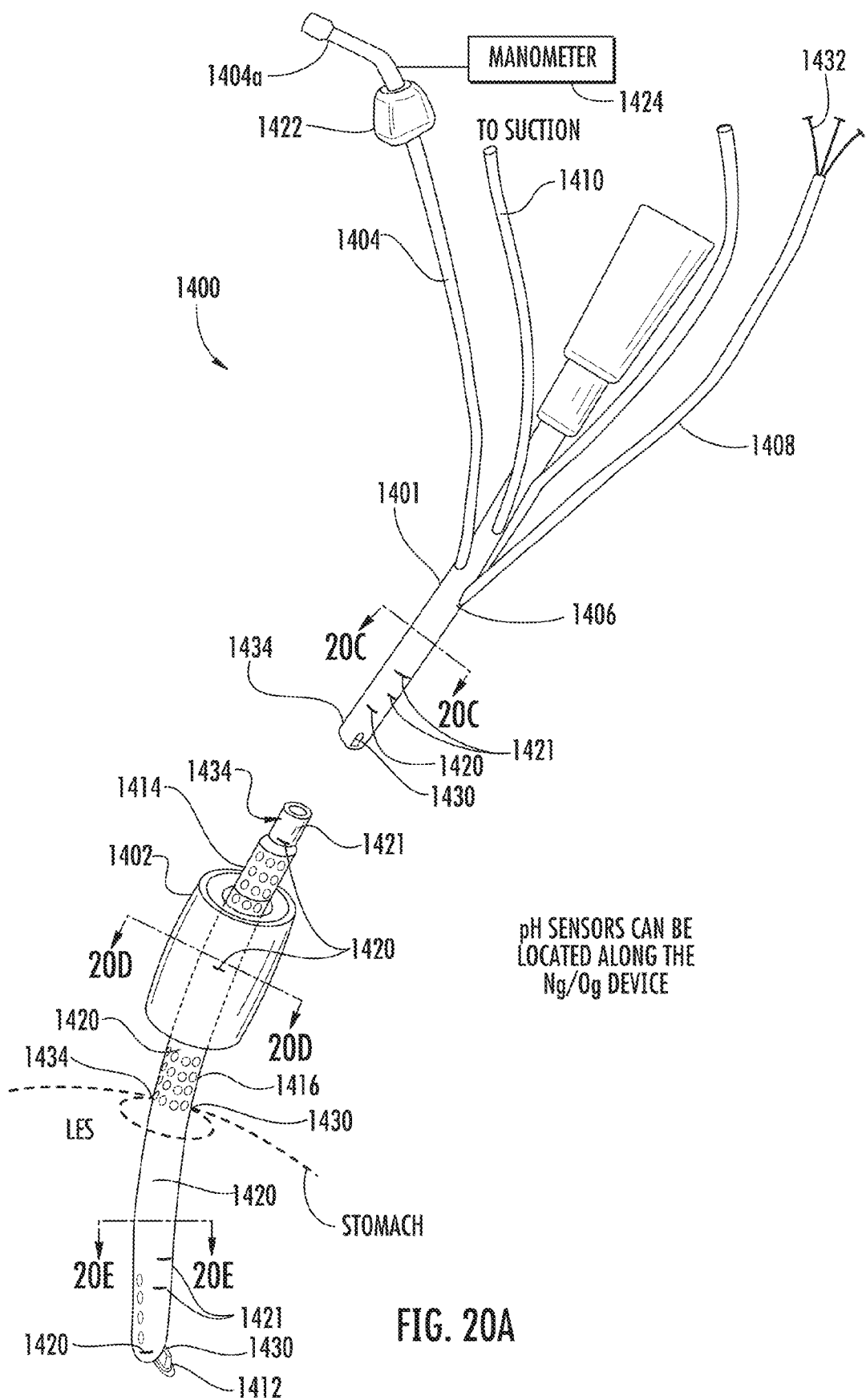
FIGS. 20A-20E are general environmental views of an oral-esophageal and gastric device or catheter (Ng/Og device) with an esophageal cuff (or balloon) to reduce or diminish gastric reflux and/or emesis in surgical/neurological and/or trauma patients and which can be used with the disclosed system and method in accordance with a non-limiting example.
Figure 20B:
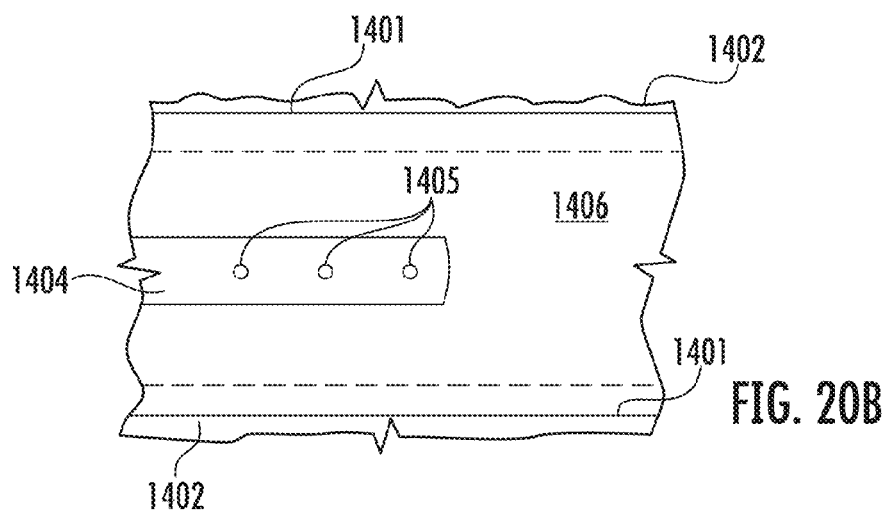
Figure 20C:
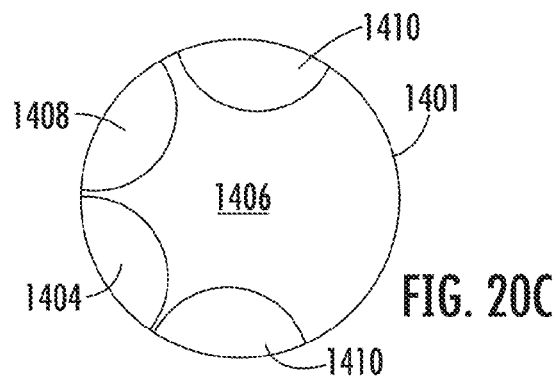
Figure 20D:
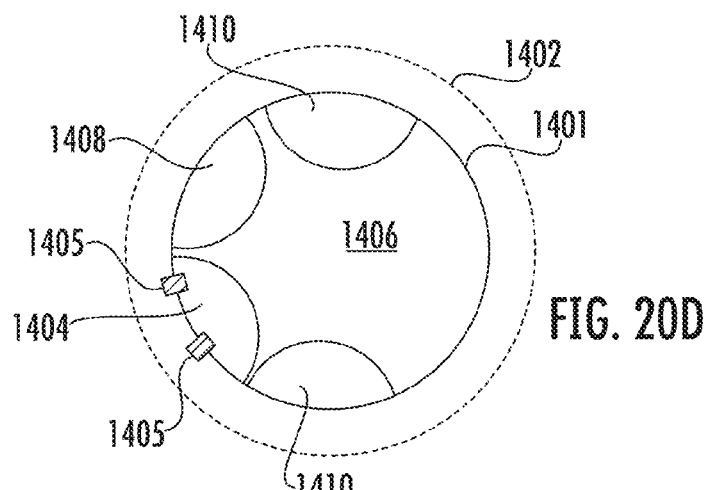

FIGS. 20A-20E show the device in plan and sectional views and indicated generally at 1400, and includes a main device body 1401 and a foam or air-filled esophageal cuff 1402 with a separate inflation lumen 1404 for inflation and deflation as shown in FIGS. 20B-20D. FIG. 20B shows the cuff 1402 in deflated position and FIG. 20D shows the cuff inflated. Air channels 1405 connect the inflation lumen and the cuff as shown in FIGS. 20B and 20D. The section view in FIG. 20B shows the termination of the inflation lumen.

Figure 20E:
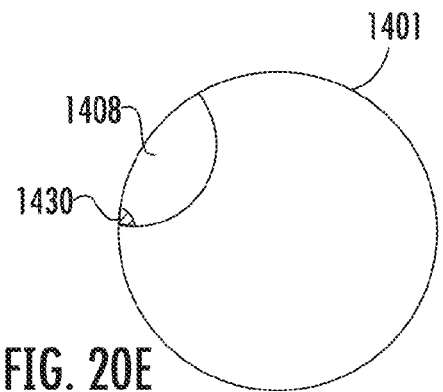
Figure 20F:
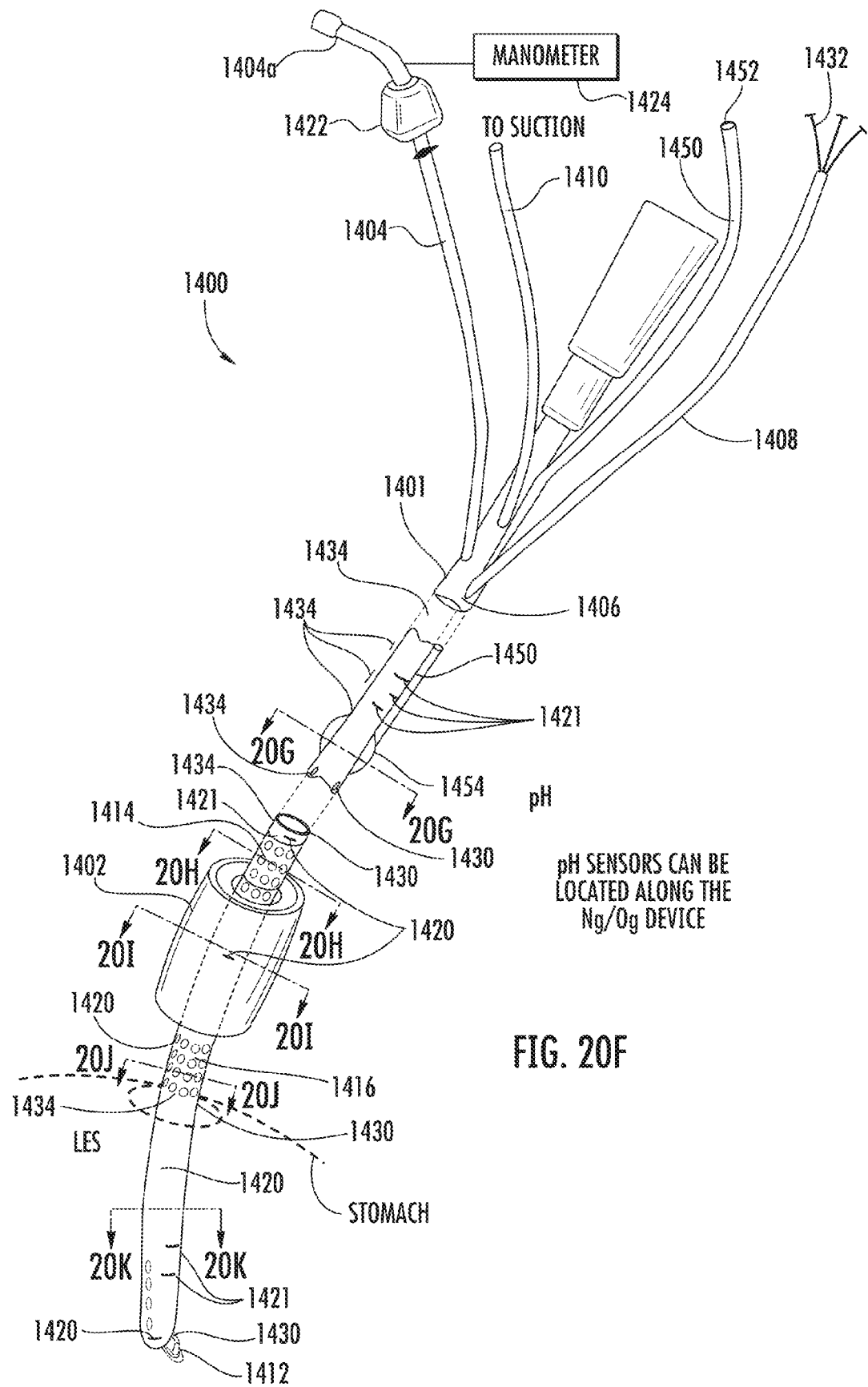

The tip of the device is shown positioned in the stomach, which is shown schematically in FIG. 20A. FIG. 20C is a cross-section taken along line 20C-20C of FIG. 20A. FIG. 20D is a cross-section taken along line 20D-20D of FIG. 20A. FIG. 20E is a cross-section taken along line 20E-20E of FIG. 20A. In these cross-sections, the various lumens are shown, including the main lumen 1406, the sump lumen 1408, the inflation lumen used for inflating the cuff, and any suction lumens 1410 that are used for suction above the LES. The sump lumen 1408 is connected to a sump port 1412 (FIG. 20A) at the end of the device 1400. Drainage holes 1414 positioned in this example above the cuff 1402 allow secretions to pass into the device. These drainage holes could be formed as suction holes such as in the example device described relative to FIGS. 20E-20G and connected to any suction lumens. Suction holes 1416 are positioned below the cuff 1402 and connect to the suction lumens 1410 to permit emesis and reflux to be suctioned. The drainage holes could also connect to the suction lumen 1410 as noted before. In a non-limiting example, the drainage holes and suction holes include one-way valves to allow emesis to enter, but not return.

This device typically forms as a nasogastric or orogastric tube with a Salem sump port 1412 and an additional port 1404a for air entry and exit to and from the esophageal cuff, allowing a high volume and low pressure cuff 1402 as illustrated and supplied by the inflation lumen 1404. The device can come in variable sizes and lengths depending on patient needs and requirements and typically a standard size for use depending on patients. The device can be used for gastric enteral feedings or gastric decompression resulting from the use of the Salem sump port 1412. The device typically includes radio-opaque markings 1420 throughout the length of the tube as illustrated for measurement and placement. Measured markings 1421 as indicia can be positioned in one example along the length of the tube together with a color changing material or pit sensitive material and at the bulb/cuff for measuring emesis, etc.

The cuff 1402 that is shown is in its inflated position in FIG. 20A and is high volume and low pressure and can be inflated with air. It could be foam filled or a combination of both air and foam. Inflation and deflation is through the leur lock port 1404a that includes the pressure inflation balloon 1422 adjacent thereto. The inflation balloon 1422 allows for a tactile cuff and a gross pressure check such as through a manometer 1424 attached thereto. The leur lock port 1404a attaches in one example to a manometer for actual cuff pressure measurement. The cuff 1402 easily collapses for emergency removal or self-extubation without causing damage to surrounding structures of the esophagus, hypopharynx, pharynx, and oral cavity. The cuff is kept inflated below the capillary pressure of the esophageal wall to prevent ischemia that is typically about 7-8 centimeters (cm) water. As indicated before, there are radio-opaque markings 1420 to aid in device placement confirmation. The cuff can be radio-opaque to aid its placement. The upper portion of the esophageal cuff is typically mildly concave to promote secretion to flow towards openings as drainage holes 1414 (or suction holes if formed as such) in the device in this example. An upward force, such as emesis or vomit on the lower portion of the cuff, expands the cuff outwards towards the esophageal wall to control gastric contents from entering the hypopharynx. The inflation/deflation port 1404a can be a different color than the openings for the sump lumen, the suction lumen and the main lumen. The inflation/deflation port 1404a in one example is fitted with the standard leur lock cap and the inflation/deflation port can be labelled with the term "esophageal cuff" to aid practitioners or identifying.

The Ng/Og device is typically inserted through the nasal cavity or through the oral cavity and enters into the stomach. Measurements can be made from the lips or nares to the TMJ (temporomandibular joint) and to about four-finger breadths to sub-xyphoid. When the esophageal cuff 1402 is deflated, a water-soluble lubricant can be applied to the end of the device to aid insertion. This NG/OG device is inserted in a manner similar to an OGT (orogastric tube) or NGT (nasal gastric tube) (NG/OG tube) with the clinician or nurse using the placement radio-opaque markings 1420 to position the device over the lungs and stomach. Once it is in position, it is possible to use auscultate placement by listening to sounds and using an air bolus into the tube and attempt to aspirate gastric contents from the tube. The tube is secured and its placement confirmed by x-ray (using the radio-opaque markings 1420 for help) with the preferred location inferior to the broncho-aortic constriction while superior to the diaphragmatic constriction. The cuff 1402 is inflated through the inflation lumen 1404 and the cuff pressure typically measured with the manometer 1424. The main lumen 1406 as part of the device body 1401 will have low continuous or intermittent suction and may also be used to administer external feedings.

The device 1400 is advantageous for use such as with the neurologically impaired who are at risk for aspiration of gastric contents, including those suffering from a cerebrovascular accident that could be ischemic, thrombotic or hemorrhagic. The device can be advantageously used for non-traumatic brain injury including incephalopathy or intracranial tumor/mass. The device can also be advantageously used when there is traumatic brain injury and general anesthesia, including intra-operative or post-operative, for example, when the patient is neurologically impaired and may not be able to protect their airways. The device is also advantageously used with neurological disorders including Parkinson's Disease, amyotrophic lateral sclerosis and bulbar impairment, myasthenia gravis, and multiple sclerosis. The device is advantageously used with compromised consciousness such as through alcohol intoxication, drug overdose and psychiatric disorders. Indications for use also include gastric decompression because of the use of the sump port and gastric enteral feedings. There are some contraindications for use of the device, including esophageal disruption, esophageal stricture, esophagectomy, esophageal varices, connective tissue disease involving the integrity of the esophagus and cancer of the esophagus.

In accordance with a non-limiting example, the involuntary Reflex Cough Test (iRCT) is used to evaluate the impairment and/or recovery of airway protection. Cuff pressure can also be measured by the manometer 1424. An advantageous pressure for the cuff 1402 is below the esophageal wall capillary pressure. The use of the involuntary reflex cough test is advantageous for people who are neurologically impaired to check to see if they can protect their airway. In this particular device example, pressure sensing is used in conjunction with the device. EMG determination can also be used, as well as pH sensing. Any transceiver inputs for pressure, pH or EMG could input directly into the handheld device. For example, the device could carry pressure sensors as pressure transducers 1430 at various locations on the device to measure pressure when the device is inserted within the esophagus. The transducers 1430 could have transducer leads 1432 that extend through the sump lumen 1408 or be embedded in a wall of the main tube or one of the other lumens. One pressure sensor or transducer 1430 could be in the stomach (such as at the sump lumen), another at the LES, another at mid-esophageal and/or another at the superior esophageal location. It is possible to use an air charged catheter as a pressure sensor with a separate lumen for determining pressure in the stomach, which can be used to determine intra-abdominal pressure. An air charged catheter would require some calibration. Other sensors as non-limiting examples could use fiber optic or other circuit means. The intra-abdominal pressure can be measured but also intra-thoracic pressure. Reflux can be measured by having pH sensors 1434 as inputs along the side with leads also extending through the sump lumen in this example. The handheld device can connect by wired connection or wireless connection to the various pressure, pH and EMG sensors, probes, pads, transducers, etc. It should also be understood that the catheter can be coated with a color changing material, such as for indicating the extent of acid reflux or emesis.

FIG. 20B shows the main device body in an area around the cuff 1402 with the cuff in a deflated position. FIG. 20C shows the different lumens that extend through the device to the cuff area which is shown at FIG. 20D. The lower portion of the device is shown in FIG. 20E showing the main lumen and the sump lumen.

FIGS. 20F-20L disclose an NG/OG device 1400 similar to that shown in FIGS. 20A-20E with similar components that are common between both devices having common reference numerals. In this particular example, however, the device includes a nebulizer lumen 1450 that is extralumenal to the main device body 1401 and provides a nebulizer function using a separate nebulizer port 1452 from the main lumen. This nebulizer port 1452 connects to an oxygen or air source for delivering medication such as for the involuntary reflex cough test at the esopheryngeal area for inhalation into the pulmonary tree or medicine for treating a patient. As illustrated, the nebulizer lumen 1450 terminates at a nebulizer structure or nebulizer/medication delivery mechanism having a built-in venturi 1454 to allow delivery of medication for the iRCT around a portion or all the main device body 1401 forming the tube.

Figure 20G:
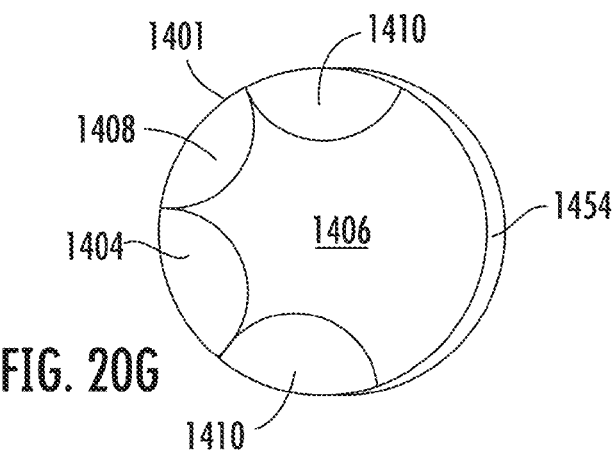
Figure 20H:
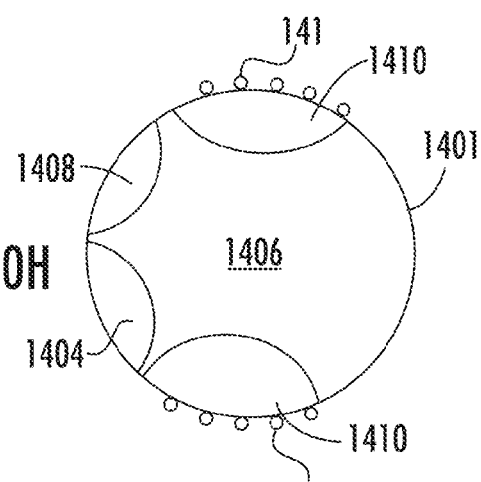
Figure 20I:
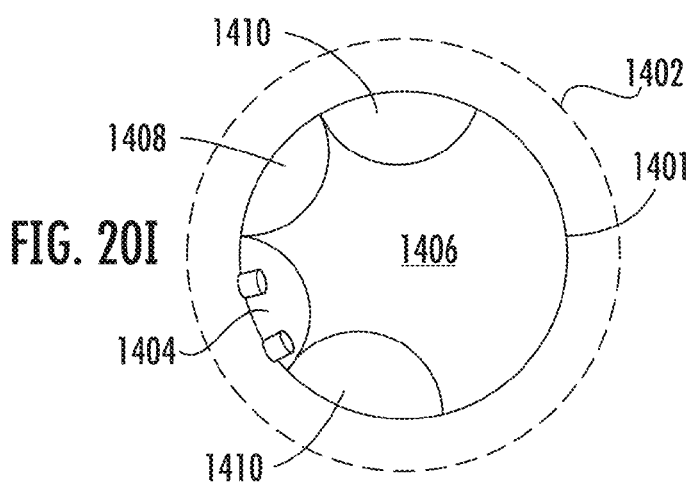
Figure 20K:
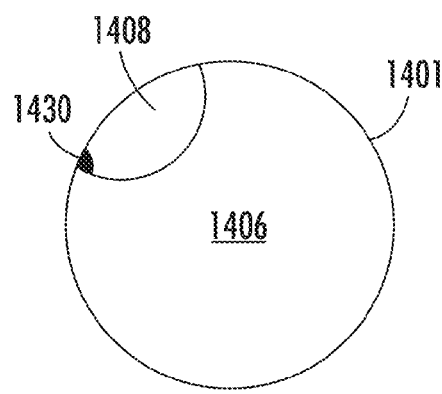

FIG. 20G shows a cross-section taken along line 20G-20G and showing the venturi of the nebulizer and the main lumen 1406, deflation/inflation lumen 1404, suction lumen 1410, and sump lumen 1408 that are similar as with the embodiment shown in FIGS. 20A-20E. The two suction lumens 1410 could merge near the proximal portion of the main body or be separate and provide either common suction at the same time above and below the cuff or individually controlled suction. The suction holes or ports as noted before include one-way valves to allow fluid into the suction lumen 1410, but not out. The valves could be formed as cut flaps that extend inward, but not outward to allow ingress, but not egress. This is advantageous such as when emesis extends upward around the tube from the stomach and can pass into the tube to be suctioned, but not passed back out. Also, secretions, if they get past the cuff, will be suctioned by the suction ports that are located above the cuff as illustrated.

The pressure transducers 1430 are located at various points such as at the distal tip at the sump to measure intra-abdominal pressure. A pressure transducer 1430 can be located below the cuff 1430 and above the cuff 1402 with leads extending through the sump lumen 1408 and connected to the handheld device. A pressure transducer 1430 in one example is located at the sump lumen as shown in FIG. 20L. As noted before, it includes pH sensors 1434 along the device that include leads extending through the sump lumen 1408, allowing pH to be measured to detect when emesis is rising from the stomach and the elevation of emesis. The pH sensors 1434 could be located at different locations such as below the cuff and above the cuff and along the main device body 1401. The coating on the device could indicate pH.

This Ng/Og device as illustrated in FIGS. 20E-20L is a multi-purpose Ng/Og device that can be used in a variety of patients who are at risk for aspiration of gastric contents, elevated intra-abdominal and/or intra-esophageal pressures, and/or abnormal airway protection. The device is not limited to the illustrated embodiments, but can be configured with all or any variation in combination of different components to fit the needs of the patient.

The main lumen 1406 extends the entire length of the device and as noted before, the device has radio-opaque markings 1420 along its length, and also measurement markings 1421 as indicia in one example along its length. The entire cuff can be radio-opaque to enhance placement. This device 1400 permits gastric decompression and can be used with a low continuous or a low intermittent suction to remove gastric contents, including liquids and gaseous materials. The device allows enteral feeding that can be administered into the gastric cavity for nutritional support. Any enteral medication administration allows medications to be administered into the gastric cavity.

The sump port 1412 as noted before is intra-lumenal with its own sump lumen 1408 and is integrated the entire length of the device. The sump port opens at the end of the device and when located within the stomach, as when the device is in operation, prevents adherence of the device to the gastric wall and also vents gastric gaseous build-up.

The nebulizer venturi 1454 permits inhalation medication administration. The venturi 1454 is extralumenal and connects to a high-flow oxygen or air source in a non-limiting example. Nebulized medications are delivered through the venturi 1454, typically at the level of the larynx and hypopharynx. The involuntary reflex cough test can therefore be administered efficiently using the device as described.

The cuff or inflation lumen 1404 provides inflation for the esophageal cuff, which as an inflatable cuff is located at the mid-esophagus section and can be inflated and deflated via the leur lock tip balloon 1422 that provides a "feel" for the practitioner to aid in pressure measurements. The pressure of the cuff 1402 can be checked using a manometer 1424, which attaches to the leur lock tip. Gross pressure can be tested manually using the indicator balloon. The esophageal cuff 1402 provides a barrier for any refluxed gastric material from entering the upper esophagus and airway. An unplanned dislodgement of the esophageal cuff does not cause injury because of the particular cuff structure as a flexible material and its configuration to collapse when necessary. Also, the amount of pressure is not excessive enough to harm the esophageal wall in most instances.

The esophageal suction ports 1416, which in this embodiment are both above and below the cuff, permits suction to occur and uses one-way port holes that are located above and below the esophageal cuff such that emesis, reflux and other material can be sucked into the suction lumen 1410 but not pass out. The suction ports 1416 open with the administration of low pressure and intermittent suction. Low suction can be applied to remove the refluxed gastric material in the lower esophagus below the esophageal cuff. The low suction can also be applied to remove material such as, but not limited to, oral or nasal secretions, medications and/or tube feeding material that is collected in the esophagus above the esophageal cuff. For purposes of identification to the nurse or other practitioner, it can be labelled as "Intra-Esophageal Access: Do Not Instill."

The sump lumen typically will carry transducer leads that extend in the lumen and out past the discharge end of the sump lumen 1408, but the leads could be embedded in the wall of the device. The handheld device or other processing device can connect wirelessly or by wired connection to the transducer leads and monitor pressure within the upper esophagus, the lower esophagus, and within the gastric cavity. Sensors or probes for pH 1434 can be included as noted before and have leads extending through the sump lumen 1408 and out past the proximal end. The leads extending out of the sump lumen for those sensors, transducers or probes can connect to a transceiver for wireless signal transmission to the handheld unit (or wired connection) in one embodiment. Any pressure transducer can send its signal not only into the handheld device, but also into a monitoring system that includes alarms to notify the staff of any increased pressures above or below the esophageal cuff or within the gastric cavity. Sensors for pH can be configured to sound an alarm such as when emesis occurs.

Typically, the nebulizer venturi 1454 will be positioned at the level of the larynx between the nasal pharyngeal area/oral pharyngeal area and allow medication to be administered. The device can be used to measure both intra-abdominal hypertension and reflux. The dimensions of this device are typically not larger than a regular NG/OG tube and not larger than 18 to about 20 French. The sump lumen is much smaller as compared to the main tube, but in this example, large enough to accommodate various leads, which could extend through other lumens. The sump lumen, however, typically remains more clean.

The Ng/Og antireflux/emesis device as described with reference to the preceding description can include suction both above and below the Lower Esophagael Sphincter (LES) as explained above. With placement of the "umbrella" or esophageal cuff close to a predetermined level such as 2-3 cm below the aortic esophageal indentation or "aortic notch," the inflation with saline or air opens a predetermined cuff shape similar to an hourglass cut in half in one non-limiting example. The bowl shape as identified above as an example collects swallowed secretions and allows passage through both directions for gases. The umbrella would open a limited amount under emesis pressure, and a sensor could flag or alert a monitoring system, triggered by the umbrella or cuff opening while at the same time, automatic suctioning could occur above the LES from the port. The device is also a fully functioning feeding tube for food, liquids or medicine to the stomach and acts as a separate reverse channel, to allow suctioning below the LES in the stomach, and the possibility for constant low-pressure suctioning for reflux above the LES. In a preferred example, the device collapses with pulling even if it is not deflated and pulled by a patient for safety. As noted before, xrays can be used to aid placement of the device in the esophagus. This device can be engineered as necessary for any severe neuro functions and risks for LES weakness or increased LER activity because of dysphagia or reflux, and protect general anesthesia patients after extubation. The device is useful for iRCT testing and protects the patient from neutral created anti-acid medicine stomach content reflux the might get past the ASIC receptors or RAR's (retinoic acid receptors).

The nebulizer lumen 1450 in one example typically extends about half the length of the tube, and in an example is flush with the side of the tube. In FIG. 20F, the device is shown broken in sections for clarity since it is not necessary to show the entire length of the device when only major components are to be illustrated. Nebulized medication enters through one of the ports at the top section of the nebulizer lumen, which terminates at the venturi as illustrated. The medication does not pass into the main tube, but around it, for example, at the level of the larynx in this example. For example, the venturi could be located between the nasal pharyngeal and oral pharyngeal and/or distal. Medication can be administered into that portion of the airway.

The suction lumen includes the one-way valves at the suction ports 1416. Suction can be activated as when emesis occurs and it is brought into the lumen. The main lumen 1406 forming the main device body 1401 provides for food and fluid to pass into the stomach while the other lumens as illustrated provide specific functions and are typically integrated with the main device body.

The esophageal cuff 1402 is located on the outside of the main tube and can be inflated and deflated as noted before. The balloon 1422 is located such that the practitioner can manually feel the pressure of the balloon to exert pressure on the cuff 1402. Manually manipulating the balloon can place pressure on the esophagus via the cuff, and thus, the practitioner can use the feel of the balloon and cuff in this non-limiting example such that the cuff will not cause tissue ischemia.

Suction can occur above and below the esophageal sphincter and suction can occur above and also below the cuff. There are, in some of these examples, one-way valves above and below the cuff that allow emesis or other material to go from outside the device to inside the tube. These one-way valves can be passive and fluid can enter through the one-way valves and be pushed down into the stomach or suctioned up in another example. The device is designed such that emesis cannot come up around the tube. This is important when the patient is unconscious and tube fed, allowing protection of the airway for the patient and protecting the patient from any lower esophageal reflux such as with involuntary events. If a patient inhales, the lower esophageal sphincter closes. If an involuntary event, such as an involuntary reflex cough occurs, and a patient has not inhaled, reflux can occur. This has been shown with a damaged or malfunctioning urethral sphincter or damaged or malfunctioning lower esophageal sphincter.

Guardian reflexes are typically parasympathetic driven. The parasympathetics are cranial and sacral and the sympathetics are cervical, thoracic and lumbar. When a patient inhales, the diaphragm drops and activates the dorsal and causes the lower esophageal sphincter (LES) above the stomach to close. If an event occurs and the internal sphincter does not close, the external sphincter is left alone. This is when patients leaked and why they often have stress incontinence. The involuntary cough happens in about 17 milliseconds and they are not able to inhale. There is no parasympathetic to close the inner sphincter, evident in graphs discussed before. This can be explained because the internal sphincter closes with inhalation. Between every cough, there is an inhalation and the diaphragm drops and the dorsal motor nucleus and para-abductal communicate with the parasympathetics from the cranial and sacral distribution. The device as explained is advantageous because when reflux occurs, and if there is an involuntary cough and reflux, the airway is protected, especially if the patient is unconscious.

When the patient aspirates, a practitioner typically may try to neutralize the stomach contents. The airway will not be able to protect itself because of the neutral pH, and the reflex cough will not activate because the acid receptors are not activated (because of the neutralized stomach). This protective device, in accordance with a non-limiting example, is advantageous to protect the patient.

Normally if the contents are acidic, even if a patient is unconscious and the cough is operative, then the patient would cough material out and this material would not move into the lungs. If the stomach has been neutralized, however, the contents of the stomach may go past the acid receptors and vocal cords and there could be an aspiration syndrome.

In the past, NG/OG tubes were not used with a patient that could not protect their airway. This protective NG/OG device as described, however, in accordance with a non-limiting example, is safely used with a patient that cannot protect their airway and especially useful when administering the iRCT in case reflex occurs. The device can be left in a patient for protection.

The sump port 1412 is integrated into the side of the main tube forming the main device body and exits the base of the tube into the stomach. The sump port vents and prevents adherence of the tube to the wall of the stomach if suctioning occurs, preventing complete vacuum and even collapse of the stomach. A pressure transducer is placed at the sump port (FIG. 20K) for pressure measurements. The various sensors, transducers and probes typically may have leads that extend through the sump lumen and extend outward to plug into the handheld device. The pressure of the stomach can be checked to give a measurement for intra-abdominal pressure and aid in determining intra-abdominal compartment syndrome resulting from excess pressure. This could be a resting pressure. It is preferred, of course, in these scenarios, that pressure not extend above 12 centimeters of water, for example, indicative of intra-abdominal hypertension. Thus, the device as described can be used not only to measure intra-abdominal hypertension syndrome, but also to measure reflex cough. Typically, the reflex cough is activated from the nebulizer venturi 1454 when the various leads 1432 are plugged into the handheld device either by wired or wireless connection. This is as effective in some instances as measuring intra-abdominal pressure from the bladder, but there are some evaluations that occur to reflect that the pressure is sometimes higher from the stomach than from the bladder, which could be a reflection of device position.

Typically, voluntary cough is higher from the stomach than from the bladder. During this process, there could be higher reference numbers for normal between the bladder and the stomach. If there is a rise in normal pressures, then there is possible intra-abdominal hypertension. Typically, the bladder is 12 centimeters of water as a cut-off and the stomach could possibly be 20 centimeters of water, but this value is to be determined with greater testing.

This device prevents reflux from hurting a patient. The pressure transducers 1430 located at the stomach below the cuff and at a point above the cuff are advantageous. If there is pressure build-up below the cuff, it is because the patient typically has vomited and there is now fluid rising and there is possibly esophageal stretch that is placing pressure on the esophagus. It is possible to have a continuous read-out at the handheld unit of the various pressures along the esophagus and in the stomach. It is possible to place alarms on the device, which will activate if there is abnormal high or low pressure. For example, an abnormal high pressure could trigger an alarm and a nurse could assess the patient to see if the patient needs to be suctioned, and whether suction needs to occur above or below the cuff. Also, the nurse could determine if there are intra-abdominal high pressures. It should be understood that the main lumen can be used to feed and the different fluid ports, transducers, sensors and other components as described before are positioned around the main lumen based on the necessary physiology and function required for the device.

The esophageal cuff 1402 is an umbrella-type device such that pressure opens the cuff and blocks emesis. This could be dangerous to the esophagus if proper designs are not used for the cuff. The cuff, i.e., "umbrella," is designed to readily collapse. If the cuff opens because of emesis or reflux, the opening could trigger a transducer operative with the cuff and activate an alarm. A pressure transducer could be located at that cuff location. If pressure occurs at the cuff by opening the cuff, it will set the alarm off. The cuff in one example could be designed as a static blocking mechanism, and thus, be a static cuff, and in other instances a dynamic cuff. The design is important to ensure that the cuff is not rigid such that it would rupture the esophagus.

Figure 20J:
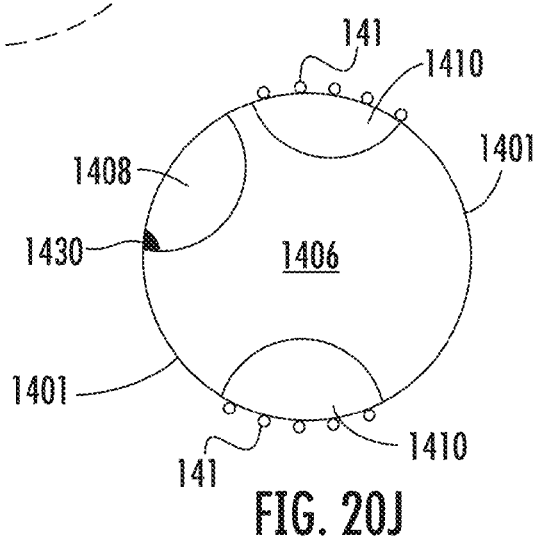
Figure 20L:
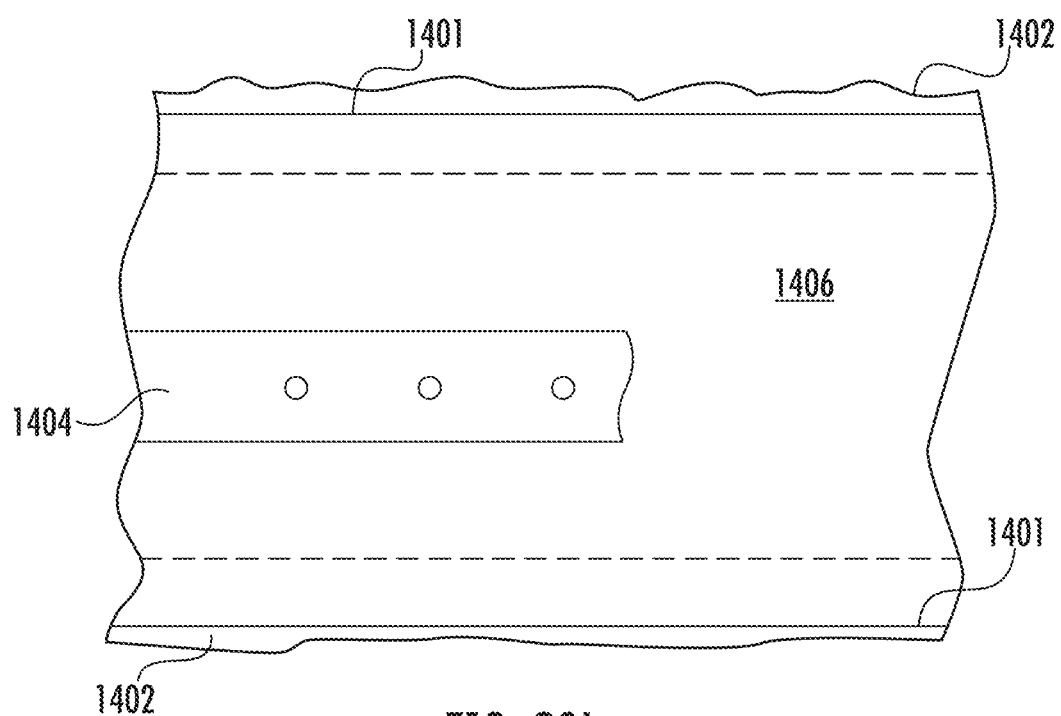
Figure 20M:
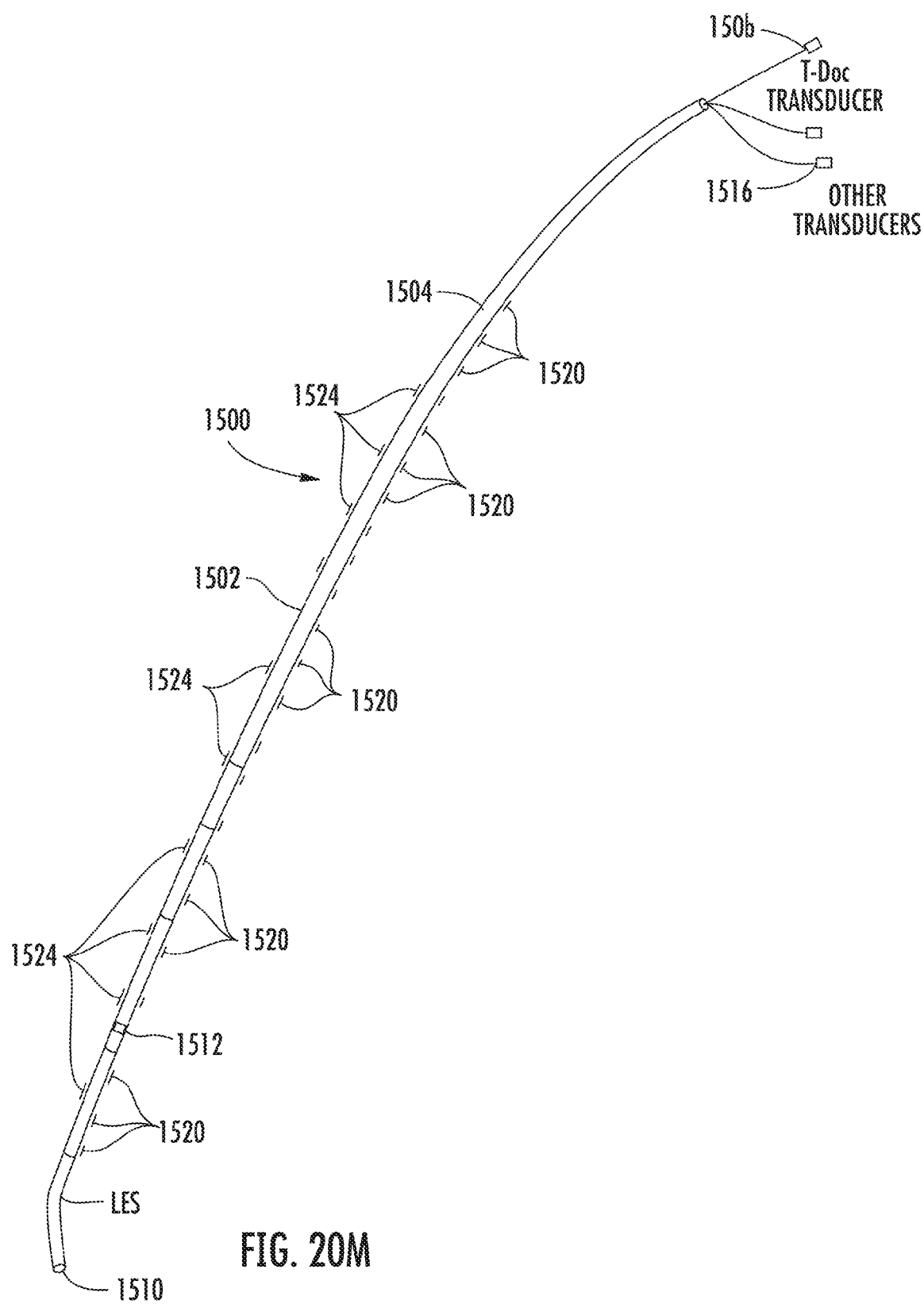
FIG. 20M is a plan view of an Ng/Og device or catheter that can be used for testing for acid reflux.

The cross-section views show suction ports above and below the cuff (FIG. 20J). Any deflate/inflate port for the cuff could be just above the cuff with a pressure transducer above and below the cuff in a non-limiting example.

As is understood, the esophagus is a low-pressure system, and the cuff will typically operate as a low-pressure system. Low intermittent pressure is about 80 millimeters of mercury, and low continuous pressure is below about 80 millimeters of mercury. The esophagus is much smaller and the suction will typically be reduced to ensure that there is no excess pressure against the walls of the esophagus to cause damage. The pressure transducers, if strategically placed depending on the type of patient, can aid this determination. Air charged catheter technology can be used for pressure measurement where changes in physiological pressure are transmitted through a micro-volume of trapped air.

It is also possible to use a valve mechanism such as disclosed in U.S. Pat. Nos. 9,005,122 and 9,005,123 that are directed to devices with a passive valve to block emesis and/or reflux and an active valve. Both of these applications are incorporated by reference in their entirety.

FIG. 20M shows a catheter 1500 as a device used in a method for diagnosing reflux during an involuntary event such as the involuntary reflex cough test. As illustrated, this catheter 1500 does not include any cuff as in previous embodiments shown in FIGS. 20A-20E and 20E-20L and includes a catheter body 1502 having a single lumen 1504 in this example with a T-DOC transducer 1506. It is formed as a small, semi-soft catheter. The adult size is about 6 French and the pediatric size is about 1-2 French. Two pressure sensor areas 1510, 1512 are formed for sensing pressure, for example, by using pressure transducers that are placed at the tip of the catheter and approximately 10-15 centimeters from the tip. Different types of sensors could be used and transducer leads 1516 could extend along the side or in the catheter to the end. The catheter could be an air charged catheter. In one example, the catheter is coated with a pH sensitive material 1520 that will change color when exposed to a pH less than about 4.0, indicating reflux. Measurement markings 1522 can be inserted or printed throughout the length of the catheter. In one example, the catheter is an air-charged (T-DOC) for pressure measurement, but other types of sensing mechanisms such as pressure sensors could be used as understood by those skilled in the art. Fiber optics could be used. The catheter is radio-opaque and includes such markings 1524, if radiologic placement is required and it can include in-patient and out-patient indications.

The catheter can operate as an Ng/Og device and is inserted orally or nasally into the esophagus and through the lower esophageal sphincter (LES) into the proximal stomach. Placement is measured from the lips (oral) or nares (nasal) to the TMJ (temporomandibular joint) to about four-finger breadths sub-xyphoid for adults.

The first sensor 1510 is located in the proximal stomach and can measure intra-gastric/intra-abdominal pressure. The second sensor 1512 is located approximately in the mid-to-lower esophagus and can measure intrathoracic pressure. A pressure grading can be over the LES. EMG information typically can be measured to simultaneously record changes in pressure and gradients. EMG can be measured from the paraspinals as described before. EMG sensors could be located at selected locations on the catheter for EMG measurement in some examples. The catheter can include color change indicia for the pH sensitive material to measure the height of refluxed, acidic gastric contents. The catheter includes pH sensors as noted before.

The catheter 1500 has the potential to identify SUI in conjunction with bladder catheters, assess neurological airway protection (represented as one summated value) and SUI, and additionally assess bladder physiology and categorize any classification with a programmed algorithm in incontinent patients using this one small catheter with EMG measurement. Any inputs of different values can be to the handheld device as described.

When a different type of the same sized air charged gastric catheter is inserted from above, i.e., P.O. or NG, the device will measure neurological airway for protection and assess gastro esophageal reflux from the involuntary maneuver epoch using the iRCT. This gastric catheter, which can also measure pressure below the LES, can predetermine gastric baseline pH and baseline esophageal pH above the LES at standard acid reflux levels already used in other pH testing. From that set up, with any catheters plugged into the handheld device (or eventually wirelessly to a wireless processing device), when given an iRCT, the handheld processing device will assess if reflux is present during the iRCT epoch, such as when it occurs during and/or after the epoch by pH change at these levels. Whether the patients are being treated with acid neutralizers or not, the determined baseline sets the ability to asses pH change when and where in the esophagus it occurs.

This approach will assess the severity of reflux compared to the response of the iRCT and magnitude of the involuntary cough epoch. Depending on the acid reflux elevation compared to the iRCT epoch, without inhalation tonicity protection, it could be instrumental in stratifying reflux severity and pivotal in directing treatment and demonstrating, with repeat testing, the efficacy of the treatment given. This device and process can be used for adult, pediatrics and newborn patients.

If gastroesophageal reflux occurs regularly, it is most likely secondary to an event that is a non-voluntary event, for example, a belch or involuntary cough, thus occurring without inhalation tonicity protection. The reflex acid stimulation to the lung could be from the distal esophagus reflex and very slow causing delayed cough, possibly involuntary coughs (possibly a vicious cycle) or irritable lung reactions causing inhalation and voluntary coughs. Regardless, they would not be temporally correlated by cough and reflux. This is reported in Chang, "An objective study of acid reflux and cough in children using an ambulatory pHmetry-cough logger" published online on Jun. 1, 2010 at Arch Dis Child. The cough sensor as described in Chang could not distinguish the different types of cough.

A question arises if an iRCT epoch when measured is temporarily related to reflux from the stomach during the epoch. It does not matter if there is a small distal esophageal reflux, which is supported by Irwin in the Abstract entitled, "The Cough Reflex and Its Relation to Gastroesophageal Reflux," Am J Med, March 2000, or a huge geyser airway laryngeal reflux that the ENT's describe as causing severe larynx damage over time because of acid burn. Both reflux events can hurt the lungs over time eventually.

Reflux should be diagnosed during the actual involuntary event when there is little or no inhalation tonicity protection. This will lead to appropriate treatment decisions to protect the lungs, i.e., acid suppression versus Fundoplication. The catheter device as described could be used for airway neuro measurement and bladder physiology, as well as mouth to stomach to prove reflux during an involuntary maneuver. In one example, this may require different types of catheters for different setups that all use the one handheld device for processing.

It should be understood that in the embodiments described above, the cuff operates similar to an umbrella. When the force of emesis hits it, the cuff will expand evenly without tearing or hurting the esophagus. The cuff material is typically a soft material. It should also be understood that this is advantageous because stroke could cause lower esophageal weakness and involuntary cough will not allow a patient to have inhalation protection in some instances. The cuff on the device provides such protection. The NG/OG tube as described with the cuff acts as an esophageal reflux protection device to protect a patient from the the reflux caused by any weakness of the lower esophageal sphincter from both involuntary cough or muscle weakness from neurological injury or similar problems. When involuntary cough occurs, the stomach typically does not close down. The cough can cause reflux, which causes more cough as a vicious cycle. In some instances, it is possible have a Foley catheter and the smaller catheter tube as shown in FIG. 53 and leave the Foley and pull the catheter after a cough is measured for reflux. It is also possible that the Salem sump as described can be radio-opaque such as with a coating or a strip itself. The sump port itself could be radio-opaque to indicate where the port extends down into the stomach, such as about 6 centimeters in one example. Capillary pressure of the esophageal cuff can be about 7 to about 8 centimeters of water as a safety factor. The tube feeding channel, such as the main tube, would be a separate channel from the suction channel to ensure that the food is not mixed with any emesis.

The devices, catheter and functions as described above are advantageous. If there is an involuntary cough and reflux, a patient can be protected even if they are unconscious. For example, at times the stomach may be neutralized in a clinical setting and the protective device is advantageous to protect a patient from regurgitating their own stomach contents. Normally, when the stomach contents are acidic, and even if a patient is unconscious, if reflux occurs, a patient would normally cough it out and the reflux or emesis would not pass into the lungs. If the contents are neutral, however, they could discharge past the acid receptors and vocal cords, causing aspiration syndrome. The device and methodology therefore would test and prevent reflux damage and protect a patient's airway. The device can both feed and protect the patient.

Another advantageous aspect is that it is possible to accomplish involuntary cough and measure stomach pressure or intra-abdominal pressure during involuntary cough with the device as described. The involuntary maneuver as a diagnostic tool with the device can be used to diagnose reflux. When the device is pulled out of a patient, the configuration of the cuff allows the cuff to collapse.

The devices can be used to measure the cough epoch in conjunction with EMG. It is advantageous to diagnose the cough epoch and also diagnose severity of disease. The devices in conjunction with other measurements can be used to diagnose severity of reflux during the involuntary epoch and determine the best course of treatment. For example, if surgery is required or pelvic floor exercises or other treatment required. It allows a neuro anatomical finding. The devices can be used to measure pressure such as the abdominal pressure and reflux at the same time not only during the time of the reflux, but also determine the height of the reflux for severity.

It should be understood that a pH probe can be located in the stomach, one at the LES, one at the mid-esophageal region, and one at the superior esophageal region or any combination. pH sensors could be formed electrodes. The devices could have color changing indicia as a coating on all or part of the device to aid in measuring pH and reflux. The devices can include pH sensors and pressure sensors, for example, an air charged sensor. Fiber optics can be used as noted before. A device could be used to protect a patient's airway, feed the patient, administer medication, and vacuum or "suck up" contents and prevent aspiration in the stomach and esophagus. The device operates as a diagnostic tool in another example. The EMC shows a duration of the epoch or event and can be measured. It is typically measured from the paraspinals in an example. The device is used to diagnose GERD and prevent reflux in a non-limiting example.

It should be understood that the involuntary maneuver as described before can be used to test for damaged or malfunctioning abdominal-pelvic intrinsic sphincter. When either a physical or chemical substance stimulates receptors in the laryngeal mucosa, cough may result. Whether the cough is an involuntary reflex or a volitional response depends upon the quantity and type of stimulus. The laryngeal expiratory reflex (LER) is an involuntary, brainstem-mediated reflex. The vagus (X) nerve in one example mediates the afferent component of the LER, and the efferent component is conveyed via the vagus, phrenic, intercostal and abdominal nerves. The reflex cough test (RCT) is a cranial nerve examination assessing both the afferent sensory and efferent motor limbs of the laryngeal expiratory reflex. It is believed that the RCT is presently the only means to test the integrity of the LER.

FIG. 21 is an illustration of an exemplary handheld processing device 560 such as described in the incorporated by reference patent publications. More particularly, it should be understood that this handheld processing device 560 can be used by a nurse practitioner or doctor and receive input as wireless signals or as wired input directly from catheters as Ng/Og devices. Also, this handheld processing device 560 can incorporate the circuit and functions as disclosed in the incorporated by reference publications.

FIG. 22 is a block diagram that illustrates a computer system 500 for the handheld processing device 560. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504.

Computer system 500 may be coupled via bus 502 to a display 512, such as a LCD, or TFT matrix, for displaying information to a computer user. An input device 514, for example buttons and/or keyboard, is coupled to bus 502 for communicating information and command selections to processor 504. Another type of user input device is cursor control, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 operates in response to processor 504 executing one or more sequences of instruction. Execution of the sequences of instructions causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks. Volatile media includes dynamic memory, such as main memory 506. Transmission media includes coaxial cables, copper wire and fiber optics, including the wires that comprise bus 502. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infrared transmitter to convert the data to an infrared signal. An infrared detector can receive the data carried in the infrared signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

The handheld device 560 preferably uses wireless technology that could include infrared (IR), Bluetooth, or REID technology for communicating with the wireless transceiver in the wireless module of the flow meter or part of the nebulizer. The handheld processing device 560 includes a wireless module 580 that would work in conjunction with the transducer interface and controller 518 and the secondary interface 581 and sends and receives readings through the antenna 582 or other system that could be used. The wireless module 580 could be located at different locations.

As illustrated, it is possible to use a wireless interface that interfaces with the handheld processing unit. The wireless interface can include a transceiver and a processor and an interface to catheters, Ng/Og devices, and EMG pads or other similar items. The wireless interface could transmit signals to the wireless unit. It is possible that any catheter body could include a small wireless interface that transmits short range signals to the handheld processing device or a personal computer or similar device.

For purpose of technical instruction, there now follows a general description of physiology for the involuntary reflex cough test (iRCT), which activates the Nucleus *Ambiguus*, which is also disclosed in some of the incorporated by reference patent publications. The nebulizer with the flow sensing function is adapted for measuring both voluntary cough and involuntary reflex cough, such as explained in the incorporated by reference patent applications. The iRCT selectively activates the Medial Motor Cell Column (MMCC) of the spinal cord rather than the (Lateral) LMCC to fire muscles embryologically predetermined to be involuntary cough activated muscles in the pelvis. In the past, urologists did not selectively activate MMCC without overtly activating the LMCC. Magnetic stimulation or electrical spinal cord stimulation activate both cell columns and thus it is not possible to sort out pathology with these. Magnetic stimulation or other approaches from CNS activation set off both columns.

The pelvic muscles that typically are activated with MMCC cough activation include the lumbar-sacral L5/S1 paraspinal axial musculature, which facilitates inpatient continence screening. An example is through MMCC iRCT muscle activation, obtaining L5/S1 paraspinal firing but not L5/S1 lateral gastrocnemius activation because the gastroc muscles are limb muscles activated primarily through the LMCC.

The L-S paraspinals are easier to access with a large pad placed above the sacrum on the midline that contains active, reference and ground combined. It is not important to determine lateralization of the activity like needle EMG for radiculopathy, but only if activation occurs reflexively where the onset latency is under the pressure activation of the abdomen such as the Levator Ani. This is a poor muscle for these purposes because people train it to activate and set their pelvis if the person senses any intra-abdominal pressure elevation. Also, it is difficult to get pads to stick to that area with hair, perspiration, fungal infections or bowel/bladder incontinence present, and other factors.

Some examples have been developed and studied, including a normal CNS patient with Lumax bladder and bowel catheters and pads at L5/S1 paraspinals and a separate EMG machine and electrodes at the pelvic floor in a standard 3:00 and 9:00 o'clock set-up to demonstrate simultaneous involuntary activation with iRCT. This sets off the pelvic floor muscles. Thus, normal airway protection data is obtained and normal CNS data to L1 (where spinal cord ends). The set-up includes a complete T12 that cannot void and needs intermittent catheterization with the same set up, thus demonstrating data for normal airway but no L5/S1 EMG activation by MMCC with all the other data necessary to prove an unsafe bladder by the algorithm. A quadriplegic can demonstrate abnormal airway protection and abnormal EMG activation at both paraspinal and pelvic floor muscles with unsafe bladder measurements that follow the algorithm.

It should be understood that iRCT is an involuntary maneuver that activates embryologically predetermined muscles for airway protection and continence that travel primarily through the MMCC in the spinal cord. Different varieties of lesions are captured and determined with summated interval data approach for general screening purposes.

It is known that the laryngeal cough reflex (LCR) is a strong brainstem-mediated reflex that protects the upper airway by preventing aspiration, or the entrance of secretions, food, and/or fluid into the airway below the level of the true vocal cords (rima glottidis), through elicitation of an involuntary cough. The LCR is activated through the stimulation of cough receptors in the vestibule of the larynx. One way this is achieved is through the inhalation of chemostimulants, such as tartaric acid. Studies have shown that if the LCR is intact, the subject will involuntarily cough (normal LCR) upon inhaling a solution containing TA.

In one non-limiting example, the iRCT involves the inhalation of a nebulized 20% normal saline solution of L-TA (Tartaric Acid). Subjects are asked to perform 1 to 3 effective, full inhalations (about 15-20 second exposure by mouth for tidal breathing wearing a nose clip) from a standard jet nebulizer with at least 50 psi from an oxygen wall unit or tank that produces an average droplet diameter of 1 to 2 microns or less. The nebulizer output is 0.58 mL/min. The initiation of an involuntary cough reflex after any one of the inhalations is the end point of the procedure.

Nebulized TA is a chemical tussive that stimulates irritant receptors in the mucosa of the laryngeal aditus. Mild irritation of these receptors results in nerve impulses being conveyed by the internal branch of the superior laryngeal nerve (ibSLN) to bulbar centers of the brainstem. This nerve constitutes the afferent sensory component of the LCR arc. The efferent component of the LCR is mediated through the vagus, phrenic, intercostals and thoracoabdominal nerves.

Inhaled TA is selective in stimulating rapidly adapting ("irritant") receptors (RARs), in the supraglottic region. In humans, bilateral anesthesia of the ibSLN abolishes TA-induced cough and permits tidal breathing of the nebulized vapor without coughing, supporting the idea that the RARs are responsible for TA-induced cough.

The physiological response from inhalation of TA in a normal subject is abrupt, forceful coughing of short duration. Using a 20% solution of inhaled nebulized TA is a safe, reliable way to assess the sensation in the supraglottic laryngeal region and subsequently the neurologic circuitry of the LCR. In addition, the ability of the iRCT to predict the integrity of the protective LCR in subjects with stroke has been studied.

A 20% solution of TA as an aerosol causes cough by stimulating sensory nerves in and under the laryngeal epithelium. These nerves have been identified histologically, and the reflexes they cause have been identified. The sensory nerves can be stimulated by both non-isosmolar and acid solutions. Tartaric acid may act in both ways, but the balance between them is uncertain.

The nerves are stimulated by the opening of membrane channels in the nerve terminals. More than 20 categories of channels have now been identified, the opening of which will allow calcium flow into the nerve (and also sodium, with exit of potassium), with the result that an action potential is set up, which travels to the brainstem in the central nervous system (CNS), and reflexively induces cough.

Several different types of sensory nerve ending in the larynx have been identified that may mediate cough and other defensive reflexes. They have been extensively studied, mainly in experimental animals by recording the action potentials in their nerve fibers. The probable candidates for cough are the RARs or 'irritant' receptors. These are highly sensitive to mechanical stimuli, to hyperosmolar solutions, and to acids.

Once stimulated, the sensory nerves will induce a variety of defensive reflexes, which protect the lungs from invasion of harmful material. These include cough (an inspiration, followed by a forced expiration against a closed glottis, followed by opening of the glottis with an expiratory blast); the laryngeal cough expiratory reflex (LCER, a powerful expiratory effort with the glottis open); and the glottal closure reflex. In some instances a reflex apnea can be produced. The balance of these reflexes may depend on the nature and the strength of the stimulus. In the case of TA, the LCER seems to be dominant, possibly followed by glottal closure, and the pathophysiological advantage of this response in preventing aspiration is obvious.

There now follows an analysis and test results in greater detail that explain the advantageous use of the involuntary reflex cough test (iRCT) for investigating and diagnosing not only SUI, but also physiological abnormalities such as neurologic deficiencies. The nebulizer as described can be used in conjunction with testing. It should be understood that there are differences between normal and neurological patients.

The EMG from the parineal muscles respond almost simultaneously to the onset of the voluntary cough because the patient does not want to leak. With the involuntary reflex cough test, on the other hand, the fast fibers that are set off reach the abdominal muscles quickly, such as in 17 milliseconds as an example. the patient is not able to set their pelvis. In some of the graphs reflecting urodynamic testing as will be described, it is evident that the onset of the EMG activity does not happen at the same time the pressure rises. Some people that have neuropathy, for example, spinal stenosis or nerve injury (even if it is mild), have a situation that prevents the reflexes from closing before the pressure has changed to push on the bladder. It is not possible to obtain this diagnostic tool methodology unless the involuntary cough reflex test is accomplished. When the involuntary reflex cough test is accomplished, it is possible to demonstrate a latency delay and show that the pathophysiology is a neuropathic problem rather than a structural problem. It is possible to separate the pathophysiology using the involuntary reflex cough test and methodology as described.

In one example, a female patient could have a weak spinal cord and her physiology is normal. This patient may not leak during the test, but the patient cannot protect her airway. Thus, using the methodology apparatus and system associated with the involuntary reflex cough test, in accordance with non-limiting examples, it is possible not only to diagnose an unprotected airway, but also to diagnose normal bladder physiology, including the neurophysiology to the patient's sphincter closure process. This is advantageous because it is then possible to determine when someone cannot protect their airway, even though they may have a normal bladder. Conversely, there are patients with a normal airway, but cannot control their bladder. This process and system as described is able to make that diagnosis and thus the involuntary reflex cough test is an advantageous medical diagnostic tool. For example, it is possible to have a patient with a poorly functioning bladder and normal airway and use of the test allows a doctor to find lower urinary tract symptoms and neuropathology. It becomes possible to diagnose a level of lesion in a patient with a full comprehensive neurologic examination using the involuntary reflex cough test, methodology and apparatus as described.

It is possible in one example to measure pressure from a bladder catheter and determine at the same time EMG signals using the EMG electrodes at the L5/S1 in conjunction with the measured involuntary reflex cough test and urology catheter sensing. This is advantageous compared to placing electrodes at the perineal muscles on each side of the sphincter.

It has been found that EMG signals obtained from the perineal muscles have EMG activity from the non-involuntary muscles, i.e., the voluntary muscles blacking out and making analysis difficult because of the signal interference. When the electrodes are placed at the back at the L5/S1 junction, on the other hand, there is nothing else but the paraspinal muscles. It is bone below on each side at the L5/S1 junction. The electrical impulses can be obtained that determine the number of cough impulses coming down through the patient. This is accomplished even if a person has much adipose. The electrode pad used at the L5/S1 junction, in one non-limiting example, typically has an active reference and ground. A pad holds this active reference and ground and the leads as the active reference and ground are plugged into the handheld device (or wireless sensing device in another example) and transmit data to the processor. At least one catheter is also plugged into the handheld device (or wireless sensing device) and measures bladder pressures. A rectal catheter can also be used in some examples. The processor receives EMG signals and determines when the cough event is over.

The involuntary coughs are not hidden by interference when measured from the lower back at the paraspinals as described. This allows a clinician to determine coughs from the bladder when the EMG located at the L5/S1. In one aspect, the area under curve and the average pressure is determined for the cough event corresponding to the involuntary reflex cough test. When this involuntary component of the cough ends, in one example, it becomes silent EMG activity for a period of time. The pressures are at baseline for a period of time, which corresponds in one example to an inhalation. The involuntary component is over.

Sometimes with the involuntary reflex cough test, the cough occurs five times (C5) or even six times without breathing, but when the patient stops to breathe, the event is over. Using the programming applied with the processor in the handheld device, it is possible to calculate the variables inside the wave as to the involuntary cough and determine airway protection capability. Thus, it is possible to determine and measure cough by defining through appropriate data processing the involuntary cough event compared to the whole cough epoch. For example, a patient could cough ten times, but only the first four are part of the involuntary cough event. The coughs after that event are not part of the epoch.

The programming includes algorithm branches resulting in a conclusion of unsafe bladder based on the data analysis. It is possible to calculate from the waveforms information necessary for assessing airway protection ability. It should be understood that taking the EMG from the L5/S1 is also a better situation for the doctor or clinician, and the patient, since it is more acceptable in a hospital, outpatient or inpatient setting. The doctor or clinician does not have to bend down or stoop and look near the crotch area and place pads since the EMG can now be taken from the paraspinals. Also, the placement of pads and electrodes at the paraspinals is advantageous when patients are standing. If pads are placed at the perineal area, sweat and other problems could cause those pads to become loose and good signals may not be obtained. Also, it should be understood that the perineal muscles do not fire involuntarily. The sphincter may fire involuntarily, but that would create more noise as noted before. Electrodes are not placed at the vagina, but are placed at the paraspinal area instead.

This information obtained from iRct and the EMG taken at the paraspinals allows the doctor or clinician to obtain data leading directly to a diagnosis. For example, some patients that have urinary stress incontinence may have a normal airway in this analysis. It has been found by experimentation that the normal airway is about 50 centimeters water average intra-abdominal pressure. It should be understood that the vesicular pressure (bladder pressure) can track intra-abdominal pressure and terms are often similar and used together. "Bladder" or intravesicular pressure is often used to determine and equate with intra-abdominal pressure. The two are sometimes used interchangeably. Stress urinary incontinence and/or bladder physiology can be diagnosed. The system and method as described leads directly to diagnosis. Fifty centimeters average intra-abdominal pressure over time has been found to correspond to an involuntary reflex cough test normal airway. Thus, the standard deviations or other percentages from that value are used in one non-limiting example to determine an abnormal airway. In a conducted study, the actual value is determined to be about 50.6 centimeters water as compared to voluntary cough values of about 48 centimeters of water. In an outpatient setting, it is possible to have the nebulizer (and drug) and only a pad and test SUI. In hospitalized patients or inpatient settings, this combination is used to measure airway and bladder physiology and the test combination includes a catheter.

It should be understood that the involuntary cough reflex test (iRCT) gives a higher pressure average than obtained using a voluntary cough test. The involuntary cough reflex test is thus a valuable medical diagnostic tool. In one example, four variables are significant in this analysis. These variables include: (1) duration of the event; (2) average intra-abdominal pressure of the event; (3) peak intra-abdominal pressure (max) of the event; and (4) area under the curve. Using these four variables, it is possible to process the received data and obtain a specific diagnosis that could not otherwise be obtained without the use of the involuntary reflex cough test. Individual deficits in a specific variable or combination of variables are used to characterize specific diseases and problems and useful as a medical diagnostic tool.

Figure 23:
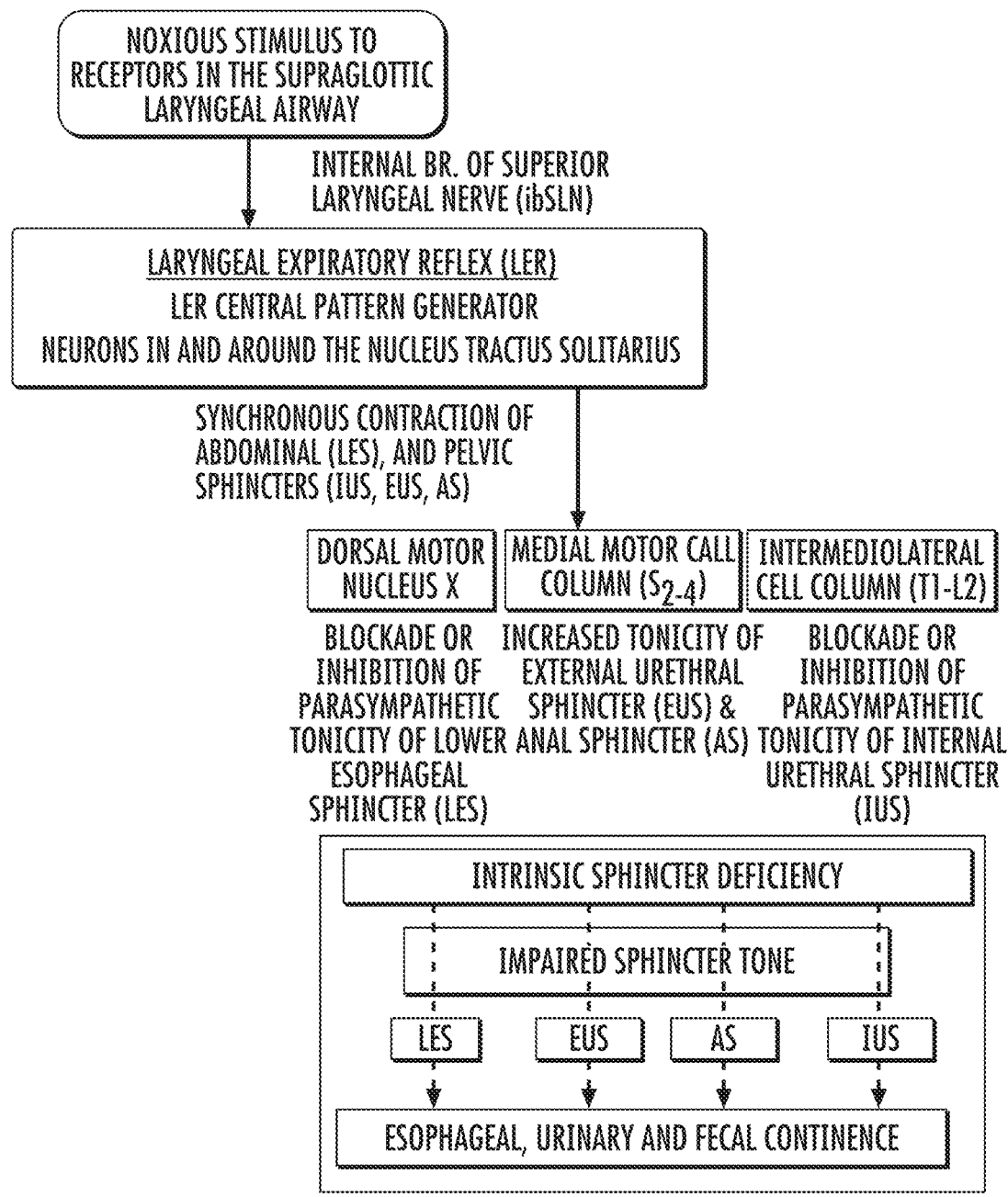
FIG. 23 is a block diagram showing an outline of the laryngeal expiratory reflex (LER) and results with the intrinsic sphincter deficiency and esophageal, urinary and fecal continence.
Figure 24A:
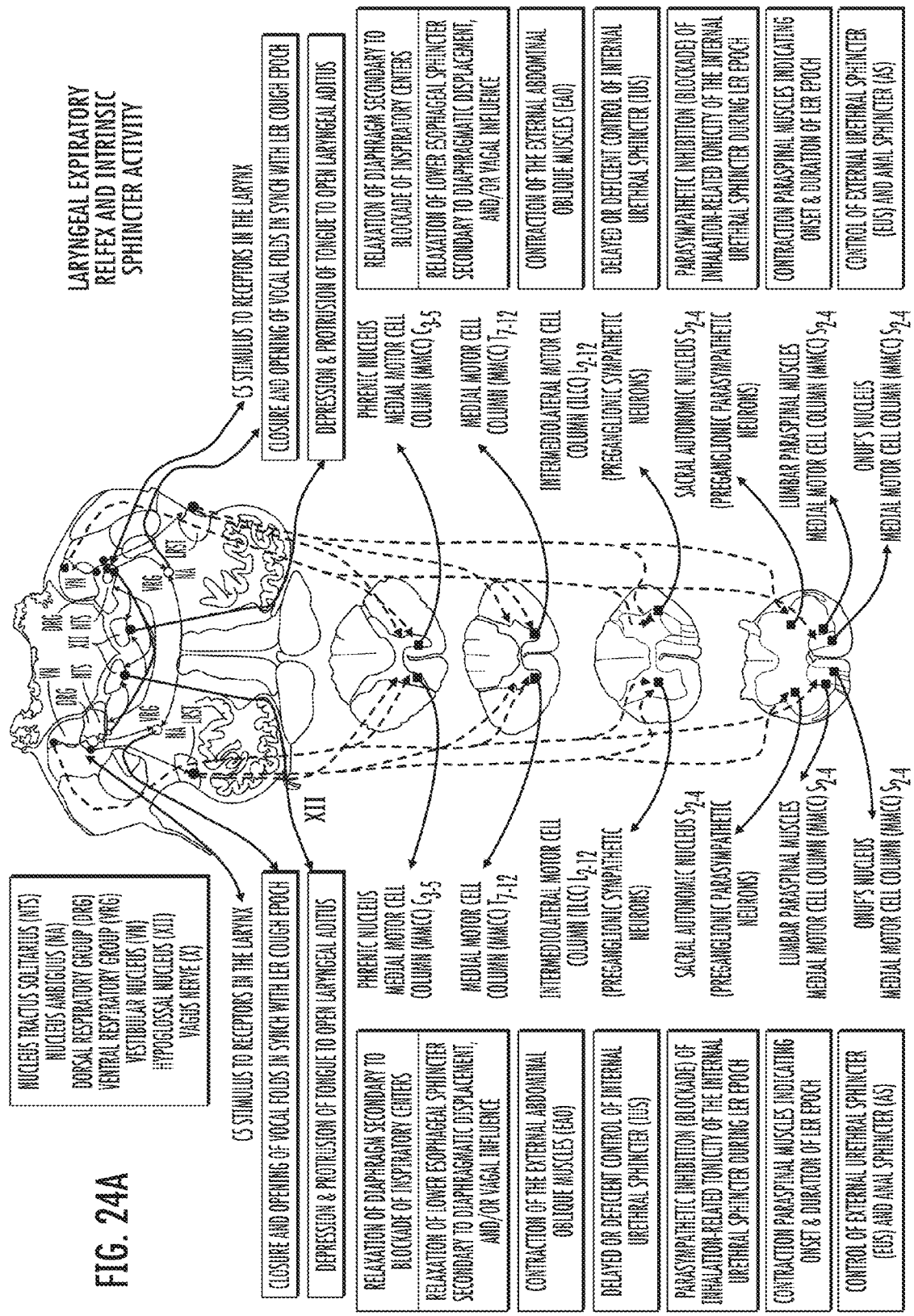

The parent '841 application also discloses FIGS. 23, 24A and 24B corresponding to FIGS. 23, 24A and 24B of the instant application.

FIG. 23 is a block diagram showing a laryngeal expiratory reflex (LER) flow and indicates the different effects from activation such as the dorsal motor nucleus X, the medial motor cell column, and the intermedial lateral cell column.

FIG. 24A is a diagram detailing what occurs during the LER (laryngeal expiratory reflex) and intrinsic sphincter activity. This diagrams a schematic of the LER neural circuits. FIG. 24B illustrates voluntary cough (VC) pathways. There are some key points regarding VC, micturition, and the brain stem mediated LER.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for evaluating a patient for a physiological abnormality, comprising:
   inserting a urinary catheter within a patient's bladder, the urinary catheter having a first pressure sensor on the surface of the catheter and positioned within the patient's bladder for measuring bladder pressure and a second pressure sensor on the surface of the catheter and positioned at the mid-urethral sphincter for measuring mid-urethral pressure at the mid-urethral sphincter;
   measuring the bladder pressure and mid-urethral pressure during at least one breath cycle;
   processing data representative of the bladder and mid-urethral pressures obtained during the at least one breath cycle within a processing device;
   inducing an involuntary reflex cough event within the patient during the at least one breath cycle; and obtaining an electromyogram (EMG) form the involuntary cough activated paraspinal muscles while inducing the involuntary reflex cough event and processing, within the processing device, the pressure data obtained from the bladder and mid-urethral sphincter with the EMG data received from the involuntary cough activated paraspinal muscles to diagnose a physiological abnormality within the patient.

2. The method according to claim 1, wherein the urinary catheter further comprises a third pressure sensor on the surface of the urinary catheter and positioned at the external urethral sphincter to measure pressure at the external urethral sphincter during the at least one breath cycle and processing data representative of the pressure at the external urethral sphincter with the data representative of the bladder and mid-urethral pressures to diagnose the physiological abnormality.

3. The method according to claim 1, wherein the method further comprises inserting a rectal catheter within the rectum of the patient, the rectal catheter having a pressure sensor on the surface of the rectal catheter and positioned within the rectum of the patient for measuring pressure within the rectum during the at least one breath cycle, wherein data representative of the pressure within the rectum is processed with the pressure data from the bladder and mid-urethral sphincter to diagnose the physiological abnormality.

4. The method according to claim 1, wherein the urinary catheter includes a balloon configured to fix the urinary catheter within the bladder.

5. The method according to claim 1, wherein the at least one breath cycle includes a plurality of breath cycles, and the method further comprises having the patient voluntarily cough during at least one of the plurality of breath cycles.

6. The method according to claim 1, wherein the method further comprises diagnosing stress urinary incontinence within the patient.

7. A system for evaluating a patient for a physiological abnormality, comprising:
a urinary catheter insertable within a patient's bladder, the urinary catheter having a first pressure sensor on the surface of the catheter and configured to be positioned within the patient's bladder when the catheter is inserted within the bladder for measuring bladder pressure and a second pressure sensor on the surface of the catheter and configured to positioned at the mid-urethral sphincter for measuring mid-urethral pressure at the mid-urethral sphincter;
a processing device connected to the first and second pressure sensors and configured to receive the measured bladder pressure and measured mid-urethral pressure during at least one breath cycle and process the data representative of the bladder and mid-urethral pressures obtained during the at least one breath cycle;
a nebulizer containing an agent that induces an involuntary reflex cough event within the patient during the at least one breath cycle and wherein the processing device is configured to receive pressure data during the involuntary reflex event; and
at least one electromyogram pad (EMG) configured to be attached to the lumbar region of the patient's back and obtain EMG signals from the involuntary cough activated paraspinal muscles during the involuntary reflex cough event and the processing device is connected to the EMG pad to receive the EMG data and process the pressure data obtained from the bladder and mid-urethral sphincter with the EMG data received from the involuntary cough activated paraspinal muscles to diagnose a physiological abnormality within the patient.

8. The system according to claim 7, wherein the urinary catheter further comprises a third pressure sensor on the surface of the urinary catheter and configured to be positioned at the external urethral sphincter to measure pressure at the external urethral sphincter during the at least one breath cycle and wherein the processing device is connected to said third pressure sensor and configured to receive the data representative of the pressure at the external urethral sphincter to process that data with the data representative of the bladder and mid-urethral pressures to determine the physiological abnormality.

9. The system according to claim 7, further comprising a rectal catheter configured to be inserted within the rectum of the patient, the rectal catheter having a pressure sensor on the surface of the rectal catheter and configured to measure pressure within the rectum during the at least one breath cycle, wherein the processing device is connected to the pressure sensor on the surface of the rectal catheter to receive data representative of the pressure within the rectum and process with pressure data from the bladder and the mid-urethral sphincter to diagnose the physiological abnormality.

10. The system according to claim 7, wherein the urinary catheter includes a balloon configured to fix the urinary catheter within the bladder.

11. The system according to claim 7, wherein the processing device is configured to receive pressure data when a patient voluntarily coughs during the at least one breath cycle.

12. The system according to claim 7, wherein the processor is configured to process the pressure data to diagnose stress urinary incontinence within the patient.

* * * * *